(12) United States Patent
Alfheim et al.

(10) Patent No.: US 6,498,945 B1
(45) Date of Patent: Dec. 24, 2002

(54) SONODYNAMIC THERAPY USING AN ULTRASOUND SENSITIZER COMPOUND

(75) Inventors: Jan Alan Alfheim, Hagan (NO); Paul Mark Henrichs, Houston, TX (US); Eric Paul Hohenschuh, Berwyn, PA (US); Edvin Wilheim Johannesen, Oslo (NO); William Anthony Sanderson, deceased, late of Wayne, PA (US), by Audrey W. Sanderson, executor; Robert Allen Snow, West Chester, PA (US)

(73) Assignee: Amersham Health AS, Oslo (NO)

( * ) Notice: Subject to any disclaimer, the term of this patent is extended or adjusted under 35 U.S.C. 154(b) by 0 days.

(21) Appl. No.: 09/435,616

(22) Filed: Nov. 8, 1999

Related U.S. Application Data

(63) Continuation of application No. PCT/GB98/01444, filed on May 19, 1998.
(60) Provisional application No. 60/048,487, filed on Jun. 3, 1997.

(30) Foreign Application Priority Data

May 19, 1997 (GB) .............................. 9710049

(51) Int. Cl.$^7$ ............................. A61B 5/00; A61N 7/00; A61K 41/00
(52) U.S. Cl. ............................. 600/407; 601/2; 604/22; 424/9.1; 600/431
(58) Field of Search ................................. 600/439, 407, 600/431; 604/890.1, 19, 22; 601/2, 3; 424/9.5, 9.52, 9.1, 9.3, 9.322, 9.4, 9.411, 9.6

(56) References Cited

U.S. PATENT DOCUMENTS 4,207,405 A * 6/1980 Masler, III et al. ......... 525/328
4,971,991 A    11/1990 Kohshiro et al.
5,016,615 A *  5/1991 Driller et al. ................... 601/2
5,040,537 A *  8/1991 Katakura ..................... 600/431
5,283,255 A *  2/1994 Levy et al. .................. 514/410

(List continued on next page.)

FOREIGN PATENT DOCUMENTS

| WO | WO 94 28874 A | 12/1994 | |
|---|---|---|---|
| WO | WO 95 15118 A | 6/1995 | |
| WO | WO 97 18851 A | 5/1997 | |
| WO | WO 98 01131 A | 1/1998 | |
| WO | 98/52610 | * 11/1998 | .......... A61K/41/00 |

OTHER PUBLICATIONS

Yumita N. et al., "Sonodynamically induced antitumor effect of gallium–porphyrin complex by focused ultrasound on experimetal kidney tumor", Cancer Lett 112 Jan. 15, 1997 pp. 79–86.

Patent Abstracts of Japan, JP 04 054132 A (Hitachi Ltd), Feb. 21, 1992, Umemura Shinichiro.

Kessel D. et al., "Modes of photodynamic vs. sonodynamic cytotoxicity" Journal of Photochemistry and Photobiology B: Biology, 1995, 28(3), pp. 219–221.

Worthington A.E. et al., "Mechanism of ultrasound enhanced porphyrin cytotoxicity. Part I: A search for free radical effects", Ultrasound Med Biol., 1997, 23(7), pp. 1095–1105.

*Primary Examiner*—Shawna J. Shaw
(74) *Attorney, Agent, or Firm*—Bacon & Thomas

(57) ABSTRACT

A method of treatment of a human or animal body by sonodynamic therapy in which a sensitizer agent is administered to the body and the body is exposed to ultrasound to achieve a cytopathogenic effect at a site therein, wherein the said sensitizer agent is a physiologically tolerable substance which is capable of enhancing the cytopathogenic efficacy of said sonodynamic therapy. Preferably, the sensitizer agent is a water-soluble polymer compound or a conjugate thereof.

14 Claims, 3 Drawing Sheets

U.S. PATENT DOCUMENTS

| | | | | |
|---|---|---|---|---|
| 5,512,268 A | * | 4/1996 | Grinstaff et al. | 424/9.322 |
| 5,576,013 A | * | 11/1996 | Williams et al. | 424/423 |
| 5,633,584 A | * | 5/1997 | Maryanskl et al. | 324/300 |
| 5,733,572 A | * | 3/1998 | Unger et al. | 424/450 |
| 5,775,339 A | * | 7/1998 | Woodburn et al. | 128/898 |
| 5,817,048 A | * | 10/1998 | Lawandy | 604/20 |
| 5,840,276 A | * | 11/1998 | Apfel | 424/9.52 |
| 5,846,530 A | * | 12/1998 | Soon-Shiong et al. | 424/93.7 |
| 5,919,135 A | * | 7/1999 | Lemelson | 600/407 |
| 6,051,207 A | * | 4/2000 | Klaveness et al. | 424/9.1 |
| 6,071,944 A | * | 6/2000 | Rodgers et al. | 514/408 |
| 6,159,445 A | * | 12/2000 | Klaveness et al. | 424/9.6 |
| 6,176,842 B1 | * | 1/2001 | Tachibana et al. | 604/22 |
| 6,233,481 B1 | * | 5/2001 | Lawandy | 600/476 |
| 6,424,857 B1 | * | 7/2002 | Henrichs et al. | 600/431 |

* cited by examiner

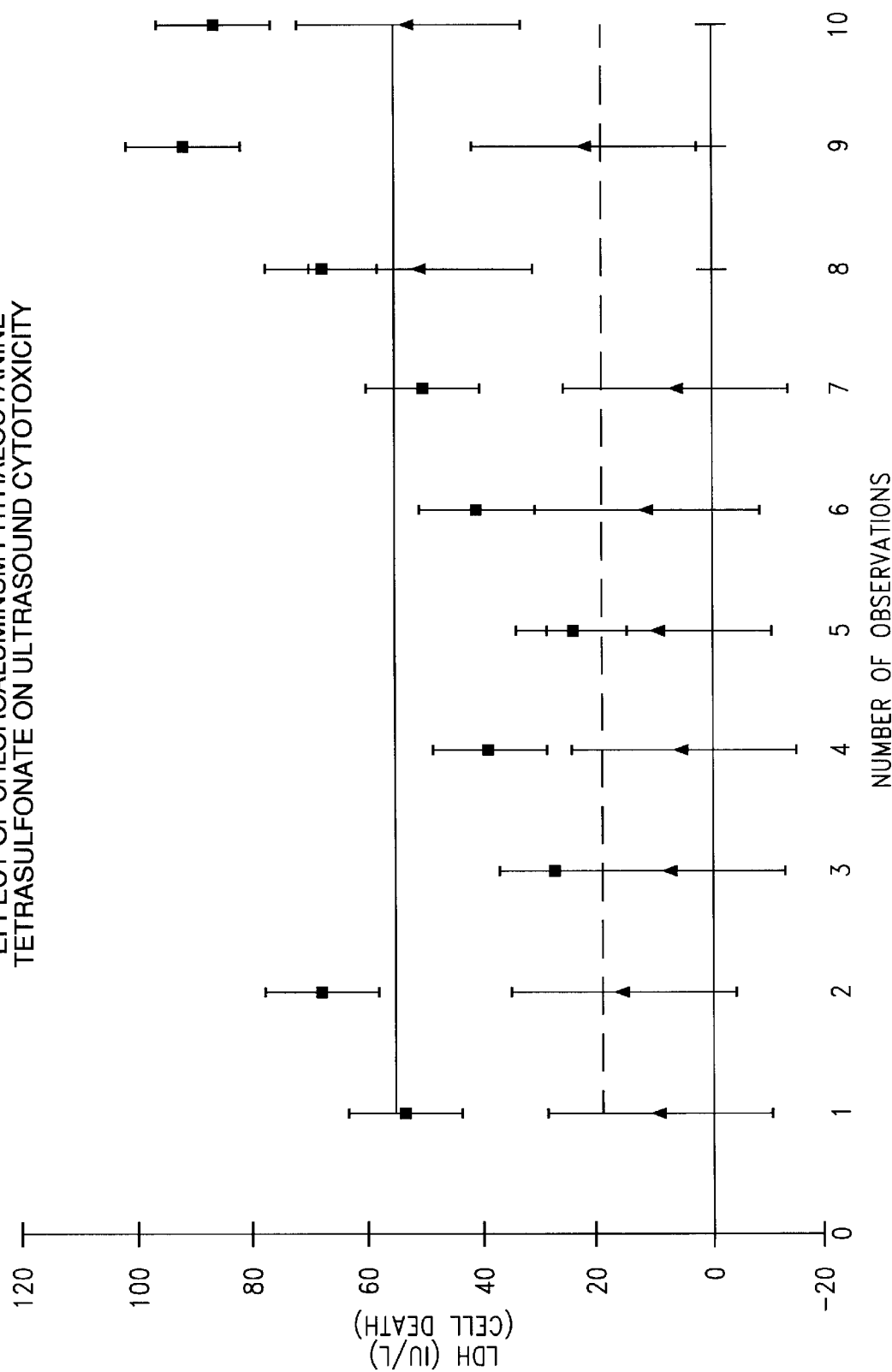

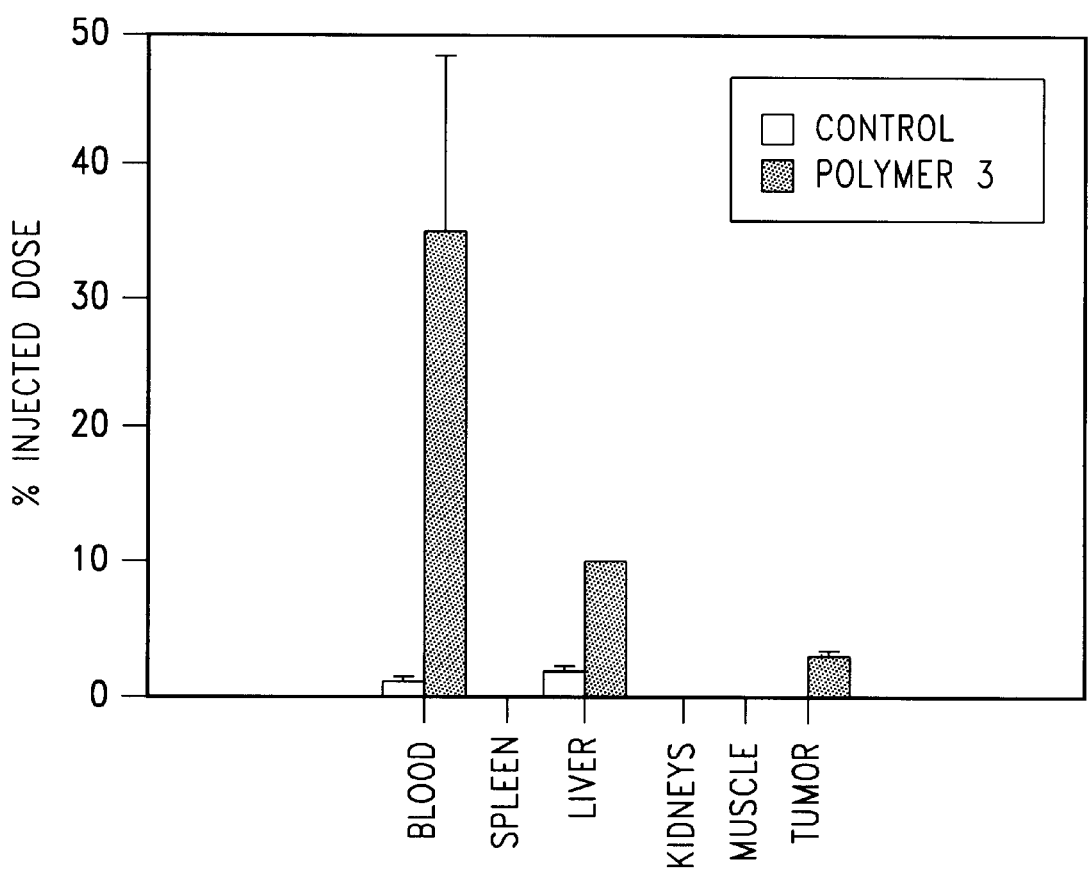

BIODISTRIBUTION OF POLYMER 3 IN FEMALE MICE IMMUNODEFICIENT MICE WITH HT-29 TUMORS THREE HOUR POST-DOSING

SONODYNAMIC THERAPY USING AN ULTRASOUND SENSITIZER COMPOUND

This application is a continuation of pending international application number PCT/GB98/01444 filed May 19, 1998 (of which the entire disclosure of the pending, prior application is hereby incorporated by reference), which itself is a continuation-in-part of U.S. provisional application No. 60/048,487 filed Jun. 3, 1997.

This invention relates to the use of ultrasound-susceptibility modification agents, e.g. water-soluble polymers such as polyalkylene oxides and derivatives thereof, surfactants, oil-in-water emulsions, stabilized particles and certain chromophoric groups such as sulfonated dyes, in methods of treatment of the human or animal body by sonodynamic therapy.

BACKGROUND OF THE INVENTION

The use of dye compounds in photodynamic therapy (PDT) is well established. In PDT, a dye compound, e.g. a porphyrin, which accumulates at a disease site (e.g. a tumor) is administered to the patient whereafter the disease site is illuminated with light of a wavelength absorbed by the dye compound. The resultant localized presence of singlet oxygen destroys cells at the disease site.

Recently it has been found that certain dye compounds, in particular porphyrins, can achieve a similar cytopathogenic effect when the disease site is subjected to ultrasound irradiation. This technique is referred to as sonodynamic therapy (SDT) and is discussed for example by Jeffers et al. in IEEE Ultrasonics Symposium, 1991, pages 1367–1370, Umemura et al. in Ultrasonics Sonochemistry 3: S187–191 (1996), Yumita et al. in Jpn J. Cancer Res. 80: 219–222 (1989), Umemura et al. in Jpn J. Cancer Res. 81: 962–966 (1990), Umemura et al. in Jpn J. Cancer Res. 84: 582–588 (1993), Yumita et al. in Jpn J. Cancer Res. 87: 310–316 (1996), Yumita et al. in Cancer Letters 112: 79–86 (1997), Miyoshi et al. in Radiation Research 143: 194–202 (1995), Kessel et al. in Int. J. Radiat. Biol 66: 221–228 (1994) and Kessel et al in J. Photochem. and Photobiol. B. Biology 28: 219–221 (1995)

SUMMARY OF THE INVENTION

As used herein, the term "sonodynamic therapy agent" is synonymous with "ultrasound-susceptibility modification agent". An effective amount of one or more SDT agent of this invention together with an effective amount of ultrasound acoustic energy, when administered to cells in a human or animal body such as diseased cells and cells that cause disease, is cytopathogenic to those cells. In the absence of said effective amount of sonodynamic therapy agent, the effective amount of ultrasound acoustic energy is substantially non-cytopathogenic to the cells, and in the absence of said effective amount of ultrasound acoustic energy, the effective amount of sonodynamic therapy agent is substantially non-cytopathogenic to the cells.

"Cytopathogenic" is herein meant to include the terms cytotoxic, cytolytic, cytocidal, cytoclastic, cytostatic as well as other descriptors which relate to the onset or potentiation or initiation of cell death, cell fragmentation, cell rupture, cell dormancy, or change in one or more cellular function to effect a change from a diseased to a non-diseased state including from infection to non-infection, relative to the human or animal body.

SDT has an advantage over PDT in that ultrasound penetrates more deeply into the body than the light used in PDT which is rapidly diffused by scattering over millimeter distances.

One aspect of the present invention is based on the realization that certain materials, for example water soluble polymers (e.g. hexamers and higher polymers), in particular polyalkyleneoxide compounds, are also effective sensitizer agents in sonodynamic therapy (SDT).

By a sensitizer agent is meant a material which enhances the cytopathogenic efficacy of the SDT procedure. "Sensitizer agent" herein is synonymous with sonodynamic therapy (SDT) agent. Such an agent may be administered on its own or in combination with other sensitizer agents such as the porphyrin compounds discussed in the literature references listed above.

Thus viewed from one aspect the invention provides a method of treatment of the human or animal body (e.g. a vascularized mammalian, avian or reptilian body) by sonodynamic therapy in which a sensitizer agent is administered to said body and said body is exposed to ultrasound to achieve a cytopathogenic effect at a site (e.g. a tumor site) therein, wherein the said sensitizer agent is a physiologically tolerable substance which is capable of enhancing the cytopathogenic efficacy of said sonodynamic therapy.

The sensitizer agent may be selected from water-soluble polymers and derivatives thereof, surfactants, oil-in-water emulsions, stabilized particles and certain chromophoric groups such as sulfonated dyes. Preferably the sensitizer agent is a water-soluble polymer, such as a polyalkylene oxide, or a derivative thereof. Viewed from a further aspect the invention provides the use of a physiologically tolerable water-soluble polymer compound or a conjugate thereof for the manufacture of a sensitizer composition for use in a method of sonodynamic therapy.

In the method of the invention, the target site for SDT is preferably exposed to ultrasound irradiation before commencement of the SDT as this may facilitate uptake of the sensitizer agent at the target site.

The water-soluble polymer compounds useful as sensitizer agents in accordance with the invention conveniently have a molecular weight of 150 to 1000000 (especially 500 to 500000, most preferably 1000 to 50000), and preferably are hexamers or higher polymers. The polymers preferably contain monomer residues contributing 2 to 6 atoms to the polymer backbone, especially 2, 3 or 4 atoms. Optionally the polymers contain groups which can act as free radical precursors or groups susceptible to oxidation to produce such groups. Particularly preferably the polymers contain ether or hydroxyl groups or groups having heteroatom:heteroatom bonds (for example nitrogen-nitrogen, nitrogen-oxygen or oxygen-oxygen bonds, e.g. peroxide bonds). The polymers may conveniently comprise residues of monomers such as alkylene oxides, hydroxyalkyl-acrylates or methacrylates, vinyl alcohol, vinyl pyrrolidone, acrylamide, styrenes, etc. The polymer compounds are optionally partially oxidized, e.g. being hydroperoxides or peroxides, i.e. carrying pendant groups —OOH or —OOR$^1$ (where R$^1$ is a linear, branched, and/or cyclic alkyl or alkenyl group containing up to 30 carbons or is a hydroxy residue, such as PEG-). The introduction of such groups may frequently be effected by exposure of the polymer to air or oxygen. Peroxy groups may be introduced by treatment with a hydroperoxide in the presence of a metal catalyst such as a salt of cobalt, magnesium, or copper, e.g. cuprous chloride as described by Sosnovsky and Rawlinson (Organic Peroxides Vol. 2, p.153–268, Interscience, New York 1970). The presence of such groups or bonds leads to the compounds functioning as radical precursors, convertible to free radicals under the action of ultrasound irradiation in SDT.

By a conjugate is meant a composition of matter, e.g. a compound or aggregate, which contains a polymeric moiety, preferably a residue of a polymeric compound as described in the previous paragraph, attached to one or more further moieties, e.g. a chromophore, a targeting vector or a reporter moiety. Thus although the polymeric moiety may be conjugated to a chromophore, the polymeric moiety need not itself be a chromophore and simple non-chromophoric non-conjugate (water soluble) polymers may be used to advantage in the method of the invention.

As used herein, a branched polymer is a polyalkylene oxide moiety which contains at least one branching group to which is attached at least one additional polyalkylene oxidyl group.

In one aspect, a branching group in the backbone of the polyalkylene oxide moiety can be selected from the group consisting of a nitrogen atom and a carbon atom. At least one additional polyalkylene oxidyl group can be attached to the branching group by a chemical bond selected from the group consisting of carbon-carbon, carbon-nitrogen, and carbon-oxygen chemical bonds, or by a linking group.

Preferred linking groups to a nitrogen branching group include:

methylene groups, [—$CH_2$—];

poly(methylene) groups, [—($CH_2$)$_n$—] wherein n is an integer from 2 to about 16, such as can be formed by reaction between a nitrogen NH group and an alkylenyl group containing a terminal halide (e.g., Cl, Br, I) or sulfonate group (e.g., methanesulfonate, toluenesulfonate, benzenesulfonate and the like);

alkylenecarbonyl groups [—($CH_2$)$_{n''}$—C(=O)—] wherein n" is an integer from 1 to about 16 such as can be formed by reacting an NH group with a haloalkylenecarbonyl group; ethylenesulfonylethylene groups [—$CH_2CH_2$—S(=O)$_2$—$CH_2CH_2$—], such as can be formed by reacting an NH group with a vinylsulfonylethylene group [$CH_2$=CH—S(=O)$_2$—$CH_2CH_2$—];

ethylenesulfonylmethyleneoxymethylenesulfonylethylene groups [—$CH_2CH_2$—S(=O)$_2$—$CH_2$—O—$CH_2$—S(=O)$_2$—$CH_2CH_2$—], such as can be formed by reacting an NH group with a vinylsulfonylmethyleneoxymethylenesulfonylethylene group [$CH_2$=CH—S(=O)$_2$—$CH_2$—O—$CH_2$—S(=O)$_2$—$CH_2CH_2$—];

ethylenesulfonylmethylenesulfonylethylene groups [—$CH_2CH_2$—S(=O)$_2$—$CH_2$—S(=O)$_2$—$CH_2CH_2$—], such as can be formed by reacting an NH branching group with a vinylsulfonylmethylenesulfonylethylene group [$CH_2$=CH—S(=O)$_2$—$CH_2$—S(=O)$_2$—$CH_2CH_2$—];

carbonyl groups [—(C=O)—] which can comprise an amide linking group formed, for example, by reacting an NH branching group with an activated ester such an N-hydroxysuccinimidyl-ester, or with a mixed anhydride such as a trifluoromethyloxycarbonyl-, or with an acid halide such as an acid chloride, e.g., Cl—(C=O)—;

sulfonyl groups [—S(=O)$_2$—] which can comprise a sulfonamide linking group formed, for example, by reacting an NH branching group with a sulfonyl halide such as a polyalkylene oxidylalkylenesulfonyl chloride, e.g., Cl—S(=O)$_2$—($CH_2$)$_n$—O—PAO; wherein n is an integer from 2 to about 16 and PAO is a polyalkylene oxidyl group;

carbonyloxy groups [—C(=O)—O—] such as those found in urethane groups such as can be obtained by reacting a polyalkyleneoxy group with phosgene and then with an NH group;

thiocarbonyl groups [—(C=S)—] such as those found in thiourethane groups such as can be obtained by reacting a polyalkyleneoxy group with thiophosgene and then with an NH group;

alkylenecarbonyloxymethyleneoxycarbonylalkylene groups [—(—$CH_2$—)$_{n'}$—C(=O)—O—C(R'R")—O—C(=O)—(—$CH_2$—)$_{n'}$—] where each n' is independently selected from the group of integers from 1 to 16 and each R' and R" is independently selected from the group consisting of H and methyl; and carbonylalkylenecarbonyl groups [—C(=O)—($CH_2$)$_w$—C(=O)—] wherein w is an integer from 1 to about 6, such as succinate and adipate.

Preferred linking groups to a carbon branching group include:

ether groups [—O—];
thioether groups [—S—];
thiosulfoxide groups [—S(=O)—];
thiosulfonyl groups [—S(=O)$_2$—];
oxycarbonyl groups [—O—C(=O)—];
aminocarbonyl groups [—NH—C(=O)—];
carbonyl groups [—(C=O)—];
carbonyloxy groups [—C(=O)—O—];
carbonate groups [—O—C(=O)—O—];
carbonyloxymethyleneoxycarbonylalkylene groups [—(—C(=O)—O—C(R'R")—O—C(=O)—(—$CH_2$—)$_{n'}$] where n' is an integer from 1 to 16 and each R' and R" is independently selected from the group consisting of H and methyl; urethane groups [—O—C(=O)—NH—]; and thiourethane groups [—O—(C=S)—NH—].

In another aspect, a branching group can comprise the unit —$NR_1$—$CR_2R_3$—$CR_4R_5$— wherein $R_{1'}$ can be selected from the group consisting of H, an alkyl group of from 1 to about 16 carbon atoms which may be linear, branched, saturated, unsaturated, or contain a carbocyclic ring of from 3 to about 10 carbon atoms, or a carbonylalkyl group wherein the alkyl group is defined immediately above;

$R_{2'}$ and $R_{3'}$ are independently selected from the group consisting of H, an alkylene group of from 1 to about 16 carbon atoms, which may be linear, branched, saturated or unsaturated, and can contain a carbocyclic ring of from 3 to about 10 carbon atoms, and to which is attached a polyalkylene oxidyl group through a heteroatom group selected from the group consisting of NH, O, S, O—C(=O), and C(=O)—O, e.g., such as 4-(polyalkyleneoxyethylcarbonylaminobutyl), [PAO-$CH_2CH_2C$(=O)NH—($CH_2$)$_4$—], 2-(polyalkyleneoxycarbonyl)ethyl, [PAO-C(=O)$CH_2CH_2$—], polyalkyleneoxycarbonylmethyl, [PAO-C(=O)$CH_2$—], polyalkyleneoxyethylaminocarbonylmethyl, [PAO-$CH_2CH_2NHC$(=O)$CH_2$—], polyalkyleneoxyethylaminocarbonylethyl, [PAO-$CH_2CH_2NHC$(=O)$CH_2CH_2$—], and polyalkyleneoxyethylthiomethyl, [PAO-$CH_2CH_2$—S—$CH_2$—];

$R_{4'}$ and $R_{5'}$ are independently selected from the group consisting of H, an alkyl group of from 1 to about 16 carbon atoms which may be linear, branched, saturated, unsaturated, or contain a carbocyclic ring of from 3 to about 10 carbon atoms, or a carbonylalkyl group wherein the alkyl group is defined above, or, preferably, where both $R_4'$ and $R_5'$ are taken together form a carbonyl group;

and wherein at least one of $R_2, R_3'$ is not H.

Preferred units —$NR_1$—$CR_2 R_3$—$CR_4 R_5$— are selected from the group consisting of lysine, aspartic acid, glutamic acid, cysteine, and serine in the backbone of the polyalkylene oxide moiety and contain least one additional polyalkylene oxide attached, for example, to the epsilon amine site of lysine, to the gamma carboxylic acid site of aspartic acid, to the delta carboxylic acid site of glutamic acid, to the beta sulfhydryl group in cysteine, and to the beta hydroxy site of serine.

In another aspect, one branching group and a carbon atom in the backbone of the polyalkylene oxide moiety or two branching groups in the backbone of the polyalkylene oxide moiety can be joined by an alkylene group of from 2 to 12 carbon atoms. The alkylene group can be linear or branched such as ethylene, propylene, butylene, isobutylene, pentylene, hexylene, octylene, decylene, and dodecylene. The alkylene group can be saturated or unsaturated such as 2-butenylidene, isoprenylene, and 2-butynylidene. In another aspect, the alkylene group can comprise a saturated or unsaturated cyclic group such as cyclopropylidene, cyclobutylidene, 1,2-cyclopentylidene, 1,3-cyclopentylidene, 1,2-cyclohexylidene, 1,3-cyclohexylidene, 1,4-cyclohexylidene, a cyclohexenylidene ring such as can be formed by a Diels-Alder reaction between a diene and a dieneophile, 1,4-cycloheylidenebismethylene, ethylene-1,2-cyclopropylidenemethylene, 1,1-spirocycloproylidenebismethylene, and the like, and which can contain an oxygen or sulfur ether atom, such as a 2,5-tetrahydrofuranylene group and a 2,6-tetrahydropyranylene group.

In another aspect, one branching group and a carbon atom in the backbone of the polyalkylene oxide moiety or two branching groups in the backbone of the polyalkylene oxide moiety can be separated by an aromatic ring of 6 to 14 carbon atoms such as p-phenylene, or m-phenylene, or m-toluidene, 9,10-anthracenylidene, or 1,4-naphthalenylidene, or an aralkylene group such as p-phenylenebismethylene, or 9,10-anthracenylidenebismethylene, and which aromatic ring can comprise a 5- or 6-membered heterocyclylene group containing one or two heteroatoms selected from the group consisting of nitrogen, oxygen, and sulfur such a 2,6-pyridinylene, 1,4-imidazolidene, 5,8-quinolinylidene, and 1,1-spiro-2,6-dithiacyclohexylene, or a symmetrical triazinylene group.

Examples of suitable polymers and polymeric moieties include:

polyalkylene oxide polymers and copolymers (including random and block and graft copolymers) and oligomers such as poly(ethylene oxide) also known as poly (ethylene glycol) also known as PEG, as well as poloxamers and poloxamines (also known as Pluronics (CA Registry Number 106392-12-5) and Tetronics (CA Registry Number 110617-70-4)); PEG derivatives such as PEG mono- and bis-ethers of alkyl, alkenyl and alkynyl groups containing from 1 to about 20 carbon atoms and which can be linear or branched and which can comprise a cycloalkyl or cycloalkenyl group with ring size of from 3 to 10 carbons (preferably a cyclohexenyl, cyclooctenyl, or cyclooctadienyl group) such that the total number of carbons in the group is less than 20; PEG mono- and bis-esters (including alpha-methoxy-PEG monoesters) and PEG mono- and bis-amides (including alpha-methoxy-PEG monoamides) of alkyl, alkenyl and alkynyl carboxylic acid groups containing from 1 to about 20 carbon atoms and which can be linear or branched and which can comprise a cycloalkyl or cycloalkenyl group with ring size of from 3 to 10 carbons (preferably a cyclohexenyl, cyclooctenyl or cyclooctadienyl group) such that the total number of carbons in the group is less than 20;

hydroperoxides and alkyl and alkenyl peroxides of PEG and derivatives of PEG wherein alkyl and alkenyl are as described above, and which comprise a content of hydroperoxide (structurally described as —O—CH(OOH)—$CH_2$—) or peroxide (structurally described as —O—CH($OOR^1$)—$CH_2$— where $R^1$ is alkyl or alkenyl as described above) which can range from as small as one unit of hydroperoxide or peroxide per polymer molecule up to about 15 per cent of the monomer units of the polymer being hydroperoxides or peroxides or mixtures of both hydroperoxides and peroxides;

PEG derivatives and peroxide and hydroperoxide derivatives of PEG as described above conjugated to a polyiodinated aromatic compound, e.g. PEG esters and amides of mono, di, and tri-iodinated aromatic benzoic acid derivatives such as diatrizoic acid esters and amides;

poly(propylene glycol) (PPG, also known as poly (propylene oxide)) and PPG derivatives and PEG-PPG random and preferably block copolymers and their hydroperoxides (structurally described as —O—CH(OOH)—$CH_2$— when the hydroperoxide is part of the PEG and —O—C($CH_3$)(OOH)—$CH_2$— and also —O—CH($CH_3$)—CH(OOH)— when the hydroperoxide is part of the PPG) and peroxides (structurally described as —O—CH($OOR^1$)—$CH_2$— when the peroxide is part of the PEG and —O—C($CH_3$)(OOR)—$CH_2$— and also —OCH($CH_3$)—CH(OOR)— when the peroxide is part of the PPG where $R^1$ is alkyl or alkenyl as described above); poly(hydroxyalkyl) acrylates and methacrylates and their hydroperoxides and peroxides; polyvinyl alcohol and its hydroperoxides and peroxides;

polyvinylpyrrolidone and its hydroperoxides and peroxides;

polyacrylamide and its hydroperoxides and peroxides;

water soluble polystyrenes and their hydroperoxides and peroxides, including sulfonated polystyrene, hydroxyalkylated and polyhydroxyalkylated polystyrene, and PEG ethers and esters of hydroxyalkylated and polyhydroxyalkylated polystyrene;

surfactants comprising PEG and hydroperoxides and peroxides of PEG, such as Pluronics (e.g. Pluronic F-108 from BASF) that have been oxidized by the action of oxygen in air.

The polymeric compounds may be homo- or copolymers, and where copolymers may be random, block or graft, and may contain individual comonomer residues such as the diamine residues in the poloxamine polymers. Polyalkyleneoxide polymers are especially preferred.

In another embodiment, a preferred physiologically tolerable SDT agent of this invention is a surfactant molecule.

In this invention, a surfactant molecule is defined as an emulsifier or detergent as listed in McCutcheon's Directories, Volume 1: Emulsifiers and Detergents (1994), and which contains at least one chemical functional group selected from the group consisting of an alcohol (OH), a nitrilo group including a primary amine ($NH_2$) and a secondary amine (NH), a carboxylic acid (COOH), a sulfhydryl (SH), a phosphoric acid group, phosphonic acid group, a phenolic group, a sulfonic acid group, a carbon-carbon double bond, and a ketone.

Accordingly, there is provided a method of treatment of the human or animal body by sonodynamic therapy in which a sensitizer agent is administered to said body and said body is exposed to ultrasound to achieve a cytopathogenic effect at a site therein, wherein the sensitizer agent is a surfactant compound containing at least one chemical functional group selected from the group consisting of an alcohol (OH), a nitrilo group including a primary amine ($NH_2$) and a secondary amine (NH), a carboxylic acid (COOH), a sulfhydryl (SH), a phosphoric acid group, phosphonic acid group, a phenolic group, a sulfonic acid group, a carbon-carbon double bond, and a ketone.

In a further aspect of the invention, there is provided the use of physiologically tolerable surfactant compound for the manufacture of a sensitizer composition for use in sonodynamic therapy, wherein the surfactant compound contains at least one chemical functional group selected from the group consisting of an alcohol (OH), a nitrilo group including a primary amine ($NH_2$) and a secondary amine (NH), a carboxylic acid (COOH), a sulfhydryl (SH), a phosphoric acid group, phosphonic acid group, a phenolic group, a sulfonic acid group, a carbon-carbon double bond, and a ketone.

Chemical functional groups in the surfactant molecules can be interconverted by chemical reactions well known to those skilled in the art. For example, a hydroxyl group can be converted to a methanesulfonic acid ester which can be treated with sodium azide and reduced to form an amine group. Carboxylic acid groups and ketones can be reduced to form alcohols, and alcohols can be oxidized to form ketones, aldehydes, and carboxylic acid groups.

Useful surfactant molecules are emulsifiers or detergents which can function as dispersing agents, wetting agents, adsorbents, anticaking agents, soil antiredispositioning agents, antistats, binders, carriers, pearlescents, conditioning agents, hydrotropes, defoamers, emollients, flocculants, humectants, lubricants, opacifiers, plasticizers, preservatives, release agents, scale inhibitors, stabilizers, suspending agents, thickeners, UV absorbers, water repellants, waxes, and polishes, and which contain at least one chemical functional group selected from the group consisting of an alcohol (OH), a nitrilo group including a primary amine ($NH_2$) and a secondary amine (NH), a carboxylic acid (COOH), a sulfhydryl (SH), a phosphoric acid group, a phosphonic acid group, a phenolic group, a sulfonic acid group, a carbon-carbon double bond, and a ketone.

Preferably, the surfactant molecule comprises a polyalkyleneoxide moiety, optionally containing a branching group as defined herein; more preferably a polyalkyleneoxide block copolymeric moiety, optionally containing a branching group as defined herein; and most preferably a polyalkyleneoxide block copolymeric moiety optionally containing a branching group as defined herein and comprising a polypropylene oxide block and a polyethyleneoxide block. Examples of useful surfactant molecules include block copolymers such as AL 2070 available from ICI Surfactants, Antarox block copolymers available from Rhone-Poulenc, Delonic block copolymers available from DeForest, Inc., Hartopol block copolymers available from Texaco Chemical Canada, Macol block copolymers available from PPG Industries, Marlox block copolymers available from Huls America, Pluronic block copolymers including Pluronic F, L, P and R available from BASF Corp., Poly-Tergent block copolymers available from Olin Corp., and Tetronic and Tetronic R block copolymers available from BASF Corp. Currently preferred surfactant molecules include Tetronic and Pluronic block copolymers, and currently most preferred are Tetronic block copolymers.

Polyalkyleneoxide compounds are readily available commercially, e.g. as Pluronics, Tetronics or PEGs of various molecular weights.

The polyalkyleneoxides may contain a polyalkylenoxide moiety (e.g. a moiety of formula $((X)_nO)_p$, where X is an alkylene group (e.g. a $C_{2-4}$ alkylene) and n and p are positive integers, optionally incorporating an alkylene-amino or alkylenediamino group) and may consist simply of such a moiety terminated by simple functional groups, e.g. hydroxyl, amine, phosphate and phosphonate groups.

The conjugates of the compounds used according to the invention may contain other moieties covalently bonded together, e.g. chromophores, lipophilic groups, biotargetting vector groups, and groups detectable in in vivo diagnostic imaging modalities such as for example MR and X-ray (e.g. CT) imaging.

Examples of other groups the hydrophilic polymer entities may be conjugated to include free radical precursors. Thus, for example, the conjugates may be compounds of formula $PAO\text{-}C_6H_4\text{—}CHR'R''$ or $PAO\text{-}O\text{—}CH_2CH\text{=}CH_2$, where PAO is a polyalkylene oxide moiety (e.g. PEG), R' is H or aryl, and R" is aryl (where aryl implies any substituted or unsubstituted, homo- or heterocyclic, mono- or polycyclic aryl group, e.g. mono- or bicyclic aryl groups optionally containing 1, 2 or 3 ring heteroatoms selected from O, N and S).

Where a water soluble polymer moiety is part of a larger molecular structure, the overall molecule may contain a single water soluble polymer moiety (e.g. as a pendant or terminal group or as a linker group between two other moieties) or it may contain a plurality (i.e. 2 or more) of such moieties, e.g. as pendant or terminal groups or as linker groups, for example linking the chromophore groups in a polychromophore compound.

In a particularly preferred embodiment of the invention the sensitizer compound contains a reporter moiety (R) which is detectable in an in vivo diagnostic imaging modality, and optionally a vector moiety ($V_c$) which serves to modify the biodistribution of the sensitizer compound, e.g. by prolonging the blood residence time of the compound or by actively targetting the compound to particular body sites, e.g. disease sites or other proposed sites for SDT. In this way, using the appropriate imaging modality the reporter moiety may facilitate location of treatment sites for SDT. This combination of imaging and therapy is new and forms a further aspect of the invention. Viewed from this aspect the invention provides a method of treatment of the human or animal body (e.g. a vascularized mammalian, avian or reptilian body) by sonodynamic therapy in which a sensitizer agent is administered to said body and said body is exposed to ultrasound to achieve a cytopathogenic effect at a site (e.g. a tumor site) therein, wherein the said sensitizer agent is a physiologically tolerable conjugate comprising a hydrophilic polymer moiety and a reporter moiety detectable in an in vivo diagnostic imaging modality and using said modality to generate an image of at least part of said body to which said conjugate distributes, e.g. to locate sites for irradiation by ultrasound in the sonodynamic therapy or to follow the progress of sonodynamic therapy of a site within said body.

In this method, any suitable imaging modality may be used, e.g. X-ray, MRI, ultrasound, light imaging, scintigraphy, in vivo microsopy such as confocal, photoacoustic imaging and acousto-optical imaging and visual observation and photographic imaging, magnetotomography, or electrical impedance tomography; however, X-ray, MRI, ultrasound, light imaging and scintigraphy (especially X-ray, MRI and ultrasound) are preferred.

Viewed from a further aspect the invention provides the use of a physiologically tolerable conjugate comprising a hydrophilic polymer moiety and a reporter moiety detectable in in vivo diagnostic imaging for the manufacture of a composition for use in a method of treatment by SDT.

The choice of reporter moiety used will of course depend on the choice of imaging modality. For X-ray imaging, the reporter will preferably be a heavy atom (atomic number greater than 37), e.g. a covalently attached species such as iodine, a chelated heavy metal ion or complex ion, or a particulate substance such as a heavy metal compound, an insoluble iodinated organic compound or a vesicle enclosing an iodinated organic compound or a heavy metal compound. Iodinated organic compounds are especially preferred.

For MRI, the reporter will preferably be a paramagnetic, superparamagnetic, ferromagnetic or ferrimagnetic material, e.g. a chelated transition metal or lanthanide ion (such as Gd, Dy, Mn or Fe) or a superparamagnetic metal oxide particle. Again such materials may be bound directly to the rest of the sensitizer or may be entrapped within a vesicle which is bound to the rest of the sensitizer.

For ultrasound imaging, which is particularly preferred because the imaging and therapy may be effected by the same or similar apparatus, the reporter is preferably a particulate substance bound to the rest of the sensitizer, e.g. a vesicle (e.g. a liposome, micelle or microballoon) enclosing an echogenic contrast agent such as a gas or gas-precursor (a material which is gaseous at 37° C.) or a mixture thereof. As echogenic materials, particular mention may be made of perfluoroalkanes such as perfluoropentane and perfluorobutane.

Ultrasound reporters are of course highly preferred in view of the use of ultrasound in the therapeutic treatment—thus SDT with an ultrasound reporter-labelled sensitizer (or with an ultrasound contrast agent) may allow for simultaneous treatment and imaging using the same ultrasound irradiation.

For scintigraphy, the reporter will generally be a covalently bound non-metal radionuclide (e.g. an iodine isotope) or a chelated metal radionuclide.

For light imaging the reporter is a chromophore (the term chromophore being used herein to cover structures which absorb light at 300–1300 nm, preferably 600 to 1300 nm) and includes fluorophores and phosphorescent materials) and/or a light scatterer, e.g. a particulate with or without associated chromophores.

Examples of suitable chromophores include: porphyrins such as hematoporphyrins, dihematoporphyrin ester, hematoporphyrin dimethyl ether, Photohem(e), polyhematoporphyrin, benzoporphyrin derivatives (e.g. BPD, BPD-MA mono-acid ring, verteporfin), metallo-tetrabenzoporphyrins, meso-tetrahydroxyphenylporphine (mTHPP), and also ortho- and para-forms, fluorinated THPP, meso-tetra-(4-carboxyphenyl)porphine, lutetium texaphyrin (LuTex, PCL-0123), meso-(2-cyanovinyl) porphyrins, dimethoxyhematoporphyrin IX (DMHp), meso-tetraphenylporphine tetrasulfonate ($TPPS_4$), 9-acetamido-2,7,12,17-tetra-n-propylporphycene (AamTPPn), 9-acetoxy-2,7,12,17-tetrakis-($\beta$-methoxyethyl)-porphycene (ATMPn), glycoconjugated porphyrins, uroporphyrin III/Coproporphyrin III (natural), protoporphyrin IX induced by 5-ALA, vinyl porphyrins derived from deuteroporphyrin, hydroxyoctaethylporphyrin, tribenzonaphtho- and trinaphthobenzoporphyrazines, di- and tetrahydroporphyrins, tetrapyrrols, boronated porphyrin (BOPP), cationic porphyrins; phthalocyanines and naphthalocyanines such as zinc phthalocyanine, chloroaluminum sulfonated phthalocyanine (CASPc), phosphonated phthalocyanine derivatives, phthalocyanine immunoconjugates, Si-phthalocyanines and Si-naphthalocyanines (e.g. isoBOSINC), aluminum phthalocyanine tetrasulfonate (AlPcS4, Photosens(e)), aluminum phthalocyanine di- and trisulfonate ($AlPcS_2$, $AlPcS_3$), zinc naphthalocyanine (tetrabenzylamidotetranaphthoporphyrazinozinc ), pyridinium phthalocyanine (PPc), cationic phthalocyanines; chlorins such as meso-tetra-hydroxyphenyl bacteriochlorin (mTHPBC), bacteriochlorin $\alpha$ (BCA), meso-tetrahydroxyphenyl chlorin (mTHPC, Temoporfin, Foscan), Si, Ga, etc. When this element is tri- or tetravalent, the PEG group may be substituted on this element, directly or using suitable linker groups, as well as or instead of on the aromatic rings. As before, dye$(PEG)_n$ and dye-PEG-dye derivatives are included.

Particularly preferably the reporter is provided by a cyanine, merocyanine, phthalocyanine, naphthalocyanine or a linear cyanine analog chromophore, including squarylium and croconium dyes, especially a chromophore having an extensive delocalized n electron system in which aromatic structures are linked via an unsaturated carbon chain (e.g. one including the structure —CH=CH—CH=), for example a cyanine or linear cyanine analog. It is also particularly preferred that the sensitizer be a polychromophore, i.e. that it contain at least two chromophores. In this regard it is particularly convenient for the chromophores to be linked together by groups incorporating a soluble (i.e. hydrophilic) polymer moiety.

For magnetotomography, the reporter may be a material as described for MR reporters herein, especially a chelated lanthanide or a superparamagnetic metal oxide.

For electrical impedance tomography, the reporter is preferably a polyelectrolyte.

In this method of the invention, imaging may be effected in a conventional fashion and using conventional imaging apparatus for the selected imaging modality. The reporter-containing sensitizer agent in this method is administered in a contrast-enhancing dose, e.g. a dose conventional for the selected imaging procedure, or at a lower than conventional dose where the agent is administered near the target site for SDT or where it is actively targetted to the target site by a vector mTHPC bacteriochlorin derivative, fluorinated THPC, mono-L-aspartyl chlorin (ME2906, NPE-6, Chlorin e6, Cle6), functionalized benzochlorins, N-alkylated chlorins, amphiphilic chlorins, 3-desvinyl-3-formyl-chlorin, (Chlorin p6), 4-formyloxymethylidene-3-hydroxyl-2-vinyl-deuterio-porphynyl-6,7-biaspartic acid (Photochlorin ATX-S10), cyanopurpurins, tin etiopurpurin, (bacterio-)purpurin-18; and others such as hypericin, Rhodamine-6G-chloride, (hydroxy-) bacteriopheophorbide-a-methylester (OH-BPME), pyropheophorbides, pheophorbide-a/methyl-pheophorbide, boron difluorides JM2929, Rose Bengal (xanthene deriv.) with quencher groups, $\delta$-amino levulinic acid (5-ALA), $\delta$-amino levulinic ester or amide, heptanitrosyl-tri-$\mu$-thiotetraferrate, PH-1126, HAT-D01, azo-dyes, cyanine dyes, including indocyanine green (ICG) and derivatives, diarylmethane dyes, including Michler's hydrol blue, auramine, acriflavine, thiopyronine, pyronine G, and including analogs such as Bindschedler's green, thionine, oxonine, triarylmethane dyes, including malachite green, crystal violet, Victoria blue, erythrosine B, rhodamine 123 and all rhodamines, cationic dyes, including toluidine blue, Nile blue, Taylor's Blue, methylene green, new methylene green, azures A, B and C, kryptocyanines (EDKC), benzophenoxazines, benzothiazines, chalkogenapyryliums, merocyanine dyes, such as Merocyanine 540, cytochrome C, and PEG or other hydrophilic derivatives of any of these, including also methylene blue, fluorescein, rose bengal, tetracycline, neutral red and acridine orange. This includes dye(PEG)$_n$ (n=1-10) or dye-PEG-dye type derivatives. Also included are phthalocyanines (Pc's) and naphthalocyanines (Nc's) substituted with PEG or other hydrophilic groups on the aromatic rings, either directly or as derivatives such as PEG carboxamides or sulfonamides. The Pc's or Nc's may optionally contain at their center the atom of an element such as Zn, Al, moiety.

The sensitizer compound may if desired include a vector moiety which serves to modify its biodistribution. Examples of suitable vectors include antibodies, antibody fragments, proteins and oligopeptides which have affinity for cell surface receptors, especially receptors associated with surfaces of diseased or rapidly proliferating cells, and peptidic and non-peptidic drugs which are preferentially taken up by diseased or rapidly proliferating cells.

The sensitizer compound may itself have some vector effect prolonging blood residence, especially where the sensitizer is or incorporates a particle.

Generally, when the sensitizer agent comprises one or more hydrophilic polymer moiety, to achieve a blood residence prolonging effect, the total molecular weight of the hydrophilic polymer moiety or moieties (e.g. polyalkylene oxide moieties such as PEG) should be at least 3400, preferably at least 10000, and more preferably at least 20000.

Molecular weight (MW) refers to a weight average. The term "molecular weight", as used for polymers of this invention, refers to the average molecular weight of the polymer measured by size exclusion chromatography, using narrow molecular weight poly(ethyleneoxide) or poly(ethyleneglycol) standards supplied by American Polymer Standards Corporation as references.

Reporter and vector groups and the manner in which they may be coupled together and to the polymer moiety are discussed in further detail below.

In a particularly preferred embodiment of the invention, the sensitizer compound includes a lipophilic group, preferably a pendant or terminal group, and especially preferably a group capable of association with cellular membranes. Particularly preferably the lipophilic group is or has a linear, optionally unsaturated, $C_{8-40}$ alkyl chain, especially preferably a $C_{12-23}$ unsaturated alkyl chain. The lipophilic group is especially preferably a double ester Y—COO—Z—COO— where Y is a $C_{12-25}$ alkyl group and Z is a $C_{12-25}$ alkylene group, e.g. a group $CH_3(CH_2)_{16}COO(CH_2)_{17}COO$—. The lipophilic group may be attached directly to a water soluble (i.e. hydrophilic) polymer moiety, as in the compound P79 referred to in the Examples below, or the two may be coupled indirectly, e.g. by covalent attachment to different sites on an organic chromophore or to different surface sites of a particulate component of the sensitizer. The inclusion of the lipophilic group is thought to promote association of the sensitizer with cell membranes at the target site for SDT and to potentiate the cytopathogenic effect of the ultrasound irradiation on the cells so associated, perhaps by weakening the cell membrane.

In a particularly novel aspect of the invention, the ultrasound irradiation of the SDT may be used to "switch" a contrast agent for a diagnostic imaging modality between states having different contrast efficacy, i.e. such that the images with and without ultrasound irradiation are different. Such differences will highlight the region of SDT, for example enabling the physician to detect the margins of a tumor or to follow the progress of SDT. Images may be generated with and without the SDT irradiation and if desired a difference image may be produced to pick out areas in which SDT enhancement of the image is occurring. Such switching may be achieved for example where the contrast agent, optionally a sensitizer according to the invention, is sonoluminescent, in which case the imaging modality will be a light imaging technique, or where it is a free radial precursor which is converted to a free radical by the ultrasound irradiation effects, and in this case the imaging modality will be one where radicals have a contrast effect, e.g. MRI, OMRI or esr imaging.

Thus viewed from a further aspect the invention provides a method of generating an image of a human or non-human body which method comprises administering to said body a physiologically tolerable material and using an in vivo diagnostic imaging modality to generate an image of at least a part of said body to which said material distributes, wherein during at least part of the image generation procedure said body is subjected to an ultrasound irradiation sufficient to alter the contrast effectiveness of said material in said imaging modality.

In such a method, the material used as the contrast agent may be a polymer or conjugate as used as an SDT sensitizer as described herein or a chromophore or other reporter as described herein, optionally attached to a vector moiety or a lipophilic group.

Viewed from a still further aspect the invention provides the use of a physiologically tolerable material the contrast effectiveness whereof in a chosen imaging modality is altered by exposure to ultrasound for the manufacture of a composition for use in a method of treatment or diagnosis which involves administration of said composition to a body and generating an image while during at least part of the image generation procedure subjecting said body to an ultrasound irradiation sufficient to alter the contrast effectiveness of said material.

This imaging method moreover may provide information as to local physiological conditions, e.g. pH, oxygen concentration, presence of free radicals, etc. as far as these affect the stability of the "switched" contrast agent. Such information might indicate that the patient would benefit from administration of vasodilators or oxygen to increase tumor oxygenation before beginning the therapeutic SDT procedure. During the procedure, this signal may indicate that the tumor has become deoxygenated, prompting the physician to cease therapy for a brief period of time to allow the tumor to re-oxygenate. Of course, this technique could be extended to cover almost any chemical or physiological state required to enhance cytopathogenicity of the technique.

No diagnostic modalities derived from sonodynamic interactions have previously been reported. The information contained in the derived signal could be presented to the practitioner as either a numerical value corresponding to prespecified ranges, or when used with focused ultrasound techniques, the signal could be mapped onto x, y, and z coordinates and displayed as an image.

Reporters

As mentioned above, the sensitizers used according to the invention, and the contrast agents used in the imaging techniques of the invention, preferably contain at least one reporter moiety, preferably a chromophore. Examples of suitable reporters and means for their attachment to hydrophilic polymer moieties, vector moieties and lipophilic groups are discussed below.

Besides chromophores, the reporter moieties in the sensitizers or contrast agents of the invention may be any moiety capable of detection either directly or indirectly in an in vivo diagnostic imaging procedure, e.g. moieties which emit or may be caused to emit detectable radiation (e.g. by radioactive decay, spin resonance excitation, etc.), moieties which affect local electromagnetic fields (e.g. paramagnetic, superparamagnetic, ferrimagnetic or ferromagnetic species), moieties which influence the spin relaxation of protons and other chemical species in the body, moieties which absorb or scatter radiation energy (e.g. particles (including gas or liquid containing vesicles), heavy elements and compounds thereof, etc.), and moieties which generate a detectable substance (e.g. gas microbubble generators), etc.

A very wide range of materials detectable by diagnostic imaging modalities is known from the art and the reporter will be selected according to the imaging modality to be used. Thus for example for ultrasound imaging an echogenic material, or a material capable of generating an echogenic material will normally be selected, for X-ray imaging the reporter will generally be or contain a heavy atom (e.g. of atomic number 38 or above), for MR imaging the reporter will either be a non zero nuclear spin isotope (such as $^{19}F$) or a material having unpaired electron spins and hence paramagnetic, superparamagnetic, ferrimagnetic or ferromagnetic properties, for light imaging the reporter will be a light scatterer (e.g. a coloured or uncoloured particle), a light absorber or a light emitter, for magnetometric imaging the reporter will have detectable magnetic properties, for electrical impedance imaging the reporter will affect electrical impedance and for scintigraphy, SPECT, PET etc. the reporter will be a radionuclide.

Examples of suitable reporters are widely known from the diagnostic imaging literature, e.g. magnetic iron oxide particles, gas-containing vesicles, chelated paramagnetic metals (such as Gd, Dy, Mn, Fe etc.). See for example U.S. Pat. No. 4,647,447, PCT/GB97/00067, U.S. Pat. Nos. 4,863,715, 4770183, WO96/09840, WO85/02772, WO92/17212, PCT/GB97/00459., EP-A-554213, U.S. Pat. No. 5,228,446, WO91/15243, WO93/05818, WO96/23524, WO96/17628, U.S. Pat. No. 5,387,080, WO95/26205, GB9624918.0, etc.

Particularly preferred as reporters are: chelated paramagnetic metal ions such as Gd, Dy, Fe, and Mn, especially when chelated by macrocyclic chelant groups (e.g. tetraazacyclododecane chelants such as DOTA, DO3A, HP-DO3A and analogues thereof) or by linker chelant groups such as DTPA, DTPA-BMA, EDTA, DPDP, etc; metal radionuclide such as $^{90}Y$, $^{99m}Tc$, $^{111}In$, $^{47}Sc$, $^{67}/Ga$, $^{51}Cr$, $^{177m}Sn$, $^{67}Cu$, $^{167}Tm$, $^{97}Ru$, $^{188}Re$, $^{177}Lu$, $^{199}Au$, $^{203}Pb$ and $^{141}Ce$; superparamagnetic iron oxide crystals; chromophores and fluorophores having absorption and/or emission maxima in the range 300–1400 nm, especially 600 nm to 1200 nm, in particular 650 to 1000 nm; vesicles containing fluorinated gases (i.e. containing materials in the gas phase at 37° C. which are fluorine containing, e.g. $SF_6$ or perfluorinated $C_{1-6}$ hydrocarbons or other gases and gas precursors listed in PCT/GB97/00459); chelated heavy metal cluster ions (e.g. W or Mo polyoxoanions or the sulphur or mixed oxygen/sulphur analogs); covalently bonded non-metal atoms which are either high atomic number (e.g. iodine) or are radioactive, e.g. $^{123}I$, $^{131}I$, etc. atoms; iodinated compound containing vesicles; etc.

Stated generally, the reporter may be (1) a chelatable metal or polyatomic metal-containing ion (i.e. TcO, etc), where the metal is a high atomic number metal (e.g. atomic number greater than 37), a paramagentic species (e.g. a transition metal or lanthanide), or a radioactive isotope, (2) a covalently bound non-metal species which is an unpaired electron site (e.g. an oxygen or carbon in a persistent free radical), a high atomic number non-metal, or a radioisotope, (3) a polyatomic cluster or crystal containing high atomic number atoms, displaying cooperative magnetic behaviour (e.g. superparamagnetism, ferrimagnetism or ferromagnetism) or containing radionuclides, (4) a gas or a gas precursor (i.e. a material or mixture of materials which is gaseous at 37° C.), or (5) a structure or group having electrical impedance varying characteristics, e.g. by virtue of an extensive delocalized electron system.

Examples of particular preferred reporter groups are described in more detail below.

Chelated metal reporters: metal radionuclides, paramagnetic metal ions, fluorescent metal ions, heavy metal ions and cluster ions Preferred metal radionuclides include 90Y, $^{99m}TC$, $^{111}In$, $^{47}Sc$, $^{67}Ga$, $^{51}Cr$, $^{177m}Sn$, $^{67}Cu$, $^{167}Tm$, $^{97}Ru$, $^{188}Re$, $^{177}Lu$, $^{199}Au$, $^{203}Pb$ and $^{141}Ce$.

Preferred paramagnetic metal ions include ions of transition and lanthanide metals (e.g. metals having atomic numbers of 6 to 9, 21–29, 42, 43, 44, or 57–71), in particular ions of Cr, Vanadium, Mn, Fe, Co, Ni, Cu, La, Ce, Pr, Nd, Pm, Sm, Eu, Gd, Tb, Dy, Ho, Er, Tm, Yb and Lu, especially of Mn, Cr, Fe, Gd and Dy, more especially Gd.

Preferred fluorescent metal ions include lanthanides, in particular La, Ce, Pr, Nd, Pm, Sm, Eu, Gd, Tb, Dy, Ho, Er, Tm, Yb, and Lu. Eu is especially preferred.

Preferred heavy metal-containing reporters may include atoms of Mo, Bi, Si, and W, and in particular may be polyatomic cluster ions (e.g. Bi compounds and W and Mo oxides) as described in WO91/14460, WO92/17215, WO96/40287, and WO96/22914.

The metal ions are desirably chelated by chelant groups on a linker moiety or in or on a particle, (e.g. a vesicle or a porous or non-porous inorganic or organic solid), in particular linear, macrocyclic, terpyridine and $N_2S_2$ chelants, such as for example DTPA, DTPA-BMA, EDTA, DO3A, TMT. Further examples of suitable chelant groups are disclosed in U.S. Pat. No. 4,647,447, WO89/00557, U.S. Pat. Nos. 5,367,080, 5,364,613, etc.

The linker moiety or the particle may contain one or more such chelant groups, if desired metallated by more than one metal species (e.g. so as to provide reporters detectable in different imaging modalities).

Particularly where the metal is non-radioactive, it is preferred that a polychelant linker or particulate reporter be used.

A chelant or chelating group as referred to herein may comprise the residue of one or more of a wide variety of chelating agents that can complex a metal ion or a polyatomic ion (e.g. TcO).

As is well known, a chelating agent is a compound containing donor atoms that can combine by coordinate bonding with a metal atom to form a cyclic structure called a chelation complex or chelate. This class of compounds is described in the Kirk-Othmer Encyclopedia of Chemical Technology, Vol. 5, 339–368.

The residue of a suitable chelating agent can be selected from polyphosphates, such as sodium tripolyphosphate and hexametaphosphoric acid; aminocarboxylic acids, such as ethylenediaminetetraacetic acid, N-(2-hydroxy)

ethylenediaminetriacetic acid, nitrilotriacetic acid, N,N-di(2-hydroxyethyl)glycine, ethylenebis(hydroxyphenylglycine) and diethylenetriamine pentacetic acid; 1,3-diketones, such as acetylacetone, trifluoroacetylacetone, and thenoyltrifluoroacetone; hydroxycarboxylic acids, such as tartaric acid, citric acid, gluconic acid, and 5-sulfosalicylic acid; polyamines, such as ethylenediamine, diethylenetriamine, triethylenetetraamine, and triaminotriethylamine; aminoalcohols, such as triethanolamine and N-(2-hydroxyethyl)ethylenediamine; aromatic heterocyclic bases, such as 2,2'-diimidazole, picoline amine, dipicoline amine and 1,10-phenanthroline; phenols, such as salicylaldehyde, disulfopyrocatechol, and chromotropic acid; aminophenols, such as 8-hydroxyquinoline and oximesulfonic acid; oximes, such as dimethylglyoxime and salicylaldoxime; peptides containing proximal chelating functionality such as polycysteine, polyhistidine, polyaspartic acid, polyglutamic acid, or combinations of such amino acids; Schiff bases, such as disalicylaldehyde 1,2-propylenediimine; tetrapyrroles, such as tetraphenylporphin and phthalocyanine; sulfur compounds, such as toluenedithiol, meso-2,3-dimercaptosuccinic acid, dimercaptopropanol, thioglycolic acid, potassium ethyl xanthate, sodium diethyldithiocarbamate, dithizone, diethyl dithiophosphoric acid, and thiourea; synthetic macrocyclic compounds, such as dibenzo[18]crown-6, $(CH_3)_6$—[14]-4, 11-diene-$N_4$, and (2.2.2-cryptate); phosphonic acids, such as nitrilotrimethylene-phosphonic acid, ethylenediaminetetra(methylenephosphonic acid), and hydroxyethylidenediphosphonic acid, or combinations of two or more of the above agents. The residue of a suitable chelating agent preferably comprises a polycarboxylic acid group and preferred examples include: ethylenediamine-N,N,N',N'-tetraacetic acid (EDTA); N,N,N',N'',N''-diethylene-triaminepentaacetic acid (DTPA); 1,4,7,10-tetraazacyclododecane-N,N',N'',N'''-tetraacetic acid (DOTA); 1,4,7,10-tetraazacyclododecane-N,N',N''-triacetic acid (DO3A); 1-oxa-4,7,10-triazacyclododecane-N,N',N''-triacetic acid (OTTA); trans (1,2)-cyclohexanodiethylene-triamine-pentaacetic acid (CDTPA).

Other suitable residues of chelating agents comprise proteins modified for the chelation of metals such as technetium and rhenium as described in U.S. Pat. No. 5,078,985, the disclosure of which is hereby incorporated by reference.

Suitable residues of chelating agents may also derive from $N_3S$- and $N_2S_2$-containing compounds, as for example, those disclosed in U.S. Pat. Nos. 4,444,690; 4,670,545; 4,673,562; 4,897,255; 4,965,392; 4,980,147; 4,988,496; 5,021,556 and 5,075,099.

Other suitable residues of chelating are described in PCT/US91/08253, the disclosure of which is hereby incorporated by reference.

Preferred chelating groups and residues of chelating groups are selected from the group consisting of 2-aminomethylpyridine, iminoacetic acid, iminodiacetic acid, ethylenediaminetetraacetic acid (EDTA), diethylenetriaminepentaacetic acid (DTPA), 1,4,7,10-tetraazacyclododecane-1,4,7,10-tetraacetic acid (DOTA), carbonyliminodiacetic acid, methyleneiminoacetic acid, methyleneiminodiacetic acid, ethylenethioethyleneiminoacetic acid, ethylenethioethyleneiminodiacetic acid, TMT, a terpyridinyl group, a chelating agent comprising a terpyridyl group and a carboxymethylamino group, or a salt of any of the foregoing acids. Especially preferred chelating groups are DTPA, DTPA-BMA, DPDP, TMT, DOTA and HPDO3A.

Representative chelating groups are also described in U.S. Pat. No. 5,559,214 A, WO 9526754, WO 9408624, WO 9409056, WO 9429333, WO 9408624, WO 9408629 A1, WO 9413327 A1 and WO 9412216 A1.

Methods for metallating any chelating agents present are within the level of skill in the art. Metals can be incorporated into a chelant moiety by any one of three general methods: direct incorporation, template synthesis and/or transmetallation. Direct incorporation is preferred.

Thus it is desirable that the metal ion be easily complexed to the chelating agent, for example, by merely exposing or mixing an aqueous solution of the chelating agent-containing moiety with a metal salt in an aqueous solution preferably having a pH in the range of about 4 to about 11. The salt can be any salt, but preferably the salt is a water soluble salt of the metal such as a halogen salt, and more preferably such salts are selected so that the counterion does not interfere with the binding of the metal ion with the chelating agent. The chelating agent-containing moiety is preferrably in aqueous solution at a pH of between about 5 and about 9, more preferably between pH about 6 to about 8. The chelating agent-containing moiety can be mixed with buffer salts such as citrate, acetate, phosphate and borate to produce the optimum pH. The preferred buffer salt is acetate. Preferably, the buffer salts are selected so as not to interfere with the subsequent binding of the metal ion to the chelating agent.

In diagnostic imaging employing a radionuclide, the contrast agent preferably contains a ratio of metal radionuclide ion to chelating agent that is effective in such diagnostic imaging applications. In preferred embodiments, the mole ratio of metal ion per chelating agent is from about 1:1,000 to about 1:1.

In radiotherapeutic applications, the contrast agent preferably contains a ratio of metal radionuclide ion to chelating agent that is effective in such therapeutic applications. In preferred embodiments, the mole ratio of metal ion per chelating agent is from about 1:100 to about 1:1. The radionuclide can be selected, for example, from radioisotopes of Sc, Fe, Pb, Ga, Y, Bi, Mn, Cu, Cr, Zn, Ge, Mo, Ru, Sn, Sr, Sm, Lu, Sb, W, Re, Po, Ta and Tl. Preferred radionuclides include $^{44}Sc$, $^{64}Cu$, $^{67}Cu$, $^{212}Pb$, $68Ga$, $^{90}Y$, $^{153}Sm$, $^{212}Bi$, $^{186}Re$ and $^{188}Re$. Of these, especially preferred is $^{90}Y$. These radioisotopes can be atomic or preferably ionic.

The following isotopes or isotope pairs can be used for both imaging and therapy without having to change the radiolabeling methodology or chelator: $^{47}Sc_{21}$; $^{141}Ce_{58}$; $^{188}Re_{75}$; $^{177}Lu_{71}$; $^{199}Au_{79}$; $^{47}SC_{21}$; $^{131}I_{53}$; $^{67}Cu_{29}$; $^{131}I_{53}$; and $^{123}I_{53}$; $^{188}Re_{75}$ and $^{99m}Tc_{43}$; $^{90}Y_{39}$ and $^{87}Y_{39}$; $^{47}Sc_{21}$ and $^{44}Sc_{21}$; $^{90}Y_{39}$ and $^{123}I_{53}$; $^{146}Sm_{62}$ and $^{153}Sm_{62}$; and $^{90}Y_{39}$ and $^{111}In_{49}$.

A linker group is a chemical moiety that connects together at least two molecules, at least the residue of one molecule with another molecule, or at least the residue of one molecule with the residue of another molecule.

Where a linker moiety contains a single chelant, that chelant may be attached directly to a vector moiety, e.g. via one of the metal coordinating groups of the chelant which may form an ester, amide, thioester or thioamide bond with an amine, thiol or hydroxyl group on the vector. Alternatively the vector and chelant may be directly linked via a functionality attached to the chelant backbone, e.g. a $CH_2$-phenyl-NCS group attached to a ring carbon of DOTA as proposed by Meares et al. in JACS 110:6266–6267(1988), or indirectly via a homo or hetero-bifunctional linker, e.g. a bis amine, bis epoxide, diol, diacid, difunctionalised PEG, etc. In that event, the bifunctional linker will conveniently provide a chain of 1 to 200, preferably 3 to 30 atoms between vector and chelant residue.

Where a linker moiety contains a plurality of chelant groups, the linker preferably is or contains portions of formula

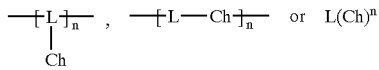

where Ch is a chelant moiety and L is a linker backbone component, i.e. the linker preferably has pendant chelants, in-backbone chelants or terminal chelants or a combination thereof. The pendant and in-backbone polymeric structures may be branched or linear and the repeat units (LCh) or other repeat units in the polymer may have in-backbone or pendant biodistribution modifying groups, e.g. polyalkylene groups as in WO94/08629, WO94/09056, and WO96/20754. The terminal chelant structures $L(Ch)_n$, which may be dendritic polymers as in WO93/06868, may have biodistribution modifying groups attached to termini not occupied by chelants and may have biodegradation enhancing sites within the linker structure as in WO95/28966.

The chelant moieties within the polychelant linker may be attached via backbone functionalization of the chelant or by utilization of one or more of the metal coordinating groups of the chelant or by amide or ether bond formation between acid chelant and an amine or hydroxyl carrying linker backbone, e.g. as in polylysine-polyDTPA, polylysine-polyDOTA and in the so-called magnifier polychelants, of PCT/EP96/00565. Such polychelant linkers may be conjugated to one or more vector groups either directly (e.g. utilizing amine, acid or hydroxyl groups in the polychelant linker) or via a bifunctional linker compound as discussed above for monochelant linkers.

Where the chelated species is carried by a particulate (or molecular aggregate, e.g. vesicular) linker, the chelate may for example be an unattached mono or polychelate (such as Gd DTPA-BMA or Gd HP-DO3A) enclosed within the particle or it may be a mono or polychelate conjugated to the particle either by covalent bonding or by interaction of an anchor group (e.g. a lipophilic group) on the mono/polychelate with the membrane of a vesicle (see for example PCT/GB95/02378).

Preferred non-metal atomic reporters include radioisotopes such as $^{123}I$ and $^{131}I$ as well as non zero nuclear spin atoms such as $^{18}F$, and heavy atoms such as I.

Such reporters, preferably a plurality thereof, e.g. 2 to 200, may be covalently bonded to a linker backbone, either directly using conventional chemical synthesis techniques or via a supporting group, e.g. a triiodophenyl group.

In an embodiment of this invention, the use of radioisotopes of iodine is specifically contemplated. For example, if the rest of the contrast agent or sensitizer contains substituents that can be chemically substituted by iodine in a covalent bond forming reaction, such as, for example, substituents containing hydroxyphenyl functionality, such substituents can be labeled by methods well known in the art with a radioisotope of iodine. The iodine species can be used in therapeutic and diagnostic imaging applications while, at the same time, a metal in a chelating agent on the same vector-linker can also be used in either therapeutic or diagnostic imaging applications.

As with the metal chelants discussed above, such metal atomic reporters may be linked to the linker or carried in or on a particulate linker, e.g. in a vesicle (see WO95/26205 and GB9624918.0).

Linkers of the type described above in connection with the metal reporters may be used for non-metal atomic reporters with the non-metal atomic reporter or groups carrying such reporters taking the place of some or all of the chelant groups.

For the sake of clarity, the word "particle" is used to refer to any physiologically acceptable particulate materials. Such particles may be solid (e.g. coated or uncoated crystalline materials) or fluid (e.g. liquid particles in an emulsion) or may be aggregates (e.g. fluid containing liposomes). Particulate materials with a particle size smaller than or similar to the incident light wavelength are preferred.

The particulate reporters and linker-reporters generally fall into two categories—those where the particle comprises a matrix or shell which carries or contains the reporter and those where the particle matrix is itself the reporter. Examples of the first category are: vesicles (e.g. micelles, liposomes, microballoons and microbubbles) containing a liquid, gas or solid phase which contains the contrast effective reporter, e.g. an echogenic gas or a precursor therefor (see for example GB 9700699.3), a chelated paramagnetic metal or radionuclide, or a water-soluble iodinated X-ray contrast agent; porous particles loaded with the reporter, e.g. paramagnetic metal loaded molecular sieve particles; and solid particles, e.g. of an inert biotolerable polymer, onto which the reporter is bound or coated, e.g. dye-loaded polymer particles.

Examples of the second category are: light scattering organic or inorganic particles; magnetic particles (i.e. superparamagnetic, ferromagnetic or ferrimagnetic particles); and dye particles.

Particulate reporters moreover may be loaded with cytopathogenic agents which can be released at the therapy site by the effect on the particulate (e.g. particle disruption or membrane disruption) of the ultrasound irradiation. Thus for example a liposome with a "stealth" coating of PEG may contain a fluorescent dye (such as 6-carboxyfluorescein) and a cytotoxin (such as actinomycin D, cyclophosphamide, mitomycin, bleomycin or paclitaxel) and may be used in SDT for both therapy and imaging.

Preferred particulate reporters or reporter-linkers include superparamagnetic particles (see U.S. Pat. No. 4,770,183, PCT/GB97/00067, WO96/09840, etc.), echogenic vesicles (see WO92/17212, PCT/GB97/00459, etc.), iodine-containing vesicles (see WO95/26205 and GB9624918.0), and dye-loaded polymer particles (see WO96/23524).

The particulate reporters may have one or more vectors attached directly or indirectly to their surfaces. Generally it will be preferred to attach a plurality (e.g. 2 to 50) of vector moieties per particle. Particularly conveniently, besides the desired targeting vector, one will also attach flow decelerating vectors to the particles, i.e. vectors which have an affinity for the capillary lumen or other organ surfaces which is sufficient to slow the passage of the contrast agent through the capillaries or the target organ but not sufficient on its own to immobilise the contrast agent. Such flow decelerating vectors (described for example in GB9700699.3) may moreover serve to anchor the contrast agent once it has bound to its target site.

The means by which vector to particle attachment is achieved will depend on the nature of the particle surface. For inorganic particles, the linkage to the particle may be for example by way of interaction between a metal binding group (e.g. a phosphate, phosphonate or oligo- or polyphosphate group) on the vector or on a linker attached to the vector. For organic (e.g. polymeric) particles, vector attachment may be by way of direct covalent bonding between groups on the particle surface and reactive groups in the vector, e.g. amide or ester bonding, or by covalent attachment of vector and particle to a linker. Linkers of the type discussed above in connection with chelated metal reporters may be used although in general the linkers will not be used to couple particles together.

For non-solid particles, e.g. droplets (for example of water insoluble iodinated liquids as described in U.S. Pat. Nos. 5,318,767, 5,451,393, 5,352,459 and 5,569,448) and vesicles, the linker may conveniently contain hydrophobic "anchor" groups, for example saturated or unsaturated $C_{12-30}$ chains, which will penetrate the particle surface and bind vector to particle. Thus for phospholipid vesicles, the linker may serve to bind the vector covalently to a phospholipid compatible with the vesicle membrane. Examples of linker binding to vesicles and inorganic particles are described in GB9622368.0 and PCT/GB97/00067.

Besides the vectors, other groups may be bound to the particle surface, e.g. stabilisers (to prevent aggregation) and biodistribution modifiers such as PE.g. Such groups are discussed for example in PCT/GB97/00067, WO96/09840, EP-A-284549 and U.S. Pat. No. 4,904,479.

Preferably the sensitizers and contrast agents of the invention will have the non-peptidic endothelin receptor targetting vectors (such as bosentan or BMS 182874) coupled directly or indirectly to a reporter, e.g. with covalently bound iodine radioisotopes, with metal chelates attached directly or via an organic linker group or coupled to a particulate reporter or linker-reporter, e.g. superparamagnetic crystals (optionally coated, e.g. as in PCT/GB97/00067), or a vesicle, e.g. a gas containing or iodinated contrast agent containing micelle, liposome or microballoon.

Chromophores

By chromophore is meant a group in a composition of matter, e.g. an organic or inorganic group which absorbs and/or emits light. The term thus includes fluorophores, groups which are fluorescent, as well as phosphorescent groups. In general chromophores will contain a complexed metal ion or an extensive delocalized electron system. One aspect of the present invention is particularly concerned with the latter type. A compound containing a chromophore is sometimes herein referred to as a chromophore.

By light is meant electromagnetic radiation having wavelengths from 300–1300 nm. Chromophores having absorption and/or emission maxima in the visible to far infra-red range are particularly relevant to the invention.

As mentioned above, the sensitizers and contrast agents used according to the invention preferably contain at least one chromophore. Preferably also they will contain a plurality of sulphonic acid groups (or derivatives thereof, e.g. salts). Such groups may promote retention at tumor sites. Where the sensitizers contain more than one chromophore, these may be the same or different. Generally however it will be preferred that the chromophores are the same. When used as reporter groups, the chromophores will preferably be fluorophores, i.e. the sensitizers are preferably fluorescent. In this way they are easier to detect by eye or with suitable imaging equipment. Particularly preferably, the chromophores will have absorption maxima in the 300–1300 nm wavelength range, most preferably 600–1300 nm. Appropriate chromophores are well known and can readily be modified to carry sulphonic acid groups if required, these groups preferably being disposed about the chromophore rather than all being attached in the same general area of the molecule. Preferably, the sulphonic acid groups will be attached to aryl groups in the chromophores either directly or via $C_{1-10}$ linkers such as alkylene chains.

Preferred chromophores include compounds having an extensive delocalized electron system, e.g. cyanines, merocyanines, phthalocyanines, naphthalocyanines, triphenylmethines, porphyrins, pyrilium dyes, thiapyrilium dyes, squarylium dyes, croconium dyes, azulenium dyes, indoanilines, benzophenoxazinium dyes, benzothiaphenothiazinium dyes, anthraquinones, naphthoquinones, indathrenes, phthaloylacridones, trisphenoquinones, azo dyes, intramolecular and intermolecular charge-transfer dyes and dye complexes, tropones, tetrazines, bis (dithiolene) complexes, bis(benzene-dithiolate) complexes, iodoaniline dyes, bis(S,O-dithiolene) complexes, etc. Examples of suitable organic or metallated organic chromophores may be found in "Topics in Applied Chemistry: Infrared absorbing dyes" Ed. M. Matsuoka, Plenum, N.Y. 1990, "Topics in Applied Chemistry: The Chemistry and Application of Dyes", Waring et al., Plenum, N.Y., 1990, "Handbook of Fluorescent Probes and Research Chemicals" Haugland, Molecular Probes Inc, 1996, DE-A-4445065, DE-A-4326466, JP-A-3/228046, Narayanan et al. J. Org. Chem. 60: 2391–2395 (1995), Lipowska et al. Heterocyclic Comm. 1: 427–430 (1995), Fabian et al. Chem. Rev. 92: 1197 (1992), WO96/23525, Strekowska et al. J. Org. Chem. 57: 4578–4580 (1992), and WO96/17628. Particular examples of chromophores which may be used include xylene cyanole, fluorescein, dansyl, NBD, Pc, indocyanine green, DODCI, DTDCI, DOTCI and DDTCI.

Particularly preferred are compounds which have absorption maxima between 600 and 1000 nm to avoid interference with haemoglobin absorption (e.g. xylene cyanole).

Further such examples include:

cyanine dyes: such as heptamethinecyanine dyes, e.g. compounds 4a to 4 g Table II on page 26 of Matsuoka (supra)

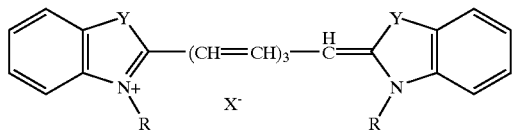

4a: where Y=S, X=I, R=Et
4b: where Y=S, X=ClO$_4$, R=Et
4c: where Y=CMe$_2$, X=I, R=Me
4d: where Y=CMe$_2$, X=ClO$_4$, R=Me
4e: where Y=CH=CH, X=I, R=Et
4f: where Y=CH=CH, X=Br, R=Et
4g: where Y=CH=CH, X=ClO$_4$, R=Et and in Table III on page 28 of Matsuoka (supra), i.e.

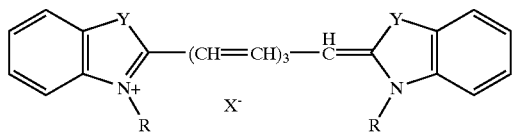

where Y=O, X=I, R=Me
where Y=CMe$_2$, X=I, R=Me
where Y=S, X=Br R=Et;

chalcogenopyrylomethine dyes, e.g., compounds 12 on page 31 of Matsuoka (supra), i.e.

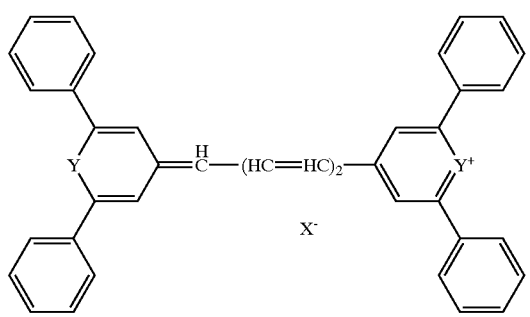

where Y=Te, Se, O or NR;

monochalcogenopyrylomethine dyes, e.g. compounds 13 on page 31, of Matsuoka (supra) i.e.

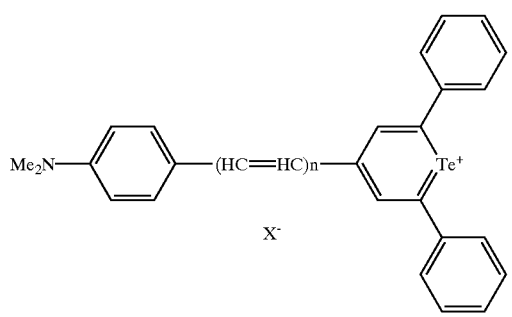

where n=1 or 2;

pyrilium dyes, e.g., compounds 14 (X=O) on page 32 of Matsuoka (supra), i.e.

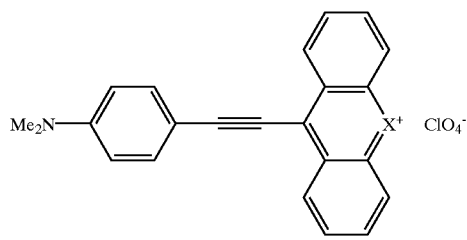

where X=O, S, or Se;

thiapyrilium dyes, e.g. compounds 15 on page 32, and compound I on page 167 of Matsuoka (supra), i.e.

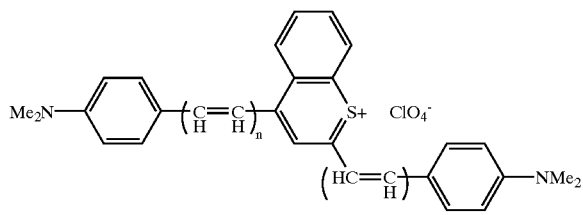

where n=1 or 2;

squarylium dyes, e.g. compound 10 and Table IV on page 30 of Matsuoka (supra), i.e.

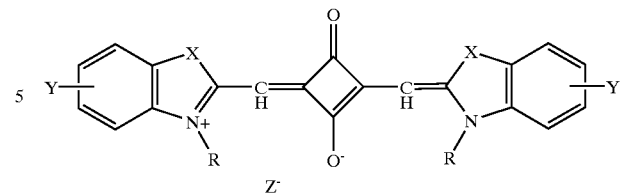

where
X=CH=CH, Y=H, and R=Et,
X=S, Y=H, and R=Et, and
X=CMe$_2$, Y=H, and R=Me, and compound 6, page 26, of Matsuoka (supra), i.e.

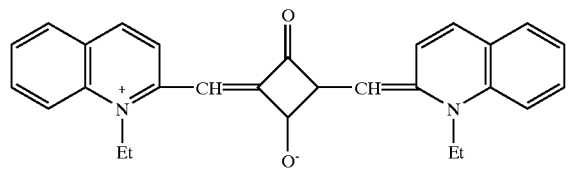

croconium dyes, e.g. compound 9 and Table IV on page 30 of Matusoka (supra), i.e.

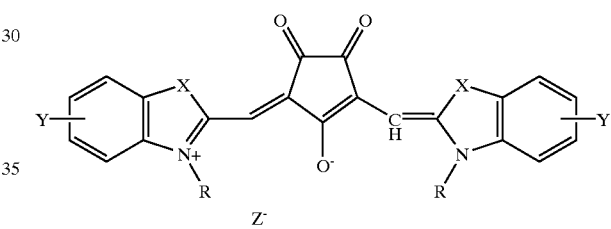

where
X=CH=CH, Y=H, and R=Et,
X=S, Y=H, and R=Et,
X=CMe$_2$, Y=H, and R=Me, and compound 7, page 26, of Matsuoka (supra), i.e.

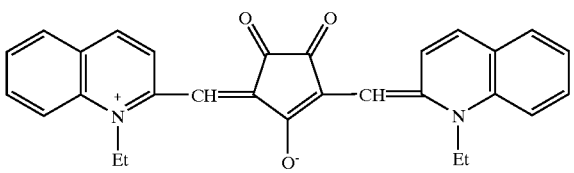

azulenium dyes, e.g. compound 8 on page 27 of Matsuoka (supra), i.e.

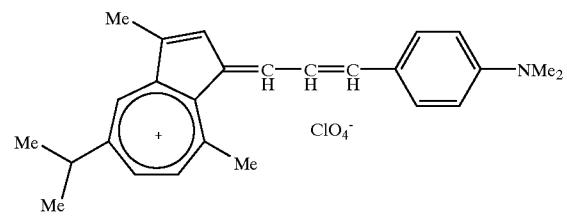

merocyanine dyes, e.g. compound 16, R=Me, on page 32 of Matsuoka (supra), i.e.

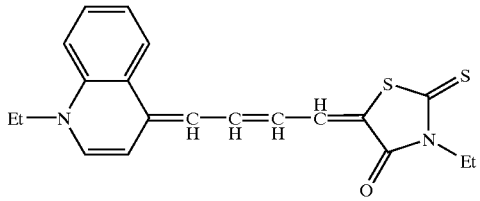

indoaniline dyes such as copper and nickel complexes of indoaniline dyes, e.g. compound 6 on page 63 of Matsuoka (supra), i.e.

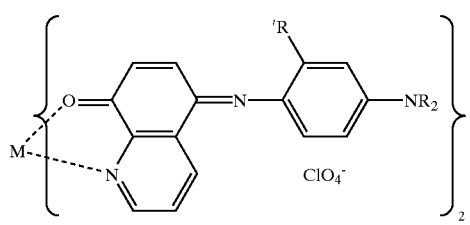

where
R=Et, R'=Me, M=Cu,
R=Et, R'=Me, M=Ni,
R=Me, R'=H, M=Cu, or
R=Me, R'=H, M=Ni, benzo [a] phenoxazinium dyes and benzo [a] phenothiazinium dyes, e.g. as shown on page 201 of Matusoka (supra), i.e.

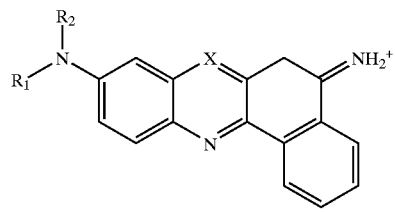

where X=O or S;
1,4-diaminoanthraquinone(N-alkyl)-3'-thioxo-2,3-dicarboximides, e.g. compound 20, on page 41 of Matusoka (supra)

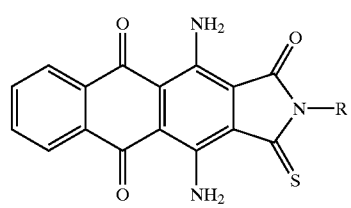

indanthrene pigments, e.g.

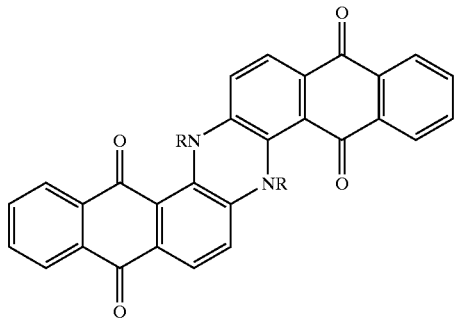

see compound 21 on page 41 of Matsuoka (supra); 2-arylamino-3,4-phthaloylacridone dyes, e.g. compound 22 on page 41 of Matsuoka (supra)

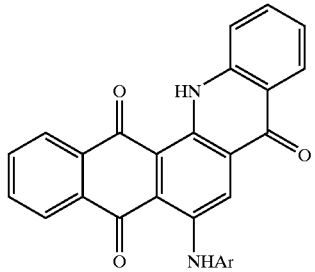

trisphenoquinone dyes, e.g. compound 23 on page 41 of Matsuoka (supra)

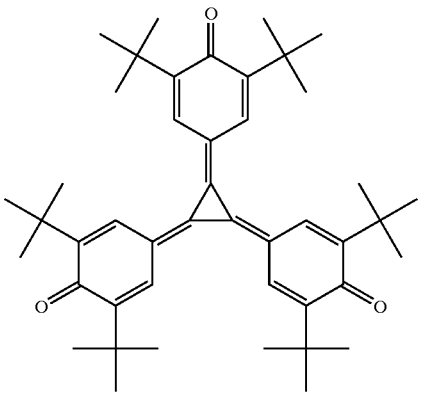

azo dyes, e.g. the monoazo dye, compound 2 on page 90 of Matsuoka (supra), i.e.

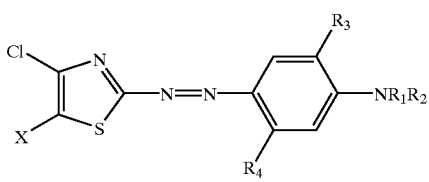

where X=CH=C(CN)$_2$, R$_1$=R$_2$=Et, R$_3$=R$_4$=H,
X=C(CN)=C(CN)$_2$, R$_1$=R$_2$=Et, R$_3$=R$_4$=H, or
X=

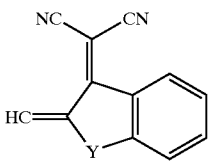

and Y=C=O, R$_1$=R$_2$=Et, R$_3$=R$_4$=H, or
Y=SO$_2$, R$_1$=H, R$_2$=CH(Me)nBu, R$_3$=OMe, and R$_4$=NHAC;

azo dyes, e.g. the polyazo dye, compound 5 on page 91 of Matsuoka (supra), i.e.

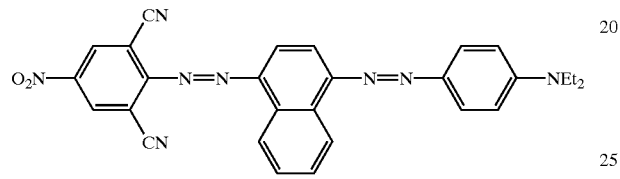

intramolecular charge transfer donor-acceptor infrared dyes, e.g. compounds 6 and 7 on page 91 of Matsuoka (supra), i.e.

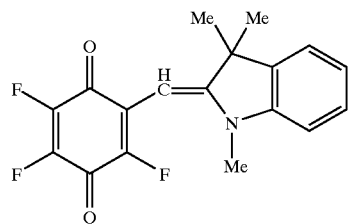

and

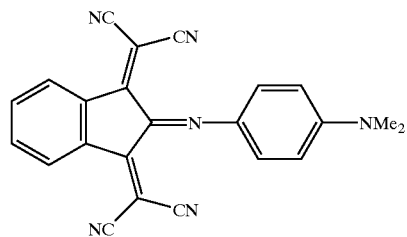

nonbenzenoid aromatic dyes, e.g. compound 8, a tropone, on page 92, of Matsuoka (supra), i.e.

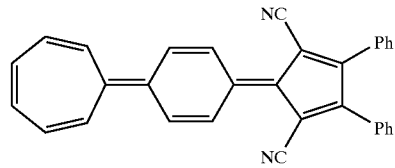

tetrazine radical dyes, e.g. compound 9 on page 92 of Matsuoka (supra), i.e.

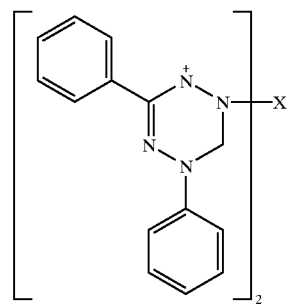

in which,
X=p-phenylene or
X=p-terphenylene as well as compound 10 on page 92 of Matsuoka (supra), i.e.

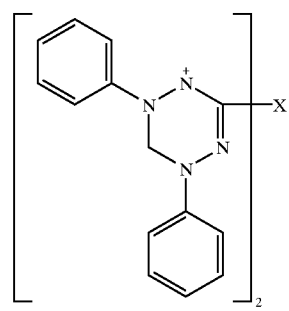

in which X=p-biphenyl;

cationic salts of tetrazine radical dyes, e.g. compound 11 on page 92 of Matsuoka (supra)

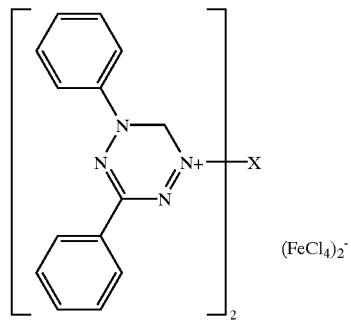

(FeCl$_4$)$_2^-$ in which X=p-phenylene;

donor-acceptor intermolecular charge transfer dyes, e.g. charge transfer (CT) complexes of compounds 13b and 14a to 14c on page 93 of Matsuoka (supra), i.e.

donor

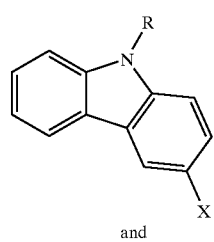

and

-continued

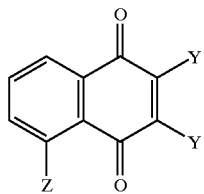

where X=CH=N—N(Ph)$_2$ in the donor and
a) Y=CN, Z=NO$_2$
b) Y=CN, Z=H or
a) Y=Cl, Z=NO$_2$ in the acceptor;
anthraquinone dyes, e.g. compounds 12 (X=S or Se) on page 38 of Matsuoka (supra), i.e.

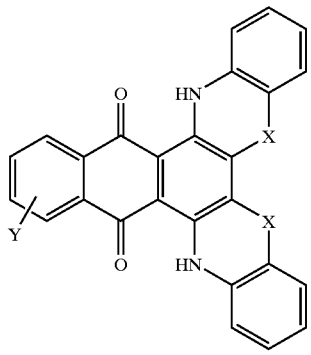

wherein X=S or Se and Y=tetrachloro, tetrabromo, 2,3-dicarboxylic acid, 2,3-dicarboxylic anhydride, or 2,3-dicarboxylic acid N-phenyl imide;
naphthoquinone dyes, e.g. compounds 2, 3, and 4 on page 37, of Matsuoka (supra), i.e.

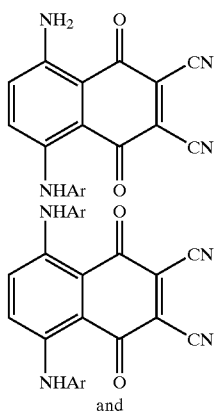

and

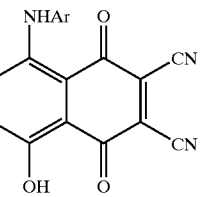

metallated azo dyes such as azo dyes containing nickel, cobalt, copper, iron, and manganese;
phthalocyanine dyes, e.g. compound 1 in Table II on page 51 of Matsuoka (supra), e.g.

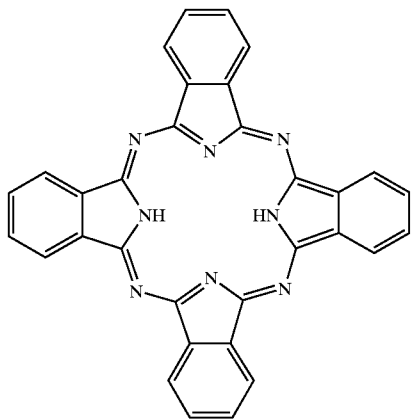

naphthalocyanine dyes, e.g. compound 3 in Table II on page 51 of Matsuoka (supra), e.g.

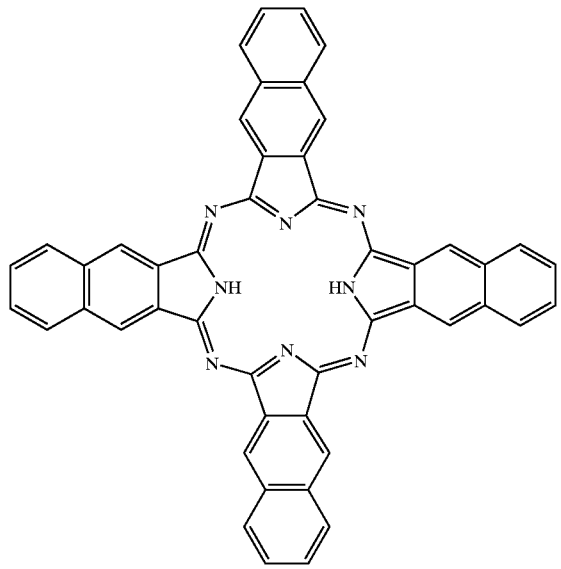

metal phthalocyanines such as phthalocyanines containing aluminum, silicon, nickel, zinc, lead, cadmium, magnesium, vanadium, cobalt, copper, and iron, (especially those containing Al, Si and Zn which are fluorophores) e.g. compound 1 in Table III on page 52 of Matsuoka (supra), e.g.

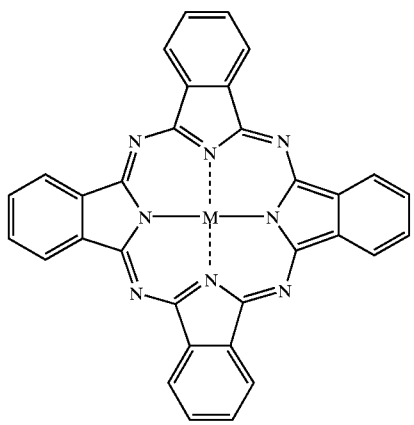

in which, for example, M=Mg;

metal naphthalocyanines such as naphthalocyanines containing aluminum, zinc, cobalt, magnesium, cadmium, silicon, nickel, vanadium, lead, copper, and iron (especially those containing Al, Si or Zn which are fluorophores), see compound 3 in Table III on page 52 of Matsuoka (supra), e.g.

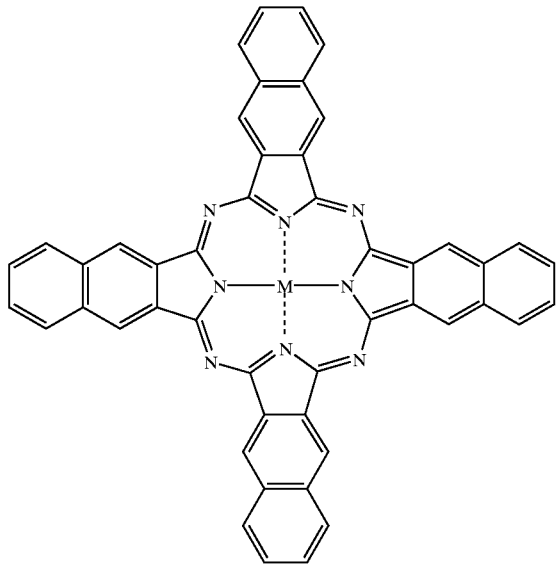

in which, for example, M=Mg;

bis(dithiolene) metal complexes comprising a metal ion such as nickel, cobalt, copper, and iron coordinated to four sulfur atoms in a bis(S,S'-bidentate) ligand complex, e.g. see Table I on page 59 of Matsuoka (supra)

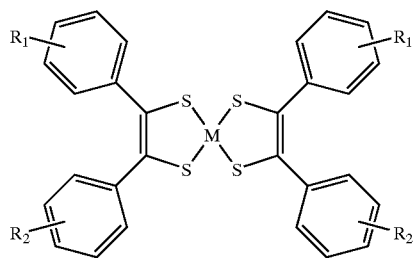

where
$R_1=R_2=CF_3$, M=Ni,
$R_1=R_2$=phenyl, M=Pd,
$R_1=R_2$=phenyl, M=Pt,
$R_1$=C4 to C10 alkyl, $R_2$=H, M=Ni,
$R_1$=C4 to C10 alkyl, $R_2$=H, M=Pd,
$R_1$=C4 to C10 alkyl, $R_2$=H, M=Pt,
$R_1=R_2$=phenyl, M=Ni,
$R_1=R_2$=p-$CH_3$-phenyl, M=Ni,
$R_1=R_2$=p-$CH_3O$-phenyl, M=Ni,
$R_1=R_2$=p-Cl-phenyl, M=Ni,
$R_1=R_2$=p-$CF_3$-phenyl, M=Ni,
$R_1=R_2$=3,4,-diCl-phenyl, M=Ni,
$R_1=R_2$=o-Cl-phenyl, M=Ni,
$R_1=R_2$=o-Br-phenyl, M=Ni,
$R_1=R_2$=3,4,-diCl-phenyl, M=Ni,
$R_1=R_2$=p-$CH_3$, M=Ni,
$R_1=R_2$=2-thienyl, M=Ni,
$R_1$=p-$(CH_3)_2$ N-phenyl, $R_2$=phenyl, M=Ni, and
$R_1$=p-$(CH_3)_2$ N-phenyl, $R_2$=p-$H_2N$-phenyl, M=Ni;

bis(benzenedithiolate) metal complexes comprising a metal ion such as nickel, cobalt, copper, and iron coordinated to four sulfur atoms in a ligand complex, e.g. see Table III on page 62 of Matsuoka (supra), i.e.

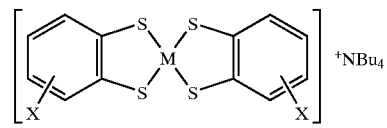

where
X=tetramethyl, M=Ni,
X=4,5-dimethyl, M=Ni,
X=4-methyl, M=Ni,
X=tetrachloro, M=Ni,
X=H, M=Ni,
X=4-methyl, M=Co,
X=4-methyl, M=Cu, and
X=4-methyl, M=Fe;

N,O-bidentate indoaniline dyes comprising a metal ion such as nickel, cobalt, copper, and iron coordinated to two nitrogen and two oxygen atoms of two N,O-bidentate indoaniline ligands, e.g. compound 6 in Table IV on page 63 of Matsuoka (supra), e.g.

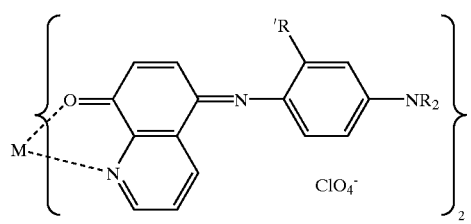

where
R=Et, R'=Me, M=Cu,
R=Et, R'=Me, M=Ni,
R=Me, R'=H, M=Cu, and
R=Me, R'=H, M=Ni, bis(S,O-dithiolene) metal complexes comprising a metal ion such as nickel, cobalt, copper, and iron coordinated to two sulfur atoms and two oxygen atoms in a bis(S, O-bidentate) ligand complex, e.g. see U.S. Pat. No. 3,806,462, e.g.

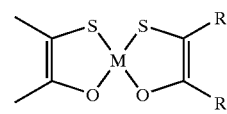

α-diimine-dithiolene complexes comprising a metal ion such as nickel, cobalt, copper, and iron coordinated to two sulfur atoms and two imino-nitrogen atoms in a mixed S,S- and N,N-bidentate diligand complex, e.g. see Table II on page 180, second from bottom, of Matsuoka (supra) (also see Japanese patents: 62/39, 682, 63/126,889 and 63/ 139,303), e.g.

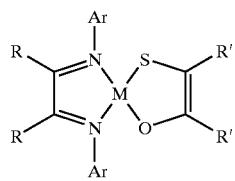

and tris(α-diimine) complexes comprising a metal ion coordinated to six nitrogen atoms in a triligand complex, e.g. see Table II on page 180 of Matsuoka (supra), last compound, (also see Japanese Patents 61/20,002 and 61/73,902), e.g.

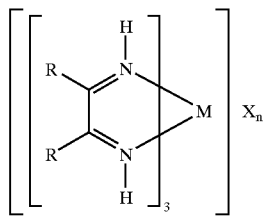

Representative examples of visible dyes include fluorescein derivatives, rhodamine derivatives, coumarins, azo dyes, metalizable dyes, anthraquinone dyes, benzodifuranone dyes, polycyclic aromatic carbonyl dyes, indigoid dyes, polymethine dyes, azacarbocyanine dyes, hemicyanine dyes, barbituates, diazahemicyanine dyes, stryrl dyes, diaryl carbonium dyes, triaryl carbonium dyes, phthalocyanine dyes, quinophthalone dyes, triphenodioxazine dyes, formazan dyes, phenothiazine dyes such as methylene blue, azure A, azure B, and azure C, oxazine dyes, thiazine dyes, naphtholactam dyes, diazahemicyanine dyes, azopyridone dyes, azobenzene dyes, mordant dyes, acid dyes, basic dyes, metallized and premetallized dyes, xanthene dyes, direct dyes, leuco dyes which can be oxidized to produce dyes with hues bathochromically shifted from those of the precursor leuco dyes, and other dyes such as those listed by Waring, D. R. and Hallas, G., in "The Chemistry and Application of Dyes", Topics in Applied Chemistry, Plenum Press, New York, N.Y., 1990. Additonal dyes can be found listed in Haugland, R. P., "Handbook of Fluorescent Probes and Research Chemicals", Sixth Edition, Molecular Probes, Inc., Eugene, Oreg., 1996.

Other dye types that can be used in this invention include: Diarylmethane dyes, including but not limited to Acridine dyes, including Acridine Orange, Yellow, Red, Nile Blue, Lucifer Yellow CH, Methylene Blue, Michler's Hydrol Blue, Bindschedler's green, Toluidine Blue, and their derivatives. Triarylmethane dyes, including but not limited to Malachite Green, Crystal Violet, Victoria Blue, Fluorescein, Rose Bengal, Rhodamine, Isosulfan Blue, and their derivatives. Merocyanine dyes, including Merocyanine 540, and their derivatives, Porphyrins.

Most preferably, the chromophores are triphenylmethanes, cyanines, merocyanines, phthalocyanines, naphthalocyanines or porphyrins.

As mentioned above, the sensitizers or contrast agents of the invention may contain a single chromophore ("monomeric" dyes) or they may contain more than one, e.g. 2 to 100, especially 2 to 10, chromophores ("polymeric" dyes). Where the dye compound is polymeric, the structure can be any of the well known polymer structures, e.g. with the chromophores pendant from a molecular (preferably polymeric) backbone, with the chromophores forming part of a polymer backbone, with the chromophores attached to the termini or interior of a branched molecular structure or a combination of such structures. The chromophores may also be attached to the termini of the arms of a dendritic polymer. In these cases, the organic skeletons of the chromophores will be coupled together, e.g. with pairs of chromophore skeletons being coupled via bonds of linking groups, or several will be coupled to a common backbone structure, which linking groups or backbone structures may be vectors as discussed below. Such structures have been widely described in relation to polychelant compounds useful as MRI contrast agents. However with metal or pseudometal containing chromophores, such as the porphyrins, phthalocyanines, and naphthalocyanines and others mentioned above, a further polymeric structure is possible where linkage of the chromophores is via the metal rather than the organic skeleton. Such polymers are termed cofacial polymers and represent a particular novel aspect of the invention. For the purposes of this text, polychromophores are compounds containing two or more chromophoric groups.

Thus such polymeric dye compounds may conveniently have the formulae

where n is an integer with the value 2 or greater (e.g. 2 to 100), Chr is a chromophore and L is a bond, linker group (e.g. a divalent or trivalent organic linker), branched multivalent linker structure (e.g. a dendrimer or starburst polymer), or a vector group (or vector-linker combination) as discussed below.

The linker and vector-linker groups used may be of the types used in the polychelants known from the MRI contrast agent field. Preferably however the linker groups comprise a hydrophilic polymer moiety, e.g. a polyalkyleneoxy component, in their linking skeleton, e.g., a component $[(CR_aR_b)_x-(CH_2)_y-O-]_s, [-O-(CR_aR_b)_x-(CH_2)_y-]_s$ where x=1, y=1–3, where x=0, y=2–4 and $R_a$, $R_b$=H, $CH_3$, $CH_2CH_3$ and s is preferably such that the $[(CR_aR_b)_x-(CH_2)_y-O-]_s, [-O-(CR_aR_b)_x-(CH_2)_y-]_s$ unit has a molecular weight of 100 to 10,000, especially 1000 to 5000. Such units may comprise alkylene units, $(CH_2)_q$, of different lengths, e.g. in blocks such as $((CH_2)_2O)_t((CH_2)_3O)_v$, where t and v are integers having values above 2. Thus for example the polychromophores may be of formula Chr-$L_1$-(PAO-$L_2$-Chr)$_u$, where Chr is a chromophore, optionally and preferably containing a sulphonic acid group, $L_1$ and $L_2$ are bonds or linking functions, PAO is a polyalkyleneoxy group and u is an integer having a value of at least 1, e.g. 1 to 100. In SDT, useful compounds include chromophores to which are attached one or more polyoxyalkylene oxide groups.

In the polychromophore compounds, in one aspect it is preferred that each chromophore should carry at least one sulphonic acid (or derivative) group, preferably at least two and more preferably at least three such groups. It is especially preferred that chromophore compounds used according to the invention contain at least 6, preferably at least 8 sulphonic acid (or derivative groups). For the monomeric dyes, the total number of such groups may for example be as high as 12. For the polymeric dye compounds, the total number will depend upon the degree of polymerization but the total number may for example be as high as ten times the total number of chromophores.

The sulphonic acid groups may be present as the free acid ($SO_3H$) or as salts thereof with physiologically acceptable anions, e.g. alkali metal, alkaline earth metal, ammonium and organic amine ions (e.g. sodium, potassium, ammonium, ethanolamine, diethanolamine, meglumine, etc).

The presence of, and the nature and degree of derivatization of, the sulphonic acid groups affects the hydrophilicity, lipophilicity and ionic nature of the chromophore compounds used in the invention. This in turn affects their ability to penetrate tumor cells or simply to accumulate around tumor cells.

The molecular weight of a reporter (e.g. chromophore) can be manipulated for maximum localisation at a chosen site and the presence of many localising groups in a molecule increases the likelihood that a molecule will be localised. In addition, the localisation of a single molecule of a multi-reporter sensitizer or contrast agent (e.g. a polychromophore built up from many individual chromophore molecules) gives a much stronger signal than that resulting from the localisation of a single reporter. Aggregation is prevented, or substantially so, in a polymeric dye because the individual molecules in the polymer chain are constrained by the chain itself and cannot therefore align themselves to a significant extent.

The polysulphonic acid compounds used according to the invention are of particular interest in view of their ability to become immobilized in the vascular stroma of tumor tissue. This ability increases as the number of sulphonic acid groups increases. This may be due to binding to collagen, in particular uncrosslinked collagen in new tumors.

While it is possible to introduce sulphonic acid groups on preformed sensitizer or contrast agent compounds, it is especially preferred to introduce the sulpho groups during construction of the compound's skeleton as the number of sulpho groups can then be better controlled. For chromophores by way of example, this may generally be achieved by using chloro or polychloro substituted analogs of the aryl reagents conventionally used in chromophore construction. These can be reacted with NaSH and oxidized to the sulpho or polysulpho analogs of the conventional aryl reagents. Thus for phthalocyanines or naphthalocyanines (referred to herein by the abbreviation Pc, with PcS$_n$, meaning such a dye with n sulphonic acid groups), PcS$_8$ can readily be constructed using disulphophthalic acids (or phthalonitriles or phthalamides, etc). Where an appropriate core forming compound is present during the synthesis, a metal or pseudometal cored MPcS$_8$ compound (where M is an element such as Si, Al, Zn, etc) can be produced.

In the case of other chromophores, it is also possible to introduce a number of sulphonic acid groups during construction of the chromophore skeleton. Thus for example with cyanines having indoles or benzindoles (or oxygen or sulphur analogs) as the end groups, cyanines with 4 or 6 sulphonic acid groups may be produced by using indoles or benzindoles (or oxygen or sulphur analogs), etc. reagents carrying two sulphonic acid groups. Two further sulphonic acid groups can be introduced by quaternization with propane- or butane-sulfone. In cyanine dyes prepared according to the method of J. Org. Chem. 42(5), 885 (1997) additional sulphonic acid groups can be added by substitution of the central cycloalkene group, e.g. replacing a chloro substituent by a mono or polysulphonated phenoxyl. In this way, cyanine dyes with up to 10 sulphonic acid groups per molecule can readily be prepared.

Novel monomeric dyes which are phthalocyanines (or naphthalocyanines) with eight sulfo-groups may be prepared by the following scheme:

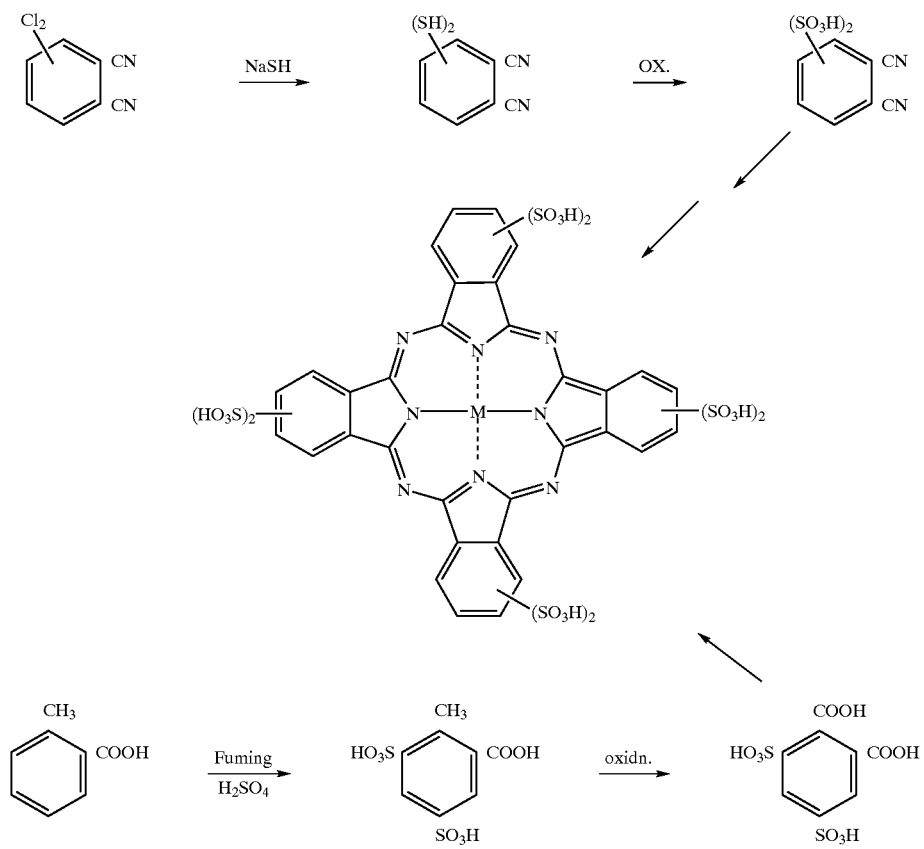

The two additional groups substituting each o-dicyanobenzene molecule may be orientated o-, m-, or p- to each other, and M represents an appropriately substituted element (e.g. Al(Cl), Si(OR)$_2$) which may optionally be present.

Compared to tetrasubstituted Pc's, some octasubstituted Pc's have the advantage that no position isomers can be formed from two of the three possible starting materials, i.e.

the 3,6 and 4,5 substituted o-dicyanobenzenes could produce only a single octasulfo-Pc derivative, increasing the yield and simplifying the purification of these products. The octasubstituted derivatives also tend to absorb at higher wavelengths, where skin penetration by light is greater. Before use these, and the other sulfonic acid derivatives discussed below, are converted to sodium or other physiologically acceptable sulfonate salts.

An example of a preferred new monomeric cyanine dye is:

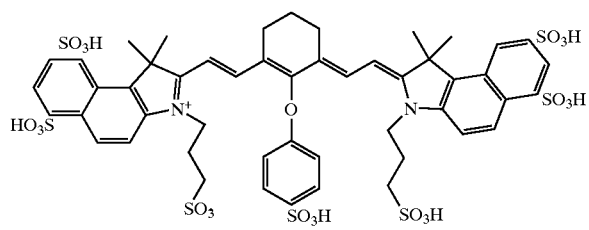

This new compound, containing seven sulfo-groups, can be made utilizing known literature methods. (Mujumdar, et al., *Cyanine-labeling reagents. Sulfobenzindocyanine succinimidyl esters*. Bioconj. Chem. 1996 7 356–62; Narayanan et al., *A new method for the synthesis of heptamethine cyanine dyes: synthesis of new near-infrared fluorescent labels*. J. Org. Chem. 1995 60 2391–5)

Comparable, but dye-enriched compounds can be made from di- or polyamines, e.g. from a PEG diamine:

$_3$(HO$_3$S) PCSO$_2$NHPEGNHSO$_2$Pc (SO$_3$H)$_3$ and from melamine, a triamine:

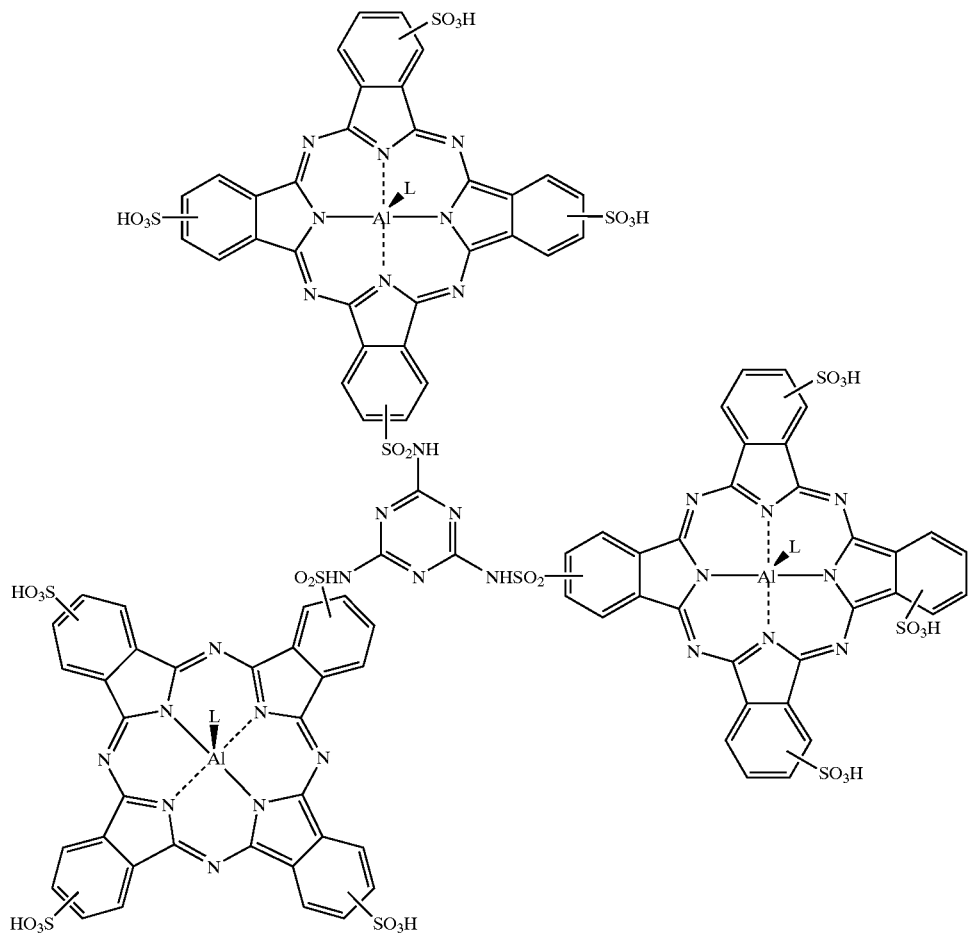

L=Cl, OH, hydrolytically stable PEG group, optionally used as linker for specific targeting vector, or other desired group.

Other polyamines that can be used include ethylenediamine, diethylenetriamine, triethylenetetramine, etc., neopentyltetramine, tris(2-aminoethyl)amine, di- and tri-aminocyclohexanes, piperazine, triazacyclononane, tetraazocyclododecane and tetradecane and pentadecane, di- and triaminobenzenes, polyaminobiphenyls, polyaminonaphthalenes, hydrazine, etc.

The polysulphonic acid materials discussed above are polyanionic. For some uses and for patient comfort after injection into the blood, it may be desirable to have products that are nonionic. Such compounds can readily be prepared from acid-derived acid chlorides by reaction with amines. Where water solubility is required, hydrophilic amines are preferred, such as PEG amines, ethanolamine, diethanolamine, dihydroxypropylamines, N-methylglucamine, etc. For example, a phthalocyanine sulfonate dye PEG-based composition could be:

Pc(SO$_2$NHPEG)$_4$ where PEG=a polyethyleneglycol group of an appropriate molecular weight.

Any of the acid chloride dye derivatives described in this document which have been reacted with an amine to produce a product still possessing some unreacted acid chloride groups can subsequently be further reacted with excess of a hydrophilic amine to yield an amidic product that can be nonionic.

Other compositions that could be prepared include zwitterionic compounds, which would be effectively nonionic by virtue of the fact that when they are dissolved only a single solute species is produced, whereas ionic compounds produce at least two, an anion and a cation. Compounds of this type can be prepared from the well known tetrapyridophthalocyanines by direct tetrasulfonation but this requires forcing conditions. They may more conveniently be prepared by treatment of pyrido-Pc's with propanesultone, e.g.

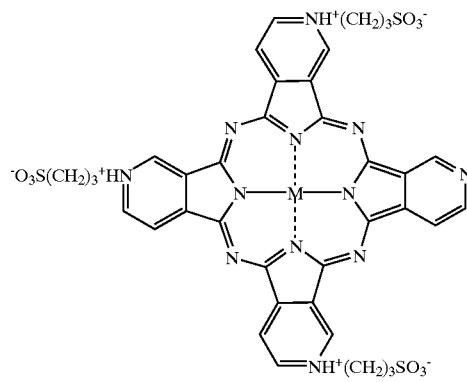

Where M=AlCl, $SiCl_2$, etc.

The positively charged nitrogen atoms can be at the 3, 4, or 5 positions in each of the isoindole groups.

This reaction with pyridine is well known (Andersen et al., Synthesis of pyridinium-1-propane-3'-sulfonate (PPS). A powerful electron scavenger and positronium inhibitor. Acta Chem. Scand. Ser. B. 1979 B33(9) 695–6) but has not previously been reported for pyridino-Pc's. The corresponding octasubstituted derivatives can be prepared from pyridazino-Pc (2 N atoms ortho), pyrimidino-Pc (2 N atoms meta), or pyrazino-Pc (2 N atoms para).

Either of these two concepts for nonionic compounds—zwitterionicity or hydrophilic amidation—could be applied to any of the sensitizers or contrast agents in this disclosure to prepare nonionic hydrophilic analogs.

In addition to anionic and nonionic compounds, cationic compounds are possible, and may be of particular interest from the point of view of the good tumor localization capability of such compounds. These are also readily derived from acid chlorides, for example using a Pc tetra-sulfonylchloride and cholamine one can obtain:

The water solubility of such compounds can be improved by increasing the hydrophilicity of the quaternizing group, e.g. $-N^+(CH_2CH_2OH)_3$, $-N^+Me(CH_2CH_2OH)_2$, etc.

The above outlined types of compound can also be prepared from cyanine dyes.

The oligomeric and polymeric dyes are useful compounds which can readily be synthesized, e.g. from $AlClPcS_4$, which is commercially available, and which for synthetic purposes are typically first converted to the tetrasulfonylchloride using thionyl chloride. Alternatively, the sulfonation of the Pc or other chromophore with chlorosulfonic acid and thionyl chloride gives the tetrasulfonylchloride directly as a water insoluble, readily isolable solid.

In one embodiment, products that can be oligomeric or polymeric can be made by the reaction of $Pc(SO_2Cl)_4$ derivatives with oligo- or polymeric polyamines, such as poly(ethyleneimine), etc., to form branched polymers:

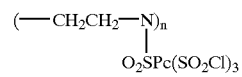

If desired, other reactions can be carried out at this stage or, if an anionic product is desired, a final hydrolysis step generates the required polysulfonamide.

It is recognized that the reaction product depicted is oversimplified and that pendant $-NH_2$ groups may be present in the starting polymer, and that branching and a certain amount of crosslinking may occur, but this does not affect the efficacy of the products as long as many unreacted sulfo-groups are present in the final product. This can be achieved by control of the relative proportions of the two reactants.

Dyes with sulfonamide Pc groups in the backbone can be made as oligomers or polymers by reacting $PcS_4$ sulfonyl chlorides with diamines in equimolar proportions (copolymerization):

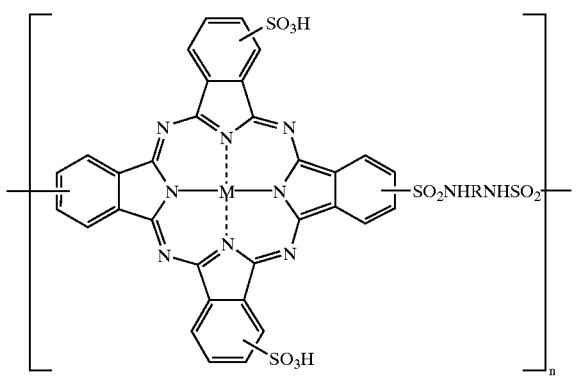

where R represents ethylene to poly(ethylene), di(ethyleneoxy) to poly(ethyleneoxy), phenylene to polyphenylene, etc.

Polymeric or oligomeric dyes with pendant sulfo-Pc groups can be prepared by vinyl polymerization of a Pc containing monomer, e.g. from compounds such as:

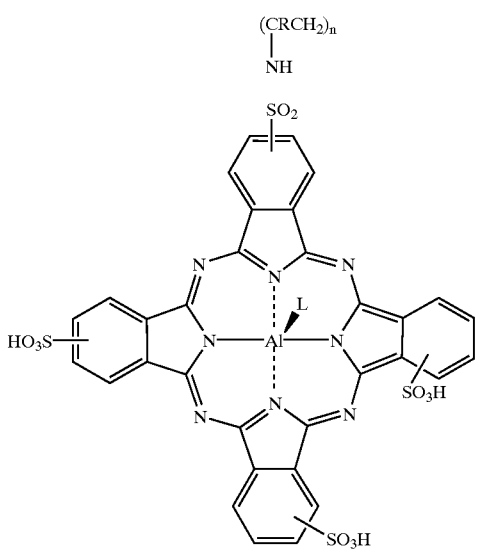

where R=H or lower alkyl

A similar product can be made by reacting the Pc tetrasulfonylchloride with poly(allylamine) or with poly(vinylamine).

In general, it should be noted that the polymers (e.g. polychromophores) used or produced according to the invention may contain a variety of different structures and degrees of polymerization.

The invention also covers the use of carboxamide derivatives analogous to those described above, which can be prepared for example from Pc tetracarboxylic acid chlorides. Related materials can also be prepared from tetrahydroxy-Pc's and polyacid chlorides (e.g. from acrylic acid) or polyanhydrides (e.g. from maleic anhydride). Comparable products may also be prepared from cyanine and other dyes.

Particularly interesting sensitizers usable according to the invention include cofacial phthalocyanine derivatives, including oligomers and polymers. These are materials that are linked through the element in the center of the Pc molecule, and this element accordingly needs to be tri- (e.g. Al, Ga) or tetravalent (e.g. Si, Ge, Sn) in order to have axial groups available for linkage. Only the tetravalent elements would have the two axial groups needed for polymerization. Any groups could be present at the periphery of the Pc system (e.g. —$SO_3Na$) provided that they would not interfere with the polymerization chemistry, hence products of this type could be either ionic or nonionic (or have the potential to be made so). Hence, for the Si compound:

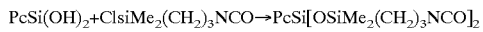

This diisocyanate forms polyurethane oligomers and polymers with diols e.g. ethylene glycol and other $HO(CH_2)_nOH$, or with $HO(CH_2CH_2O)_nH$ (PEG), and it could also be reacted with analogous diamines to form polyureas.

The corresponding isothiocyanate can also be prepared and similar chemistry performed.

AlPc compounds could not be used for polymeric products having more than two chromophores, but two such molecules could be cofacially linked, using chemistry analogous to that described above, to produce the dimeric product which is a polychromophore for the purposes of this text.

Vectors

As mentioned above, the sensitizers and contrast agents may passively target tumor tissue or cells or may be conjugated to an active targeting moiety, a "vector", which serves to modify their biodistribution pattern, e.g. to prolong blood residence times and so allow accumulation at tumor sites over several passes or allow greater penetration of the sensitizer through the vasculature or to bind the sensitizer to receptors at tumor cell surfaces or to other receptors which are more abundant in regions of tumor growth. Appropriate vectors include antibodies, antibody fragments, receptor-binding peptides and peptoids, tumor-targeting drug compounds, blood residence prolonging compounds, folic acid and derivatives thereof, and the like. Transferrin is a particularly suitable vector for targetting a chromophore to a growing tumor due to the general up-regulation of transferrin receptors at growing tumors.

Vectors and their attachment, for example using bifunctional linker compounds, have been widely described in relation to contrast agents for MRI and scintigraphy and in relation to targeted radiopharmaceuticals in general. See for example "Handbook of targeted delivery of imaging agents", Ed. V. P. Torchilin, CRC, Boca Raton, USA, 1995.

These vectors are typically macromolecular and may be directly linked to the rest of the sensitizer or contrast agent or, in those cases where this interferes with the targeting capability of the vector, an intermediate molecule, or linker, may be used.

Optionally, compounds of this invention can be attached to a targeting vector so as to allow the compounds to accumulate in certain locations of the body such as specific organs, parts of spsecific organs or diseased tissue. Methods for attachment are taught in WO 96/40285, priority applications U.S. Ser. No. 08/497,684 now abandoned and U.S Ser. No. 08/640,464, and in U.S. ser. No. 08/392,614 now U.S. Pat. No. 5,760,191 issued Jun. 2, 1998.

The term "residue" is used herein in context with a chemical entity. Said chemical entity comprises, for example, a vector moiety, or a dye, or a linking group, or a vector reactive group, or an receptor recognizing group, or an immunoreactive material, or an immunoreactive protein, or an antibody, or an antibody fragment, or a protein, or a peptide, or a small organic molecule, or a cross-linking agent such as a heterobifunctional cross-linking agent, or a spacing group. The term "residue" is defined as that portion of said chemical entity which exclusively remains when one or more chemical bonds of which said chemical entity is otherwise comprised when considered as an independent chemical entity, are altered, modified, or replaced to comprise one or more covalent bonds to one or more other chemical entities.

As used herein, the terms "receptor" and "antigen" refer to a chemical group in a molecule which comprises an active site in said molecule, or to an array of chemical groups in a molecule which comprise one or more active sites in said molecule, or to a molecule comprised of one or more chemical groups or one or more arrays of chemical groups, which group or groups or array of groups comprise one or more active sites in said molecule. An "active site" of a receptor has a specific capacity to bind to or has an affinity for binding to a vector. With respect to use with the term "receptor" or with the term "active site in a receptor", the term "vector" as used herein refers to a molecule comprised of a specific chemical group or a specific array of chemical groups (receptor recognizing group) which molecule, group, or array of groups is complementary to or has a specific affinity for binding to a receptor, especially to an active site in a receptor, or which otherwise modifies the biodistribution of the overall composition of matter in a desired manner. Examples include cell surface antigens, cell surface and intracellular receptors which bind hormones; and cell surface and intracellular receptors which bind drugs. The sites of specific association of specific binding of hormones to said cellular receptors; and of specific binding of drugs to cellular receptors are examples of active sites of said receptors, and the hormones, or the drugs are examples of vectors for the respective receptors.

The vector group, $V_e$, can be selected from a wide variety of naturally occurring or synthetically prepared materials, including, but not limited to enzymes, amino acids, peptides, polypeptides, proteins, lipoproteins, glycoproteins, lipids, phospholipids, hormones, growth factors, steroids, vitamins, polysaccharides, lectins, toxins, nucleic acids (including oligonucleotides), haptens, avidin and derivatives thereof, biotin and derivatives thereof, antibodies (monoclonal and polyclonal), anti-antibodies, antibody fragments and antigenic materials (including proteins and carbohydrates). The vector group, $V_e$, can be also be selected from, but not limited to, components or products of viruses, bacteria, protozoa, fungi, parasites, rickettsia, molds, as well as animal and human blood, tissue and organ components. Furthermore, the vector group, $V_e$, can be a pharmaceutical drug or synthetic analog of any of the materials mentioned above as well as others known to one skilled in the art. Additional specific vector groups are described in WO 96/40285 which is incorporated herein in its entirety.

The vector, V, preferably is an antibody, antibody fragment, protein or peptide which recognizes and is specific for a tumor associated antigen or receptor. In some embodiments, V can contain a receptor recognizing group covalently bonded thereto through a chemical bond or a linking group derived from the residue of a receptor recognizing group and the residue of a reactive group on V. As used herein, the term "receptor recognizing group" which can be abbreviated by "RRG" also includes an organic compound which is capable of covalently bonding the vector and which is found in a living organism or is useful in the diagnosis, treatment or genetic engineering of cellular material or living organisms, and which has a capacity for interaction with another component ("active site" of a receptor) which may be found in biological fluids or associated with cells to be treated such as tumor cells.

The RRG can be selected from the same wide variety of naturally occurring or synthetically prepared materials mentioned above. In addition, an RRG can be any substance which when presented to an immunocompetent host will result in the production of a specific antibody capable of binding with that substance, or the antibody so produced, which participates in an antigen-antibody reaction.

Preferred vectors are antibodies and various immunoreactive fragments thereof, proteins and peptides as long as they contain at least one reactive site for reaction with a vector reactive group or with linking groups (L) as described herein. That site can be inherent to the vector or it can be introduced through appropriate chemical modification of the vector. In addition to antibodies and fragments produced by the techniques outlined herein, other antibodies, proteins, and peptides produced by the techniques of molecular biology, phage display, and genetic engineering are specifically included.

As used herein, the term "antibody fragment" refers to a vector which comprises a residue of an antibody, which antibody characteristically exhibits an affinity for binding to an antigen. The term affinity for binding to an antigen, as used herein, refers to the thermodynamic expression of the strength of interaction or binding between an antibody combining site and an antigenic determinant and, thus, of the stereochemical compatibility between them; as such, it is the expression of the equilibrium or association constant for the antibody-antigen interaction. The term affinity, as used herein, also refers to the thermodynamic expression of the strength of interaction or binding between a ligand and a receptor and, thus, of the stereochemical compatibility between them; as such, it is the expression of the equilibrium or association constant for the ligand/receptor interaction.

Antibody fragments exhibit at least a percentage of said affinity for binding to said antigen, said percentage being in the range of 0.001 per cent to 1,000 per cent, preferably 0.01 per cent to 1,000 per cent, more preferably 0.1 per cent to 1,000 per cent, and most preferably 1.0 per cent to 1,000 per cent, of the relative affinity of said antibody for binding to said antigen.

An antibody fragment can be produced from an antibody by a chemical reaction comprising one or more chemical bond cleaving reactions; by a chemical reaction comprising one or more chemical bond forming reactions employing as reactants one or more chemical components selected from a group comprised of amino acids, peptides, carbohydrates, linking groups as defined herein, spacing groups as defined herein, vector reactive groups as defined herein, and antibody fragments such as are produced as described herein and by a molecular biological process, a bacterial process, or by a process comprised of and resulting from the genetic engineering of antibody genes.

An antibody fragment can be derived from an antibody by a chemical reaction comprised of one or more of the following reactions:

(a) cleavage of one or more chemical bonds of which an antibody is comprised, said bonds being selected from, for example, carbon-nitrogen bonds, sulfur-sulfur bonds, carbon-carbon bonds, carbon-sulfur bonds, and carbon-oxygen bonds, and wherein the method of said cleavage is selected from:

(i) a catalysed chemical reaction comprising the action of a biochemical catalyst such as an enzyme such as papain or pepsin which to those skilled in the art are known to produce antibody fragments commonly referred to as Fab and Fab'2, respectively;

(ii) a catalysed chemical reaction comprising the action of an electrophilic chemical catalyst such as a hydronium ion which, for example, favorably occurs at a pH equal to or less than 7;

(iii) a catalysed chemical reaction comprising the action of a nucleophilic catalyst such as a hydroxide ion which, for example, favorably occurs at a pH equal to or greater than 7; and (iv) a chemical reaction comprised of a substitution reaction employing a reagent which is consumed in a stoichiometric manner such as substitution reaction at a sulfur atom of a disulfide bond by a reagent containing a sulfhydryl group;

(v) a chemical reaction comprised of a reduction reaction such as the reduction of a disulfide bond; and (vi) a chemical reaction comprised of an oxidation reaction such as the oxidation of a hydroxyl group or the oxidation of a carbon-carbon bond of a vicinal diol group such as occurs in a carbohydrate moiety; or (b) formation of one or more chemical bonds between one or more reactants, such as formation of one or more covalent bonds selected from, for example, carbon-nitrogen bonds (such as, for example, amide bonds, amine bonds, hydrazone bonds, and thiourea bonds), sulfur-sulfur bonds such as disulfide bonds, carbon-carbon bonds, carbon-sulfur bonds, and carbon-oxygen bonds, and employing as reactants in said chemical bond formation one or more reagents comprised of amino acids, peptides, carbohydrates, linking groups as defined herein, spacing groups as defined herein, vector reactive groups as defined herein, and antibody fragments such as are produced as described in (a), above; or (c) an antibody fragment can be derived by formation of one or more non-covalent bonds between one or more reactants. Such non-covalent bonds are comprised of hydrophobic interactions such as occur in an aqueous medium between chemical species that are independently comprised of mutually accessible regions of low polarity such as regions comprised of aliphatic and carbocyclic groups, and of hydrogen bond interactions such as occur in the binding of an oligonucleotide with a complementary oligonucleotide; or (d) an antibody fragment can be produced as a result of the methods of molecular biology or by genetic engineering of antibody genes, for example, in the genetic engineering of a single chain immunoreactive group, a Fv fragment or a minimal recognition unit.

An antibody fragment can be produced as a result of a combination of one or more of the above methods.

If desired, a vector can be modified or chemically altered to provide reactive groups for attaching to the residues of a receptor moiety or antigen found in or on tissues and cells of interest. Such techniques include the use of linking moieties and chemical modification such as described in WO-A-89/02931 and WO-A-89/2932, which are directed to modification of oligonucleotides, and U.S. Pat. No. 4,719,182.

The preferred uses for the sensitizers and contrast agents of the invention are for the delineation or destruction of tumors. Preferred vectors therefore include antibodies (sometimes hereinafter referred to as Ab) to tumor-associated antigens. Specific non-limiting examples include B72.3 and related antibodies (described in U.S. Pat. Nos. 4,522,918 and 4,612,282) which recognize colorectal tumors; 9.2.27 and related anti-melanoma antibodies; D612 and related antibodies which recognize colorectal tumors; UJ13A and related antibodies which recognize small cell lung carcinomas; NRLU-10, NRCO-02 and related antibodies which recognize small cell lung carcinomas and colorectal tumors (Pan-carcinoma); 7E11C5 and related antibodies which recognize prostate tumors; CC49 and related antibodies which recognize colorectal tumors; TNT and related antibodies which recognize necrotic tissue; PR1A3 and related antibodies which recognize colon carcinoma; ING-1 and related antibodies, which are described in WO-A-90/02569; B174, C174 and related antibodies which recognize squamous cell carcinomas; B43 and related antibodies which are reactive with certain lymphomas and leukemias; and anti-HLB and related monoclonal antibodies; and other tumor, tissue or cell-specific antibodies known to those skilled in the art.

More preferred vectors are proteins, especially recombinant human proteins, such as are produced or modified by molecular biological, phage display or genetic engineering techniques, which modifications comprise the independent incorporation, substitution, insertion, and deletion of specific amino acids in a peptide sequence of said protein to produce recombinant human proteins containing an RRG which has an affinity for binding to an active site of a receptor. A thus-modified recombinant protein vector has an affinity for an active site of a receptor which is greater than the affinity of the natural, unmodified, vector for the active site of the receptor.

In another embodiment, the vector (or Vector-Linker) comprises a fusion protein. As used herein, the term "fusion protein" refers to a genetically engineered material comprised of a protein whose coding region is comprised of the coding region of a residue of a first protein fused, in frame, to the coding region of a residue of a second protein. Preferably, said fusion protein is comprised of a protein whose coding region is comprised of the coding region of a residue of an RRG fused, in frame, to the coding region of one or more residues of a vector or a linker which linker can be a protein or peptide. The above genetically engineered fusion protein comprising the vector can be comprised of a protein whose coding region is independently comprised of the coding region of a residue of a human or of a non-human first protein fused, in frame, to the coding region of a residue of a human or non-human second protein. Preferably, said coding regions are independently human and bacterial or modified by genetic engineering techniques as above.

Even more preferred vectors are peptides, oligopeptides or peptoids, which vectors are composed of one or more amino acids whose sequence and composition comprise a molecule, specific chemical group or a specific array of chemical groups, which are complementary to or have a specific affinity for binding to a receptor, especially to an active site in a receptor. Such peptides may be compositionally identical to the amino acids that comprise the RRG of antibodies, antibody fragments, proteins or fusion proteins that recognize the same receptor. Alternatively, such peptidic vectors may not have an amino acid sequence identical to other RRGs but will be structurally or three-dimensionally equivalent to other RRGs that bind the same receptor. Such equivalent peptides may be identified by molecular biological techniques such as point mutation, phage display, genetic engineering and others techniques known to those skilled in the art. In addition, peptidic or oligopeptidic vectors may be designed de novo using the well-practised methodologies of computational chemistry and peptide synthesis. Synthetic peptidic vectors are not restricted to linear arrays of amino acids but may also be cyclic and contain more than one RRG per peptide. Peptide or peptoid vectors may be composed of L-amino acids, D-amino acids, non-naturally occuring amino acids, synthetic amino acid substitutes, organic molecules or mixtures of all of these, and bonded to each other by peptide (amide) or non-amide bonds.

Especially preferred vectors are peptidomimetic molecules, which molecules are fully synthetic organic materials that are the stuctural or functional equivalent of RRGs derived or identified from antibodies, antibody fragments, proteins, fusion proteins, peptides or peptoids, and that have affinity for the same receptor. Other vectors which are considered to be peptidomimetic include chemical entities, such as drugs, for example, which show affinity for the receptor, and especially the active site of the receptor, of interest. Peptidomimetic vectors may be identified through the use of molecular biological techniques such as point mutation, phage display, genetic engineering and others techniques know to those skilled in the art. Peptidomimetic vectors may be designed and synthesized de novo using current chemical methods as well as the techniques of computational chemistry and combinatorial chemistry.

As used herein, "Vector reactive group" refers to one or more chemical groups which can react with a reactive functional group typically found on or introduced into a vector, to form a bond between the linking group and the vector. It is specifically contemplated that a vector reactive group can be used to conjugate reporter and/or hydrophilic polymer moieties to a non-protein biomolecule as well as to a non-biological molecule such as a synthetic chemical substance, for example, a drug or other molecule that has an affinity for the active site of a receptor that is of interest. Vector reactive groups can also be used for the purposes of detection of such a molecule in a mixture which may contain such a synthetic chemical substance and which substance contains a group that is reactive with the vector reactive group. Thus, the vector reactive groups useful in the practice of this invention include those groups which can react with any molecule, preferably a biological molecule (such as a protein, a carbohydrate, a nucleic acid, and a lipid) containing a reactive group to form a linking group between the dye and the molecule. If the molecule is a protein, preferred reactive groups include amine groups and sulfhydryl groups. Especially preferred biological molecules contain a RRG as described above.

The vector reactive groups useful in the practice of this invention also include those groups which can react with any biological molecule that is chemically modified, for example, by oxidation, by reduction, or by covalent bond formation such as by amide bond formation with another chemical species such as, for example, an amine, an amino acid, a substituted amine, or a substituted amino acid, to introduce a reactive group into the biological molecule, to form a linking group between the reporter and/or hydrophilic polymer moieties and the chemically modified biological molecule.

Lipophilic contrast agents can be formulated for light absorption and for particle heating as oil-in-water emulsions with oil droplet sizes between 5 and 10000 nm, preferably between 10 and 2000 nm, and most preferably between 50 and 500 nm. They can be suspended in a pharmaceutically acceptable aqueous phase such as phosphate buffered saline.

Lipophilic contrast agents can be formulated as oil-in-water emulsions alone or as a mixture of more than one lipophilic contrast agent. The percentage of a single lipophilic contrast agent in a mixture of lipophilic contrast agents can be as low as 0.1% and as high as 99.9%.

The oil-in-water emulsions droplets may be composed exclusively of radiation absorbing components or may include other lipophilic substances distributed throughout the droplet. These emulsions can contain pharmaceutically acceptable excipients known in the art including lecithin, phospholipids such as those available from Larodan Lipids, surfactants such as the Tetronics and Pluronics, lipophilic additives such as sesame oil, and those components normally used to adjust and control isotonicity, pH and osmolality.

In a preferred embodiment, the oil-in-water emulsions droplets may contain polyethylene oxide based surfactants, preferably nonionic polyethylene oxide based surfactants. These surfactants can optionally behave as stabilizers for the oil-in-water emulsions droplets. The concentration of these surfactants can range from 0.0001% to as much as 25% of the emulsion, preferably from 0.01% to about 5%. In addition, upon treatment with oxygen, such as by exposure to oxygen in air, they can react to form one or more hydroperoxide species.

Preferred vector reactive groups can be selected from, but are not limited to, groups that will react directly with an amine group such as a lysine epsilon amine group or a terminal amine group in a protein or peptide or with a sulfhydryl group such as a cysteine sulfhydryl group commonly found on a protein or other biological molecule. Examples of such protein reactive groups include active halogen-containing groups such as chloromethylphenyl groups, chloromethylcarbonyl groups, and iodomethylcarbonyl groups; activated 2-(leaving group)-substituted ethylsulfonyl and ethylcarbonyl groups such as 2-chloroethylsulfonyl groups and 2-chloroethylcarbonyl groups; vinylsulfonyl groups; vinylcarbonyl groups; oxiranyl groups; isocyanato groups; isothiocyanato groups; aldehydo groups; aziridyl groups; succinimidoxycarbonyl groups; activated acyl groups such as carboxylic acid halide groups; anhydride groups; thioester groups; carbonates such as nitrophenylcarbonates; sulfonic acid esters and chlorides; phosphoramidates; cyanuric monochlorides and cyanuric dichlorides; and other groups known to be useful in conventional photographic gelatin hardening agents.

The above listed vector reactive groups can react with a protein or vector which is chemically modified to contain reactive amine groups and sulfhydryl groups.

Amine groups can be introduced by well known techniques such as, for example, nitration of an aromatic group followed by reduction, by conversion of a primary amide to an amine by reduction, by conversion of a hydroxyl group of an alcohol into a sulfonic acid ester followed by displacement with an azide group and subsequent reduction to an amine, and the like. Sulfhydryl groups can be introduced by well known techniques such as, for example, by conversion of a hydroxyl group of an alcohol into a sulfonic acid ester followed by displacement with sodium hydrosulfide, by dehydrative amide bond formation between an amine group of a protein and a carboxylic acid group of an acetylated cysteine using a carbodiimide reagent, and the like.

In addition, when a protein, peptide, peptoid or peptidomimetic can be chemically modified such as by partial oxidation to introduce an aldehyde group or a carboxylic acid group, a preferred vector reactive group can be selected from amino, aminoalkyl, aminoaryl, alkylamino, arylamino, hydrazino, alkylhydrazino, arylhydrazino, carbazido, semicarbazido, thiocarbazido, thiosemicarbazido, sulfhydryl, sulfhydrylalkyl, sulfhydrylaryl, hydroxy, carboxy, carboxyalkyl and carboxyaryl. The alkyl portions of the protein reactive group can contain from 1 to about 20 carbon atoms, and the aryl portions of the protein reactive group can contain from about 6 to about 24 carbon atoms.

An additional preferred vector reactive group can comprise a residue of a crosslinking agent. A useful crosslinking agent can react with a functional group such as, for example, an amine or sulfhydryl or carboxylic acid group or aldehyde group found in a linker and with a functional group such as, for example, an amine or sulfhydryl or carboxylic acid group or aldehyde group found in a vector or in a chemically modified protein or biological molecule such as described above. The residues of certain useful crosslinking agents, such as, for example, difunctional gelatin hardeners, bisepoxides and bisisocyanates become a part of, i.e. a linking group in, a conjugate which is formed as a result of the crosslinking reaction of such a crosslinking vector reactive group with a reporter and/or a hydrophilic polymer moiety. Vector reactive groups derived from various heterobifunctional cross-linking reagents such as those listed in the Pierce Chemical Company Catalog and handbook—Protein Modification Section, (1994/5) are useful and non-limiting examples of such reagents include:

Sulfo-SMCC: Sulfosuccinimidyl 4-(N-maleimidomethyl) cyclohexane-1-carboxylate

Sulfo-SIAB: Sulfosuccinimidyl(4-iodoacetyl) aminobenzoate.

Sulfo-SMPB: Sulfosuccinimidyl 4-(p-maleimidophenyl) butyrate.

2-IT: 2-Iminothiolane.

SATA: N-Succinimidyl S-acetylthioacetate.

Other useful crosslinking agents, however, facilitate the crosslinking, for example, as consumable catalysts, and are not present in the final conjugate. Examples of such crosslinking agents are carbodiimide and carbamoylonium crosslinking agents as disclosed in U.S. Pat. No. 4,421,847, the disclosure of which is hereby incorporated herein by reference in its entirety, and the dication ethers of U.S. Pat. No. 4,877,724, the disclosure of which is hereby incorporated herein by reference in its entirety. With these crosslinking agents, one of the reactants must have a carboxyl group and the other an amine or sulfhydryl group. The crosslinking agent first reacts selectively with the carboxyl group, preferably a carboxyl group on a vector, then is split out during reaction of the "activated" carboxyl group with an amine, preferably an amine group of a linker, to form an amide bond between the vector and a hydrophilic polymer and/or reporter, thus covalently bonding the moieties. An advantage of this approach is that crosslinking of like molecules, e.g., dye with dye, can be avoided, whereas the reaction of bifunctional crosslinking agents is nonselective so that unwanted crosslinked molecules can be obtained.

Additional preferred vector reactive groups include semicarbazido; thiocarbazido; thiosemicarbazido; isocyanato and isothiocyanato; vinyl sulfonylalkyloxy, the alkylene group of which preferably contains from 2 to 10 carbon atoms; vinyl sulfonylalkylpoly(oxyalkyl)oxy, the alkylene group of the sulfonylalkyl portion of which preferably contains from 2 to 10 carbon atoms; the alkylene group of the polyoxyalkyl portion preferably contains from 2 to 10 carbon atoms, such poly(oxyalkyl) portion preferably comprising a poly(oxyethylene) group or a poly(oxyethylene)-co-poly(oxypropylene) copolymer group, and the polymer contains from 2 to about 100 monomeric oxyalkylene units; amidoalkyloxy, the alkylene group of which preferably contains from 1 to 10 carbon atoms; hydrazidoalkyloxy, the alkylene group of which preferably contains from 1 to 10 carbon atoms; azidocarbonylalkyloxy, the alkylene group of which preferably contains from 1 to 10 carbon atoms; aryloxycarbonyloxyalkyloxy, the alkylene group of which preferably contains from 2 to 10 carbon atoms, and the aryl group of which is as described above; aryloxycarbonyl(polyoxyalkyl)oxy, the aryl group of which is as described above, and the alkylene group of the polyoxyalkyl portion preferably contains from 2 to 10 carbon atoms and is as described above, such poly(oxyalkyl) portion preferably comprising a poly(oxyethylene) group or a poly(oxyethylene)-co-poly(oxypropylene) copolymer group, and the polymer contains from 2 to about 100 monomeric oxyalkylene units; triazines such as 4,6-dichloro-2-triazinylamino, 4,6-dichloro-2-triazinyloxy, 4,6-dichlorotriazinyl-2-oxy(polyalkyloxy), 4-alkoxy-6-chloro-2-triazinyloxy, and 4-alkoxy-6-chloro-2-triazinyl(polyoxyalkyl)oxy, the alkyl groups of the alkoxy portions preferably each containing from 2 to 10 carbon atoms, and the alkylene groups of the polyoxyalkyl portions preferably each containing from 2 to 10 carbon atoms, such a poly(oxyalkyl) portion preferably comprising a poly(oxyethylene) group or a poly(oxyethylene)-co-poly(oxypropylene) copolymer group, in which the polymer contains from 2 to about 100 monomeric oxyalkylene units; formylalkyl, the alkyl group of which preferably contains from 1 to 10 carbon atoms; aminoalkyl, the alkyl group of which preferably contains from 1 to 10 carbon atoms; active esters, for example, succinimidoxycarbonyl; active anhydrides and mixed anhydrides; active carbonates such as arylcarbonatoaryl, alkylcarbonatoaryl, arylcarbonatoalkyl, and alkylcarbonatoalkyl, the alkyl groups of which preferably contain from 2 to 10 carbon atoms and are as described above, and the aryl groups of which are preferably comprised of a six membered ring containing electron withdrawing substituents such as, for example, nitro and halogen, and optionally containing water solubilizing groups such as a sulfonate salt; sulfhydryl; sulfhydrylalkyl, the alkyl group of which preferably contains from 1 to 10 carbon atoms; thioalkylcarbonylaminoalkyloxy, the alkylene group of the thioalkylcarbonyl portion preferably containing from 1 to 10 carbon atoms, and the alkylene group of the aminoalkyloxy portion preferably containing from 2 to 10 carbon atoms; maleimidoalkylcarbonylaminoalkyloxy, the alkylene group of the maleimidoalkylcarbonyl portion preferably containing from 1 to 10 carbon atoms, and the alkylene group of the aminoalkyloxy portion preferably containing from 2 to 10 carbon atoms; azido; iodoalkylcarbonylamino, the alkylene group of which contains from 1 to 10 carbon atoms; amidatoalkylamino, the alkylene group of which contains from 1 to 10 carbon atoms; and amidatoarylalkylamino, the alkylene group of which contains from 1 to 10 carbon atoms, and the aryl group of which is as described above.

Thus it will be realised that the hydrophilic polymer moiety in the sensitizers and/or contrast agents used according to the invention may function as a linker moiety as well as as a vector moiety and as a senzitizer.

The residues of the vector may be linked to the other components of the conjugates used according to this invention through a chemical bond or a linking group. Preferred linking groups may be derived from vector reactive groups and so include nitrogen atoms in groups such as amino, imido, nitrilo and imino groups; alkylene, preferably containing from 1 to 18 carbon atoms such as methylene, ethylene, propylene, butylene and hexylene, such alkylene optionally being interrupted by 1 or more heteroatoms such as oxygen, nitrogen and sulfur or heteroatom-containing groups; carbonyl; sulfonyl; sulfinyl; ether; thioether; ester, i.e., carbonyloxy and oxycarbonyl; thioester, i.e., carbonylthio, thiocarbonyl, thiocarbonyloxy, and oxythiocarboxy; amide, i.e., iminocarbonyl and carbonylimino; thioamide, i.e., iminothiocarbonyl and thiocarbonylimino; thio; dithio; phosphate; phosphonate; urelene; thiourelene; urethane, i.e., iminocarbonyloxy, and oxycarbonylimino; an amino acid linkage, i.e. a

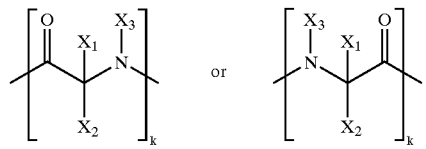

group wherein k=1 and $X_1$, $X_2$, $X_3$ independently are H, alkyl, containing from 1 to 18, preferably 1 to 6 carbon atoms, such as methyl, ethyl and propyl, such alkyl optionally being interrupted by 1 or more heteroatoms such as oxygen, nitrogen and sulfur, substituted or unsubstituted aryl, containing from 6 to 18, preferably 6 to 10 carbon atoms such as phenyl, hydroxyiodophenyl, hydroxyphenyl, fluorophenyl and naphthyl, aralkyl, preferably containing from 7 to 12 carbon atoms, such as benzyl, heterocyclyl, preferably containing from 5 to 7 nuclear carbon and one or more heteroatoms such as S, N, P or O, examples of preferred heterocyclyl groups being pyridyl, quinolyl, imidazolyl and thienyl; heterocyclylalkyl, the heterocyclyl and alkyl portions of which preferably are described above; or a peptide linkage, i.e. a

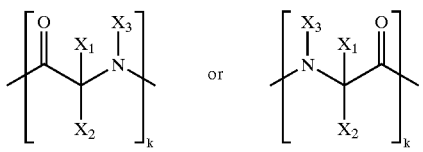

group wherein k>1 and each X independently is represented by a group as described for $X_1$, $X_2$, $X_3$ above. Two or more linking groups can be used, such as, for example, alkyleneimino and iminoalkylene. It is contemplated that other linking groups may be suitable for use herein, such as linking groups commonly used in protein heterobifunctional and homobifunctional conjugation and crosslinking chemistry as described above. Especially preferred linking groups include amino groups which when linked to the residue of a dye via an isothiocyanate group on the dye form thiourea groups.

The linking groups can contain various substituents which do not interfere with the coupling reaction between the various components of the conjugates used according to this invention. The linking groups can also contain substituents which can otherwise interfere with such reaction, but which during the coupling reaction, are prevented from so doing with suitable protecting groups commonly known in the art and which substituents are regenerated after the coupling reaction by suitable deprotection. The linking groups can also contain substituents that are introduced after the coupling reaction. For example, the linking group can be substituted with substituents such as halogen, such as F, Cl, Br or I; an ester group; an amide group; alkyl, preferably containing from 1 to about 18, more preferably, 1 to 4 carbon atoms such as methyl, ethyl, propyl, i-propyl, butyl, and the like; substituted or unsubstituted aryl, preferably containing from 6 to about 20, more preferably 6 to 10 carbon atoms such as phenyl, naphthyl, hydroxyphenyl, iodophenyl, hydroxyiodophenyl, fluorophenyl and methoxyphenyl; substituted or unsubstituted aralkyl, preferably containing from 7 to about 12 carbon atoms, such as benzyl and phenylethyl; alkoxy, the alkyl portion of which preferably contains from 1 to 18 carbon atoms as described for alkyl above; alkoxyaralkyl, such as ethoxybenzyl; substituted or unsubstituted heterocyclyl, preferably containing from 5 to 7 nuclear carbon and heteroatoms such as S, N, P or O, examples of preferred heterocyclyl groups being pyridyl, quinolyl, imidazolyl and thienyl; a carboxyl group; a carboxyalkyl group, the alkyl portion of which preferably contains from 1 to 8 carbon atoms; or the residue of a dye.

SDT and Imaging

Where the method of the invention involves administration of a reporter-containing sonodynamic therapy agent, the dosage used will depend on the mode of administration, the nature of the condition being imaged, the patient's size and species, the nature of the imaging modality, and the nature of the reporter. Where the reporter is a non-radioactive metal ion, generally dosages of from 0.001 to 5.0 mmoles of chelated imaging metal ion per kilogram of patient bodyweight are effective to achieve adequate contrast enhancements. For most MRI applications preferred dosages of imaging metal ion will be in the range of from 0.02 to 1.2 mmoles/kg bodyweight while for X-ray applications dosages of from 0.05 to 2.0 mmoles/kg are generally effective to achieve X-ray attenuation. Preferred dosages for most X-ray applications are from 0.1 to 1.2 mmoles of the lanthanide or heavy metal compound/kg bodyweight. Where the reporter is a radionuclide, dosages of 0.01 to 100 mCi, preferably 0.1 to 50 mCi will normally be sufficient per 70 kg bodyweight. Where the reporter is a superparamagnetic particle, the dosage will normally be equivalent to 0.5 to 30 mg Fe/kg bodyweight. Where the reporter is a gas or gas generator, e.g. in a microballoon, the dosage will normally be equivalent to 0.05 to 100 $\mu$L gas per 70 kg bodyweight. Where the reporter is a light absorbing chromophore, the dosage will normally be in the range of 0.001 mmoles of chromophore/kg to 2.0 mmoles of chromophore/kg bodyweight when normalized to an absorbtivity of 100,000. Depending on the method of application of the imaging agent, the dosage can be adjusted downward by as much as four orders of magnitude. For example, if the agent were to be injected directly into a diseased tissue or if it were to be applied topically to a diseased tissue such as endometriotic tissue, dosage levels calculated relative to whole bodyweight could be substantially reduced as a function of the size or weight or area of the diseased tissue relative to the entire body.

The reporter containing sonodynamic therapy agents used according to the invention may be administered by any convenient route, for example by injection or infusion into muscle, tumor tissue, or the vasculature, subcutaneously, or interstitially, by administration into an externally voiding body cavity (e.g. into the digestive tract (for example orally or rectally), vagina, uterus, bladder, ears, nose or lungs), by transdermal administration (e.g. by iontophoresis or by topical application), or by topical application to a surgically exposed site. Direct injection into a tumor is one preferred administration route.

In general, however, parenteral administration, e.g. of a solution or dispersion of or containing the reporter containing sonodynamic therapy agent will be preferred.

The administration forms used may be any of the forms conventionally used for administration of pharmaceuticals, e.g. solutions, suspensions, dispersions, syrups, powders, tablets, capsules, sprays, creams, gels, etc.

The reporter containing sonodynamic therapy agent, if water-soluble, can be administered in the form of an aqueous solution. Alternatively, and in many cases preferably, the sensitizer or contrast agent may be presented in particulate form, e.g. liquid droplets of or containing the sensitizer or contrast agent (e.g. in solution in a water-immiscible fluid), or solid or semi-solid particles of, containing or coated with the sensitizer or contrast agent. This latter category includes vesicles (e.g. liposomes, micelles or microballoons) containing the sensitizer or contrast agent.

Where the reporter containing sonodynamic therapy agent is particulate, the other particle components, e.g. matrix or membrane forming materials, coating agents, contrast agents, solvents, gases or gas generators, etc, will conveniently be materials which are physiologically tolerable at the dosages used. The formation of droplets, coated particles, composite particles, vesicles, etc is well described in the literature, especially that relating to pharmaceutical and contrast agent (e.g. ultrasound contrast agent) preparation and formulation.

Reporter containing sonodynamic therapy agents may be administered via the oral route for absorption through the lining of the stomach, the intestines, and the colon, see for example, Carrier-mediated intestinal transport of drugs, Tsuji, A.; Tamai, I., Pharmaceutical Research (New York) Vol. 13, No. 7, p. 963–977, 1996; Oral protein drug delivery, Wang, Wei, J. Drug Targeting Vol. 4, No. 4, 1996, pp. 195–232; Improved passive oral drug delivery via prodrugs, Taylor, Michael D., Adv. Drug Delivery Rev. Vol. 19, No. 2, 1996, pp. 131–148; Oral colon-specific drug delivery: a review, Van den Mooter, Guy; Kinget, Renaat, Drug Delivery, Vol. 2, No. 2, 1995, pp. 81–93; Present status of controlled drug delivery system-overview, Naik, S. R.; Shanbhag, V., Indian Drugs, Vol. 30, No. , September 1993, pp. 423–429; Novel formulation strategies for improving "oral" bioavailability of drugs with poor membrane permeation or presystemic metabolism, Aungst, B. J., Journal of Pharmaceutical Sciences (USA), Vol. 82, No. October 1993, pp. 979–987; Remington's Pharmaceutical Sciences, A. Osol, ed., Mack Publishing Co. 1975, Part 6, chp 40 and references therein. (pp 731–753), Part 8, all chps (pp 1355–1644); The Extra Pharmacopoeia, Martindale, 29th Edition, The Pharmaceutical Press, London, 1989.

Administration of drugs and other agents by the oral route is often preferred due to enhanced patient compliance (for repeated dosing) and ease of administration. It is well known in the art that not every agent is bioavailable via this route; that is to say, that not all molecules are 1) chemically stable in the environs of the gut, 2) transportable across alimentary membranes for absorption into the blood/lymphatics, and 3) active even if accessible due to metabolic processes within the gut or possible solubility issues, etc. However, it is also known in the art, that alteration of the molecular structure to control the relative hydrophobicity of the molecule (i.e., partition coefficient between octanol and water; log(P)) within a preferred range can increase the oral availability of the agent.

Agents can also be administered via body cavities such as the mouth, the rectum, the vagina, the peritoneal cavity (e.g., intraperitoneal injection), etc. as well as topical, intramuscular, subcutaneous, and pulmonary administration. All of the known routes of administration of drugs/agents to mammals are envisaged according to the present invention.

The reporter containing sonodynamic therapy agents can be injected into the vasculature prior to or during SDT. For detection of lymph nodes it can be injected into a lymph duct draining into the SDT target area. Alternatively it may be applied during SDT as a topical ointment, a liquid, or a spray.

The dosage of the reporter containing sonodynamic therapy agents in the methods of the invention will depend upon the condition being treated and the materials and imaging modalities used, but in general will be of the order of from 1 pmol/kg to 1 mmol/kg bodyweight.

The reporter containing sonodynamic therapy agents for use in the present invention may be formulated with conventional pharmaceutical or veterinary aids, for example emulsifiers, fatty acid esters, gelling agents, stabilizers, antioxidants, osmolality adjusting agents, buffers, pH adjusting agents, etc., and may be in a form suitable for parenteral or enteral administration, for example injection or infusion or administration directly into a body cavity having an external escape duct, for example the gastrointestinal tract, the bladder or the uterus. Thus the compounds of the present invention may be in conventional pharmaceutical administration forms such as tablets, capsules, powders, solutions, suspensions, dispersions, syrups, suppositories etc. However, solutions, suspensions and dispersions in physiologically acceptable carrier media, for example water for injections, will generally be preferred.

For some portions of the body, the most preferred mode for administering the sensitizer agents is parenteral, e.g., intravenous administration. Parenterally administrable forms, e.g. intravenous solutions or dispersions, should be sterile and free from physiologically unacceptable agents, and should have low osmolality to minimize irritation or other adverse effects upon administration, and thus the composition administered should preferably be isotonic or slightly hypertonic. Suitable vehicles include aqueous vehicles customarily used for administering parenteral solutions or dispersions such as Sodium Chloride Injection, Ringer's Injection, Dextrose Injection, Dextrose and Sodium Chloride Injection, Lactated Ringer's Injection and other solutions such as are described in Remington's Pharmaceutical Sciences, 15th ed., Easton: Mack Publishing Co., pp. 1405–1412 and 1461–1487 (1975) and The National Formulary XIV, 14th ed. Washington: American Pharmaceutical Association (1975). The solutions or dispersions can contain preservatives, antimicrobial agents, buffers and antioxidants conventionally used for parenteral solutions, excipients and other additives which are compatible with the sensitizers or contrast agents and which will not interfere with manufacture, storage or use.

In the methods of the invention, the sonodynamic therapy may be effected by exposure of the patient to an effective amount of ultrasound acoustic energy as described in the literature. Generally this will involve exposure to focused ultrasound, e.g. at a power level of 0.1 to 20 $Wcm^{-2}$, preferably 4 to 12 $Wcm^{-2}$, a frequency of 0.01 to 10.0 MHz, preferably 0.1 to 5.0 MHz, particularly 0.01 to 2.2 MHz, for periods of 10 milliseconds to 60 minutes, preferably 1 second to 2 minutes. Particularly preferably the patient is exposed to ultrasound at an acoustic power of 5mW to 10 W with a fundamental frequency of 0.01 to 1.2 MHz and a corresponding second harmonic frequency, as this reduces the exposure necessary to achieve a cytopathogenic effect (see for example Umemura et al. 1995, IEEE Ultrasonics Symposium, pages 1567–1570, Umemura et al., IEEE Trans. Ultrasonics, Ferroelectrics and Freq. Control 43: 1054–1062 (1996) and Kawabara et al. Ultrasonics Sonochemistry 3: 1–5 (1996)). Optionally, the ultrasound can be administered in continuous wave or pulsed mode over the period of administration.

The sensitizer agent used in the methods according to the present invention may contain a single sensitizer material or it may contain a plurality of sensitizer materials as discussed above. When there is a plurality of sensitizer materials these may be administered separately, sequentially or simultaneously. Likewise the sensitizer agent may contain a further component which is detectable in a diagnostic imaging modality, e.g. contrast agents such as gas containing vesicles, soluble or insoluble paramagnetic metal or metal radionuclide chelates or iodinated organic X-ray contrast agents, superparamagnetic particles (e.g. nanoparticles), etc. Again such contrast agents may be administered separately, sequentially or simultaneously.

It has also been realised that particulate materials, i.e. solid particles or liquid droplets, may be used as sensitizers in SDT and this forms a further aspect of the invention. Viewed from this aspect the invention provides a method of treatment of the human or animal body (e.g. a vascularized mammalian, avian or reptilian body) by sonodynamic therapy in which a sensitizer agent is administered to said body and said body is exposed to ultrasound to achieve a cytopathogenic effect at a site (e.g. a tumor site) therein, wherein the said sensitizer agent is a physiologically tolerable solid particulate or liquid droplet containing material.

In this method, the particulate is preferably solid and particularly preferably has a mean particle size of 5 nm to 12 μm, the upper end of this range being usable essentially only with deformable solid particles. More highly preferred particle sizes are in the range 100 nm to 5 μm. The particles need not, but preferably will be associated with a water soluble polymer material, e.g. having such a material bound to or associated with a surface of the particles or being in solution in an aqueous dispersion medium for the particles. The particles need not but preferably do include or consist of a chromophore material, e.g. a dye compound as discussed above, e.g. a cyanine, phthalocyanine, naphthalocyanine, triphenylmethane or porphyrin.

Optionally the particles may contain or consist of an iodinated X-ray contrast agent, e.g. a water insoluble solid or liquid triiodophenyl group containing compound and superparamagnetic particulates of type proposed as MR contrast agents.

Such particles, if desired may be coupled to vector moieties as discussed above to actively target the particles to the SDT treatment site.

In a further aspect the invention provides the use of a physiologically tolerable solid particulate or liquid-droplet containing material for the manufacture of a sensitizer composition for use in a method of sonodynamic therapy.

It has also been realised that phthalocyanines and analogous aryl-linker-aryl (where "linker" is a multiply unsaturated carbon chain with alternating single and multiple carbon carbon bonds, optionally carrying pendant or fused ring substituent) chromophores, herein referred to as phthalocyaninoids, are particularly suited to use as sensitizers in SDT. Thus viewed from a yet further aspect the invention provides a method of treatment of the human or animal body (e.g. a vascularized mammalian, avian or reptilian body) by sonodynamic therapy in which a sensitizer agent is administered to said body and said body is exposed to ultrasound to achieve a cytopathogenic effect at a site (e.g. a tumor site) therein, wherein the sensitizer agent is a physiologically tolerable phthalocyanine or phthalocyaninoid compound, preferably a compound comprising a water-soluble polymer moiety and/or a lipophilic group as defined above.

Viewed from a still further aspect the invention provides the use of physiologically tolerable phthalocyanine or phthalocyaninoid compound, preferably a compound comprising a water soluble polymer moiety and/or a lipophilic group as defined above, for the manufacture of a sensitizer composition for use in SDT.

It has also been realised that cyanines and analogous aryl-linker-aryl (where "linker" is a multiply unsaturated carbon chain with alternating single and multiple carbon carbon bonds, optionally carrying pendant or fused ring substituent) chromophores, herein referred to as cyaninoids, are particularly suited to use as sensitizers in SDT. Thus viewed from a yet further aspect the invention provides a method of treatment of the human or animal body (e.g. a vascularized mammalian, avian or reptilian body) by sonodynamic therapy in which a sensitizer agent is administered to said body and said body is exposed to ultrasound to achieve a cytopathogenic effect at a site (e.g. a tumor site) therein, wherein the sensitizer agent is a physiologically tolerable cyanine or cyaninoid compound, preferably a compound comprising a water-soluble polymer moiety and/or a lipophilic group as defined above.

Viewed from a still further aspect the invention provides the use of physiologically tolerable cyanine or cyaninoid compound, preferably a compound comprising a water soluble polymer moiety and/or a lipophilic group as defined above, for the manufacture of a sensitizer composition for use in SDT.

Moreover as described above it has been realised that the SDT treatment may be used to activate a free radical contrast agent, e.g. by converting a radical precursor to a free radical (preferably a persistent free radical with a half life in the patient's body of at least 1 minute). Such free radicals may function as image contrast enhancing agents in imaging modalities such as MRI, Overhauser-MRI, and esr imaging. Examples of agents which can be activated in this way include trityls, in particular the OMRI agents disclosed in the patent publications of Nycomed Innovation and Hafslund Nycomed Innovation. Thus viewed from a further aspect the invention provides a method of generating an image of a human or non-human animal body which comprises administering to said body a physiologically tolerable material and generating using an imaging technique sensitive to the presence of free radicals an image of at least part of said body to which said material distributes, comprising using as said material a free radical precursor and exposing said body to ultrasound of a power and frequency sufficient to generate free radicals from said precursor.

Viewed from a further aspect the invention also provides the use of a physiologically tolerable free radical precursor for the manufacture of a contrast agent composition for use in a method of treatment or diagnosis involving administration of said composition and subsequent generation of free radicals from said precursor by the application of ultrasound.

This method provides a way by which the SDT may be imaged as the cytopathogenic effects of SDT occur in the regions in which the free radicals are generated and as the free radicals will cause modification (e.g. intensification) of the parts of the image corresponding to the sites where SDT is taking place.

Besides trityls and other radicals as mentioned above, the radicals responsible for image modification may be chromophores such as cyanines, azo dyes, porphyrins, etc. or other SDT sensitizer compounds.

BRIEF DESCRIPTION OF THE DRAWINGS

FIG. 1 presents a comparison of the effects of ultrasound on suspensions of HL-60 cells in the absence and presence of chloroaluminum phthalocyanine tetrasulfonate. This is described in more detail hereinafter.

FIG. 2A is a graph of comparative biodistribution data of contrast agent Polymer 3 (NC100448) versus indocyanine green as control in female immunodeficient mice containing HT-29 tumors at one hour post intravenous injection of phosphate buffered saline solutions of each. Polymer 3 is detected in the tumor; the control compound is negligibly detected.

DETAILED DESCRIPTION OF THE INVENTION

Figure 2B:
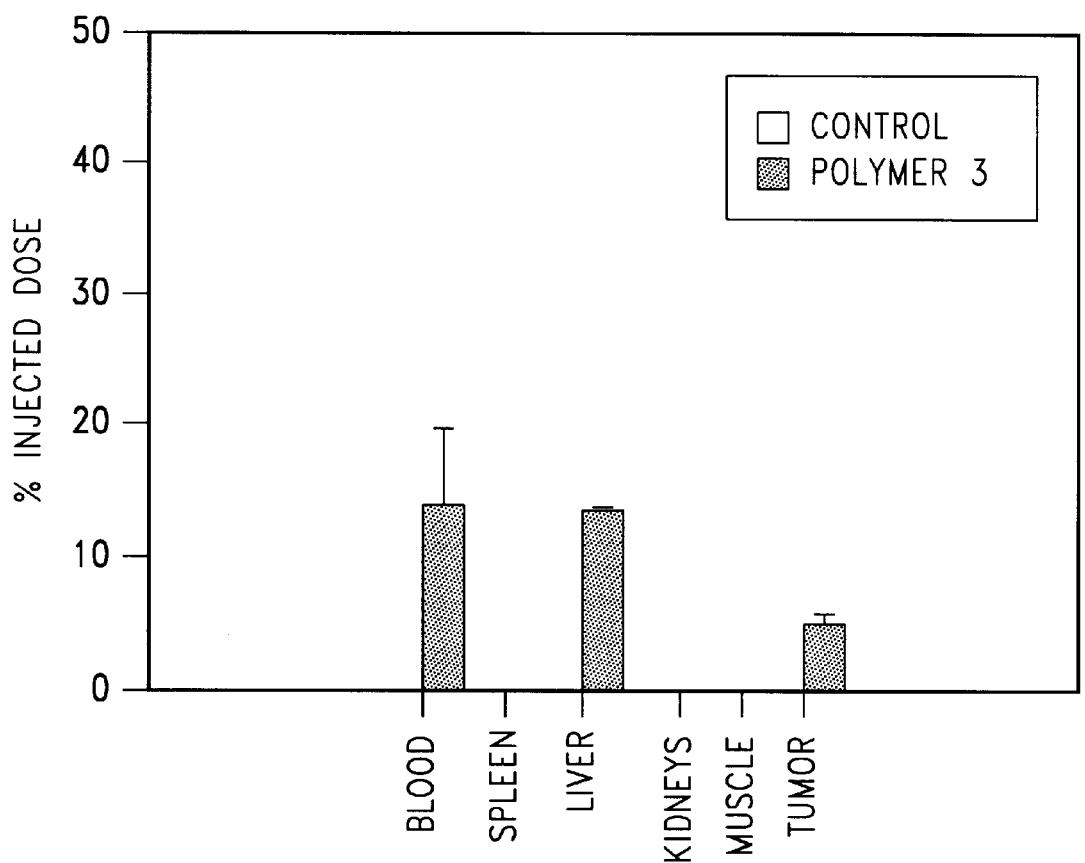
FIG. 2B is a graph of comparative biodistribution data of contrast agent Polymer 3 (NC100448) versus indocyanine green as control in female immunodeficient mice containing HT-29 tumors at three hours post intravenous injection of phosphate buffered saline solutions of each. Polymer 3 is detected in the tumor; the control compound is negligibly detected. Relative to FIG. 2A, the concentration of the contrast agent in the tumor has increased while the concentration in the blood has decreased.

All publications and patent applications referred to herein are incorporated by reference.

The invention will now be described further with reference to the following non-limiting Examples.

The term "air-exposed" as used herein with respect to a compound means that air which comprises oxygen in amounts from about 1% to about 99% and preferably from about 15% to about 25% as the gas content of air, and which oxygen is a known oxidizing reagent, and which oxygen is known to be capable of forming hydroperoxides with poly (alkylene oxides), is permitted to come into chemical contact with said compound so as to permit at least one oxidation reaction to occur. For example, if oxygen is allowed to react with a poly(ethylene oxide)-containing compound comprising recurring units of $-(O-CH_2-CH_2)_n-$ where n is an integer which represents the number of such recurring units in the polymer or oligomer or n is a number which represents the average molecular weight of the poly(ethylene oxide) unit, then an air-exposed poly (ethylene oxide)-containing compound would contain at least one unit of $-(O-CH(OOH)-CH_2)-$ with the remainder of the polymer comprising n-1 or fewer units of $-(O-CH_2-CH_2)-$. In this regard, a singly oxidized air-exposed poly(ethylene oxide) unit may be written as $-(O-CH_2-CH_2)_a-(O-CH(OOH)-CH_2)_b-(O-CH_2-CH_2)_c-$ where a+b+c=n and b=1. If more than one oxidation to a hydroperoxide is present, then b>1, and the b units of $-(O-CH(OOH)-CH_2)-$ can be distributed randomly among the n—b units of $-(O-CH_2-CH_2)-$. In a similar fashion, polymers comprising poly(propylene oxide) can be represented as containing recurring units of $-(O-CH(CH_3)-CH_2)-$, and polymers comprising air-exposed poly(propylene oxide) contain at least one unit of a hydroperoxide which may be represented as $-(O-C(CH_3)(OOH)-CH_2)-$ or $-(O-CH(CH_3)-CH(OOH))-$. More than one unit of hydroperoxide can be introduced into a poly(alkylene oxide)-containing polymer. In the above discussion, b can be as small as 1 and range as large as n/5, preferably from 1 to about n/10 where n>10.

EXAMPLE 1

Preparation of a copolymer of $PEG_{3400}$-α,ω-diamine and aluminum(III)phthalocyanine tetrasulfonyl chloride with Aerobic Workup PEG 3400-α,ω-diamine (Shearwater Polymers, Huntsville, Ala. ; 0.391 g, 0.115 mMoles) was dissolved in pyridine (75 mL) with magnetic stirring. Approximately 50 mL of pyridine were distilled off under nitrogen from an oil bath at 120–130° to dehydrate the reaction mixture, the solution was cooled to ambient temperature, and aluminum (III)phthalocyanine tetrasulfonyl chloride (0.111 g, 0.115 mMoles, prepared from the corresponding acid, Porphyrin Products, Logan, Utah) was added. The reaction mixture was stirred for 18 hours at 20° C., and then heated at reflux for 30 minutes. The solvent was then removed on a rotary evaporator at 40° C., the product residue was distributed into air saturated water, and the mixture was filtered in air under vacuum. The filtered solution was then passed, in the presence of air and ambient fluorescent light, successively through a column containing strong acid ion exchange resin and then through a column containing strong base (Na form) ion exchange resin to convert the acidic groups in the product to their sodium salts. Soluble lower molecular weight components were removed by diafiltration through a 10,000 MW membrane (Amicon, Beverly, Mass.) against air-saturated water. The dark blue residual liquid was evaporated on a rotary evaporator at temperatures below 40° to yield a dark blue solid (0.09 g). The solid product was exposed to air. Size exclusion HPLC analysis indicated that the product had an average molecular weight of 150000, and it had $\lambda_{max}$ 676 nm (water). When a solution of this material was redissolved into sterile phosphate buffered saline and injected into female immunodeficient mice with HT-29 tumors, 4% of the injected dose was localized in the tumor after one hour.

EXAMPLE 2

Preparation of a copolymer of $PEG_{3400}$-α,ω-diamine and aluminum(III)phthalocyanine tetrasulfonyl chloride A solution of PEG-3,400-bisamine (available from Shearwater Polymers, Inc.) in pyridine is treated with solid aluminum(III)phthalocyanine tetrasulfonyl chloride which is prepared by the action of thionyl chloride on aluminum (III)phthalocyanine tetrasulfonate chloride (available from Porphyrin Products) and the reaction is stirred at ambient temperature under nitrogen until the solid is dissolved and then for an additional twenty four hours. The resulting product mixture is poured into a ten fold volume of endotoxin-free ice-water, the resulting mixture is filtered, and the polymeric reaction component is purified by ultrafiltration using a 10,000 molecular weight cut-off membrane to reduce the volume by ten-fold followed by diafiltration using sterile phosphate buffered saline as the diafiltration medium. After ten volumes are collected, the polymeric product is treated with oxygen by bubbling the solution with sterile air for one hour. The reaction product solution is then filtered through a sterile 0.2 micron syringe filter. A bolus of this solution is injected into a female immunodeficient mouse containing a flank HT-29 tumor. The concentration of dye in the blood is monitored by absorption spectroscopy. After the concentration of dye in the blood is reduced to less than 1% of injected dose, the tumor area is subjected to ultrasound energy, continuous and optionally pulsed, at spatial peak temporal average intensity (SPTA) of 100 mW/cm squared for sufficient time to induce a reduction in growth rate of the tumor.

EXAMPLE 3

Preparation of a copolymer of ethylene-1,2-diamine and aluminum(III)phthalocyanine tetrasulfonyl chloride with Aerobic Workup This material was prepared by the same method used in Example 2 above, but using ethylenediamine (Aldrich, 0.0058 g, 0.10 mMoles) in place of the PEG 3400-α,ω-diamine. The aqueous solution of the product was diafiltered through a 500 MW membrane, and the dark blue residual solution ion exchanged to the sodium salt, and evaporated to yield a dark blue solid (0.10 g).

EXAMPLE 4

Preparation of a copolymer of PEG 5000-α,ω-diamine and aluminum(III)phthalocyanine tetrasulfonyl chloride with Aerobic Workup The method used was similar to that described in Example 2 above for the copolymerization involving PEG 3400-α, ω-diamine. However, in this case the following reagents and amounts were used: PEG 5000-α,ω-diamine (Shearwater Polymers, Huntsville, Ala.; 2.50 g, 0.50 mMoles); pyridine (50 mL, about 30 mL of which were removed by distillation; and aluminum(III) phthalocyanine tetrasulfonyl chloride (0.10 g , 0.10 mMoles). The reaction mixture was heated at reflux under nitrogen for 30 minutes, and then the solvent was removed. Diafiltration was performed against air saturated water using a 10,000 MW membrane. The retentate was concentrated by ultrafiltration and residual water was removed by rotary evaporation to provide a dark blue solid in air (0.08 g). It had $\lambda_{max}$ 676 nm (water). When a solution of this compound in phosphate buffered saline was injected into female immunodeficient mice with HT-29 tumors, 2.5% of the injected dose was localized in the tumor after one hour.

EXAMPLE 5

Preparation of a copolymer of melamine and aluminum (III)phthalocyanine tetrasulfonyl chloride with Aerobic Workup Aluminum(III)phthalocyanine tetrasulfonyl chloride (0.10 g, 0.10 Moles) was added to dimethylformamide (1 ML) containing N,N-diisopropyl-N-ethylamine (0.1 mL, 0.57 mMoles) and stirred under nitrogen for 1 hour. Melamine (Aldrich, 0.0022 g, 0.017 mMoles) was then added. Melamine was very sparingly soluble in the reaction mixture. The mixture was stirred at ambient temperatures for 4 days, by the end of which time the melamine had dissolved. The reaction mixture was poured over ice in air, and the resultant blue solution was diafiltered through a 3000 MW membrane against water which had been in equilibrium with air. The dark blue retentate solution was evaporated with exposure to air to yield a dark blue solid, $\lambda_{max}$ 680 nm (water). When a solution of this compound in phosphate buffered saline was injected into female immunodeficient mice with HT-29 tumors, 0.1% of the injected dose was localized in the tumor after one hour.

EXAMPLE 6

Synthesis with Aerobic Workup of Triblock poly(ethylene oxide-co-propylene oxide-co-ethylene oxide)-α,ω-diamine with a Block Ratio of 40:20:40 and a Weight Average Molecular Weight of Approximately 14600

Fifty grams of triblock α,ω-dihydroxypoly(ethylene oxide-co-propylene oxide-co-ethylene oxide) with a block ratio of 40:20:40 and a weight average molecular weight of approximately 14,600 (also known as Pluronic Surfactant F-108, BASF Corp.) was treated with 275 mL of toluene and then heated at reflux for two hours over a Dean Stark trap. The system was then cooled, and the trap and its contents (about 25 mL) were removed. The polymer in toluene was then treated with 1.25 mL of thionyl chloride and 0.053 mL of anhydrous dimethylformamide. The reaction mixture was stirred at 105° C. for 2 hours, cooled to room temperature, and then stirred at room temperature overnight. Volatiles were then removed on a rotary evaporator to give 49.35 g of an off-white solid which was readily powdered. In addition to the dominant polyalkylene oxide peaks between 70 and 80 ppm which are also seen in the starting Surfactant F-108, the $^{13}$C NMR spectrum of the product contains a singlet at 42.69 ppm. This is consistent with the presence of terminal carbons bonded to chlorine. In addition, no peak was observed near 61 ppm where the terminal hydroxyl-bearing carbons of Surfactant F-108 resonate.

A total of 49.08 g of this polymer chloride reaction mixture, 0.89 g of sodium azide, and 2.83 g of potassium iodide were treated with 350 mL of anhydrous dimethylformamide and stirred at 100° C. for 5 hours under dry argon. The reaction mixture was then stirred at room temperature overnight under argon. Volatiles were then removed on a rotary evaporator at 50° C. to provide a melt residue which solidified to a tan solid. The solid was dissolved in 500 mL of distilled water and shaken with 500 mL of chloroform. After separation of the layers (very slow), the aqueous layer was extracted with two 500 mL portions of chloroform. The three chloroform extracts were combined and dried over magnesium sulfate. Volatiles were removed to yield 45.58 g of a white solid. The $^{13}$C NMR spectrum of this product contains a singlet at 50.6 ppm which is consistent with the presence of terminal carbons bearing azides. No peak near 42 ppm attributable to the starting chloride was observed.

A total of 44.05 g the above reaction product was treated with 3.15 g of triphenyl phosphine and 2300 mL of anhydrous pyridine. The reaction mixture was stirred under argon at room temperature, and the reaction product was used without isolation in the next step of the synthesis.

The reaction mixture from the previous step was treated with 200 mL of 30% ammonium hydroxide (aqueous) and stirred at room temperature for 7 hours. The reaction produced a vigorous foaming, and a very large vessel was required to avoid foam-over. Volatiles were then stripped on a rotary evaporator overnight, the residual solid was redissolved in 500 mL of chloroform, the solution was dried over magnesium sulfate, and the volatiles were evaporated to leave a white solid comprising 39.31 g. When a phosphorus NMR spectrum of the product indicated that a significant phosphorus signal still remained, a 2.0 g sample of the product was treated with 38 ML of 30% ammonium hydroxide (aqueous) and stirred at 60° for 4 hrs. The reaction mixture was then cooled to room temperature, washed with four 40 mL portions of ether, and then the volatiles were removed on a rotary evaporator. The product was an off white waxy solid comprising 1.46 g. This time no phosphorus signal was found in the phosphorus NMR. Also the $^{13}$C NMR spectrum of the product contained a peak at 41.78 ppm, consistent with terminal carbons bearing amines. No peak near 50 ppm corresponding to the starting bis-azide remained. This material was allowed to come in contact with air.

EXAMPLE 7

Synthesis with Aerobic Workup of Triblock poly(ethylene oxide-co-propylene oxide-co-ethylene oxide)-α,ω-bis-(rhodamine B sulfonamide) with a Block Ratio of 40:20:40 and a Weight Average Molecular Weight of approximately 14600

A total of 1.25 g. of triblock poly(ethylene oxide-co-propylene oxide-co-ethylene oxide)-α,ω-diamine prepared in example 5 above was treated with 0.026 g of 4-N,N-dimethylaminopyridine and 10 mL of anhydrous pyridine. The resulting solution was treated with 0.12 g of rhodamine B sulfonyl chloride (Molecular Probes) and stirred at room temperature under nitrogen overnight. The resulting intensely purple solution was stripped on a rotary evaporator to provide an intensely purple solid comprising 1.42 g which was exposed to air. A total of 1.0 g of the crude product was dissolved in 40 mL of air-saturated distilled water. The resulting solution was filtered through a 0.45 micron nylon filter in air, and the filtrate was diafiltered against air-saturated distilled water in a 50 mL magnetically stirred diafiltration cell (Amicon) containing a 3000 MW nominal molecular weight cut-off cellulose acetate diafiltration membrane (Amicon YM-3). The diafiltration was continued for 35 volume turnovers, i.e., 1,750 mL of diafiltrate were collected. Initially the diafiltrate was intensely purple, but as the diafiltration continued the purple color intensity diminished until the diafiltrate was colorless to the eye at 35 turnovers. The volatiles in the intensely purple retentate were removed by rotary evaporation to leave an intensely purple solid which was exposed to air and comprised 0.92 g. The $^{13}$C NMR spectrum of the product contained the dominant polyalkylene oxide peaks between 70 and 80 ppm that are also seen in the spectrum of the F-108 Surfactant originally used as the starting material in the synthetic sequence and which are seen in the spectra of all the intermediates. In addition, in the spectrum of the reaction product a new singlet was observed at 45.69 ppm. Absent was the peak near 41 ppm that was observed in the spectrum of the precursor diamine polymer intermediate. Size exclusion HPLC studies indicated a single broad peak with a peak molecular weight of approximately 15000 relative to PEG reference standards. The compound showed a broad spectral absorbance peaking at 584 nm.

EXAMPLE 8

Lymph Node Markers

A solution of air-exposed triblock poly(ethylene oxide-co-propylene oxide-co-ethylene oxide)-α,ω-bis-(rhodamine B sulfonamide) prepared in Example 7 can be injected subcutaneously in the dorsal side of the hand or between the web spaces of the fingers and will migrate into the lymphatics. Once into the lymphatics, triblock poly(ethylene oxide-co-propylene oxide-co-ethylene oxide)-α,ω-bis-(rhodamine B sulfonamide) will delineate both the vessels and the lymph nodes such that resection of the lymph nodes would be facilitated. Alternatively, the solution of triblock poly (ethylene oxide-co-propylene oxide-co-ethylene oxide)-α, ω-bis-(rhodamine B sulfonamide) can be injected peri-tumorially in the breast or other location (i.e., peri-tumorially around skin lesions of melanoma, prostate cancer, colon cancer, etc.) to mark the regional draining lymph nodes (often referred to as the sentinel nodes). Also, these air-exposed polymeric materials can be instilled into the lung near or in the same lobe as a lesion to migrate to the regional draining lymph nodes. SDT can be used to destroy the cancerous tissue by administration of an effective amount of ultrasound acoustic energy.

EXAMPLE 9

Preparation of Air-exposed-Tetronic-908-conjugated-to-fluorescein Isothiocyanate A sample of Tetronic 908 (BASF, a 27,000 average molecular weight block copolymer comprising a central ethylenediamine unit and four units of poly(propylene oxide-co-block-ethylene oxide) subtended from the nitrogen atoms of the ethylene diamine and reported by BASF to have an acute oral toxicity at 100% concentration of >15 g/Kg on albino rabbits) was diafiltered in air against air-saturated distilled water, and the product was isolated by lyophillization from the retentate. This material was reacted with fluorescein isothiocyanate (Molecular Probes Inc., Eugene, Oreg.). The air exposed dye-polymer product was characterized by absorption spectroscopy as having an average of 0.9 molecules of dye per molecule of air-exposed polymer. This suggested an average level of incorporation of one dye molecule per polymer unit rather than the possible four molecules of dye.

EXAMPLE 10

Fate of air-exposed-Tetronic-908-conjugated-to-fluorescein isothiocyanate in Dog Blood A solution of air-exposed-Tetronic-908-conjugated-to-fluorescein isothiocyanate prepared in Example 9 above was injected into beagle dogs, and blood samples were taken at regular intervals. Both in vivo imaging with a confocal scanning microscope and in vitro assay with flow cytometry suggested that the fluorescent T-908 binds to a specific cell class within the blood. While that cell population has not been identified, it is believed that the population in question can be destroyed by sonodynamic therapy if the T-908-fluorescein-isothiocyanate can be made to covalently attach to or adsorb onto the cell and thereby destroy the cells under the influence of ultrasound. Thus, ultrasound irradiation of a major artery for a relatively short period of time could substantially deplete the cell class in question in the body, thereby providing a therapeutic effect.

The results indicated that the air-exposed-Tetronic-908-conjugated-to-fluorescein isothiocyanate attached to leucocytes (white blood cells) without impacting their function. This was observed by flow cytometry as well as by microscopy with a fluorescence detector.

EXAMPLE 11

Preparation of an Air-exposed Stable Emulsion of Sudan III

Sudan III (Aldrich Chemical Co.) also known as D&C Red No 17, Solvent Red 23, and Cerasin Red, is very insoluble in water but is soluble in sesame oil, a well known oil for parenteral oil-in-water emulsions (i.e., Intralipid, Lyposin, etc.). Thus, an emulsion of Sudan III was prepared as follows: A saturated solution of Sudan III in sesame oil was prepared by gently rotating the container over the weekend (approx 72 hr). The oil solution was then filtered through a 5 micron syringe filter followed by a 0.8 micron filter to remove undissolved solid Sudan III. The resulting saturated solution was then emulsified in air-exposed water at a ratio of 10% "oil" to 90% aqueous air-exposed surfactant solution (comprising air-exposed F68 or air-exposed P79) using ultrasonic energy followed by microfluidization at approximately 14,000 PSI until a constant droplet size was achieved. Droplet size was measured by light scattering using a Horiba 910 and a volume weighted average. The resulting emulsions were also sterilized by traditional steam sterilization and the droplet size measured again. The results are:

| Formulation | Average Droplet Size (nm) | |
|---|---|---|
| | Before Autoclaving | After Autoclaving |
| 1. 1.2% lecithin, 0.3% F68 | 787 | 909 |
| 2. 1.2% Lecithin, 2% P79 | 141 | 199 |
| 3. 0.8% Lecithin, 3% P79 | 122 | 128 |

P79 (see Example 2k of PCT/GB95/02109—a PEG-double ester of molecular weight about 10 KD) appeared to add greatly to the ability to make a small emulsion droplet of sesame oil saturated with the Sudan III. The resulting rose colored emulsion was stable on the shelf. F68 refers to air-exposed Pluronic F68 (BASF).

EXAMPLE 12

Preparation of Air-exposed nanoparticles of Fluorescein

A composition comprising a nanoparticle suspension of Fluorescein (Aldrich Chemical Co.) was prepared by placing 7.5 ml of milling beads (0.7 mm zirconium silicate) and 0.9 gm of fluorescein into a 15 ml bottle. Using a stock solution of an air-exposed poly(alkylene oxide)-containing surfactant, the suspension was made up to 3.3 ml in aqueous phase. This was done for each of 3 surfactants: air-exposed Brij 58 [poly(ethylene oxide)20 cetyl ether], air-exposed Tyloxapol, and air exposed Pluronic F-108 (BASF). The particle sizing results were:

| Formulation | Day 3 | Day 5 | Day 6 |
|---|---|---|---|
| air-exposed F108 | 247 um | 4.4 μm | 194 nm |
| air-exposed Tyloxapol | 91 nm | — | — |
| air-exposed Brij 58 | 101 nm | — | — |

Compositions comprising nanoparticulate dispersions of other solids such as iodinated aromatic materials such as ethyl 3-(N-acetyl-N-ethylamino)-5-[(5-dimethylamino-1-naphthylsulfonyl)amino]-2,4,6-triiodobenzoate that are useful as X-ray contrast agents and useful as CT contrast agents can be prepared in a similar fashion using at least one air-exposed poly(alkylene oxide)-containing surfactant.

EXAMPLE 13

Localizations and Utility of Compositions ethyl 3-(N-acetyl-N-ethylamino)-5-[(5-dimethylamino-1-naphthylsulfonyl)amino]-2,4,6-triiodobenzoate and Air-exposed Surfactant in Marking Lymph Nodes by CT and by Visible Fluorescence A composition comprising a nanoparticle suspension of ethyl 3-(N-acetyl-N-ethylamino)-5-[(5-dimethylamino-1-naphthylsulfonyl)amino]-2,4,6-triiodobenzoate (see WO96/23524) prepared as in the preceding examples using air-exposed Pluronic F108 at 3% (wt/vol %) and 15% (wt/vol % ethyl 3-(N-acetyl-N-ethylamino)-5-[(5-dimethylamino-1-naphthylsulfonyl)amino]-2,4,6-triiodobenzoate) with 15% PEG 1450 added for tonicity and sterilization. The average particle size of this suspension composition was approximately 220 nm after autoclaving. Rabbits were dosed at 2×0.5 ml in the dorsal side of the front and rear paws with the following levels of lymph node opacification in CT imaging was measured at various times post injection:

| | Lymph Node Enhancement at Times post injection* | | |
|---|---|---|---|
| | Times | | |
| Location | 2.5 hr | 24 hr | 7 days |
| Axillary | 2.38 | 2.07 | 1.44 |
| Popliteal | 2.28 | 4.29 | 1.50 |

*These values have been converted to mg I/ml in the lymph node. 1.5 is considered background in these measurement.

Additionally, one animal was sacrificed at 24 hr post injection such that the popliteal lymph node could be resected for visual inspection. This node, when illuminated with UV light, gave a green fluorescence as would be expected for this air-exposed, dansyl-containing composition.

EXAMPLE 14

Preparation of 2-[2-[2-(4-isothiocyano)phenoxy-3-[[1,3-dihydro-1,1-dimethyl-3-(3-sulfoproyl)-2H-benz[e]indol-2-ylidene]ethylidene]-1-cyclohexen-1-yl]ethenyl]-1,1-dimethyl-3-(3-sulfopropyl)-1H-benz[e]indolium, Inner Salt, Sodium Salt, Reaction Product with $PEG_{3400}$-α,ω-diamine The following reaction scheme was used to produce the title compound:

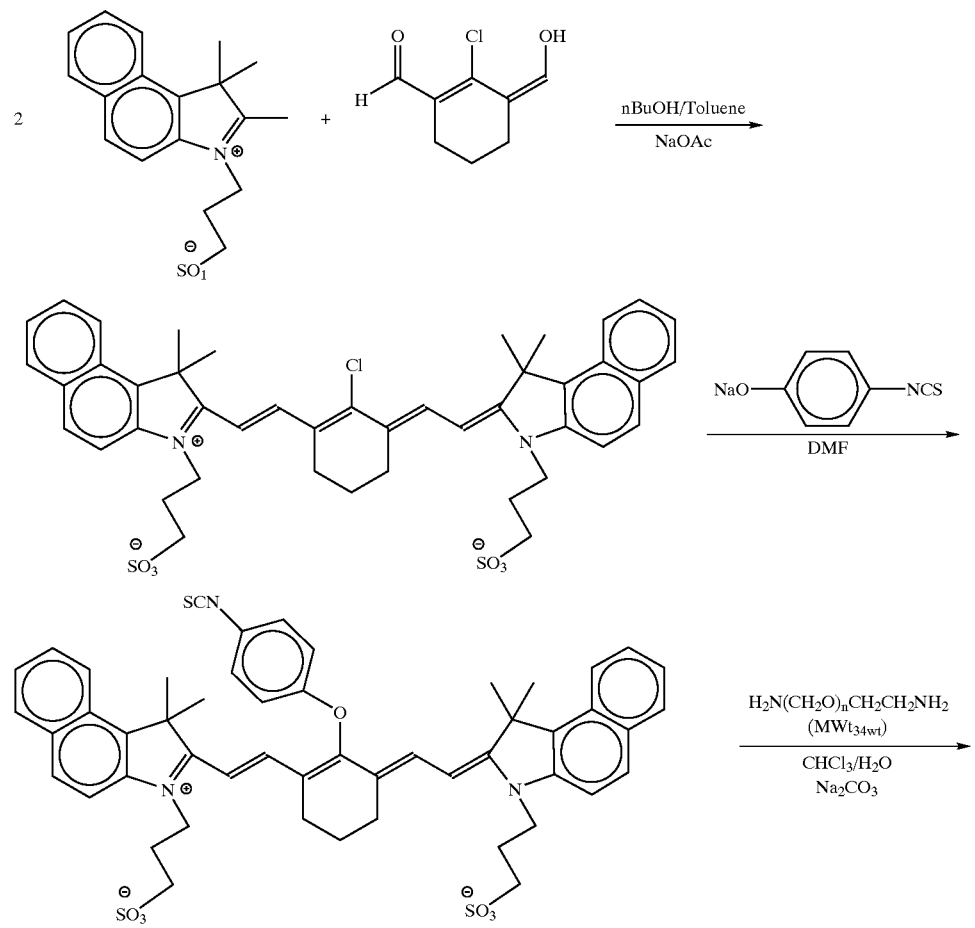

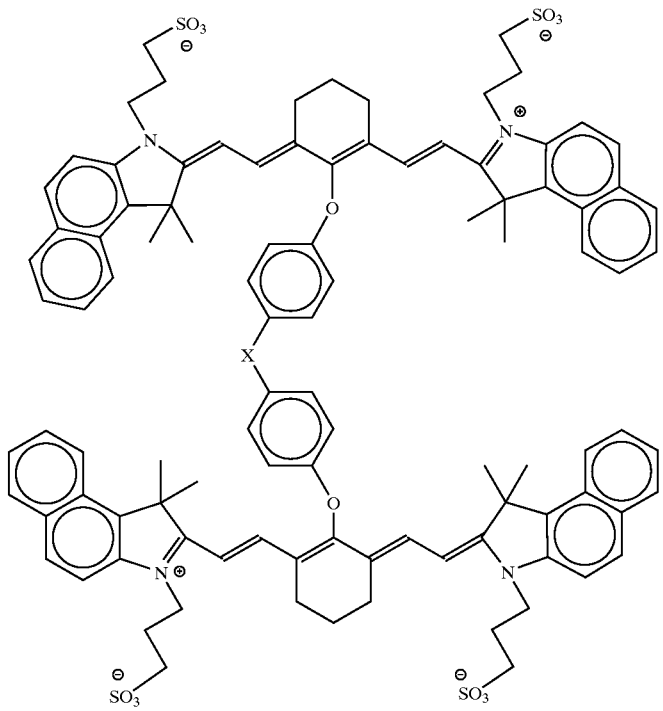

wherein X is NH—CS—NH(CH$_2$CH$_2$O)$_n$CH$_2$CH$_2$NH—CS—NH).

EXAMPLE 15

Preparation of 2-[2-[2-(4-isothiocyano)phenoxy-3-[[1,3-dihydro-1,1-dimethyl-3-(3-sulfoproyl)-2H-benz[e]indol-2-ylidene]ethylidene]-1-cyclohexen-1-yl]ethenyl]-1,1-dimethyl-3-(3-sulfopropyl)-1H-benz[e]indolium, Inner Salt, Sodium Salt, Reaction Product with PEG$_{10000}$-α,ω-diamine The title product was produced analogously to that of Example 14 using PEG 10000 α,ω-diamine.

EXAMPLE 16

Liposomal Preparation

6-Carboxyfluorescein and cyclophosphamide is added to a liposome suspension formed from 8.2% lecithin (phosphatidyl choline) and 0.8% dimyristylphosphatidyl ethanolamine PEG (5K), which is designed to impart prolonged blood pool residence to the liposome. The phospholipids and the surfactant are mixed in water using ultrasonic energy from a probe sonicator (Bransonic Sonifier 450, 90% duty cycle, output 10). Liposomes are prepared using a Microfluidics M110S microfluidizer at 14,000 PSI with 4 passes through the interaction chamber of the phospholipid mixture. The resulting liposomes are approximately 100 nm in average diameter, as determined by light scattering, and remain the same size after autoclave sterilization. In addition, these liposomes are able to pass through a sterile filter (i.e. 0.2 micron pore size). Addition of the dye and the toxic agent in sufficient amount to make the suspension approximately 7 mg/ml in both does not alter the physical characteristics of the liposomal suspensions.

EXAMPLE 17

Blood Pool Agent: A copolymer of PEG$_{3,400}$-α,ω-diamine,4,4'-azobis(4-cyanovaleric acid)acid, and Gadolinium Metallated diethylenetriaminepentaacetic acid (a) To a solution of 10 parts of PEG$_{3,400}$-α,ω-diamine (Shearwater Polymers, Inc.) as a 5% solution in dimethyl sulfoxide (DMSO) is added 1 part of 4,4'-azobis(4-cyanovaleric acid) acid (Aldrich Chemical Co.) and 2 parts of dicyclohexylcarbodiimide. The reaction mixture is stirred for 24 hours in the dark at less than 20° C. The reaction mixture is then treated first with 20 parts of triethylamine and then with 9 parts of diethylenetriaminepentaacetic acid dianhydride (Aldrich Chemical Co.) in DMSO at a concentration of 1 g per 25mL. The reaction mixture is then stirred at room temperature for another 24 hours in the dark. To the product mixture is slowly added a 10 volume excess of sterile water and the reaction mixture is allowed to stand for 6 hours. The aqueous portion is decanted and filtered through a 0.45 micron nylon filter. The filtrate is then diafiltered in air against sterile water in a diafiltration cell equipped with a 3,000 molecular weight cut-off membrane. The aqueous retentate can be isolated by lyophilization.

(b) An aqueous solution of the polymer retentate solution prepared in Example 17(a) is treated with excess gadolinium acetate prior to diafiltration. The reaction mixture is diafiltered in air against sterile water in a diafiltration cell equipped with a 3,000 molecular weight cut-off membrane. The aqueous retentate containing gadolinium chelated to the polymer is isolated by lyophilization.

EXAMPLE 18

Blood Pool Agent: A copolymer of PEG$_{3,400}$-α,ω-diamine,4,4'-azobis(4-cyanovaleric acid)acid, and gadolinium Metallated diethylenetriaminepentaacetic acid Containing Covalently Attached 4-amino-2,2,6,6-tetramethylpiperidine (a) The lyophilized polymer prepared in Example 17 is dissolved in dichloromethane and treated with 1 part of 4-amino-2,2,6,6-tetramethylpiperadine (Aldrich) and 1 part of dicyclohexylcarbodiimide. After 24 hours in the dark, the volatiles are evaporated in a stream of cool nitrogen, the residue is taken up in water, filtered through a 0.45 micron nylon filter, and then diafiltered in air against sterile water in a diafiltration cell equipped with a 3,000 molecular weight cut-off membrane. The aqueous retentate is isolated by lyophilization.

(b) An aqueous solution of the polymer retentate solution prepared in Example 18(a) is treated with excess gadolinium acetate prior to diafiltration. The reaction mixture is diafiltered in air against sterile water in a diafiltration cell equipped with a 3,000 molecular weight cut-off membrane. The aqueous retentate containing gadolinium chelated to the polymer is isolated by lyophilization.

EXAMPLE 19

Blood Pool Agent: A copolymer of $PEG_{3,400}$-α,ω-diamine,4,4'-azobis(4-cyanovaleric acid) acid, and dysprosium Metallated diethylenetriaminepentaacetic acid An aqueous solution of the polymer retentate solution prepared in Example 17(a) is treated with excess dysprosium acetate prior to diafiltration. The reaction mixture is diafiltered in air against sterile water in a diafiltration cell equipped with a 3,000 molecular weight cut-off membrane. The aqueous retentate containing dysprosium chelated to the polymer is isolated by lyophilization.

EXAMPLE 20

Blood Pool Agent: A copolymer of $PEG_{3,400}$-α,ω-diamine,4,4'-azobis(4-cyanovaleric acid) acid, and dysprosium metallated diethylenetriaminepentaacetic acid containing covalently attached 4-amino-2,2,6,6-tetramethylpiperidine An aqueous solution of the polymer retentate solution of Example 18(a) is treated with excess dysprosium acetate prior to diafiltration. The reaction mixture is diafiltered in air against sterile water in a diafiltration cell equipped with a 3,000 molecular weight cut-off membrane. The aqueous retentate containing dysprosium chelated to the polymer is isolated by lyophilization.

EXAMPLE 21

Di-t-butyl N-[4,5-dihydro-2-(6-hydroxy-2-benzothiazolyl)-4-thiazolecarboxamido]-N,N-diacetate Part (a)

To a solution 1 part of 4,5-dihydro-2-(6-hydroxy-2-benzothiazolyl)-4-thiazolecarboxylic acid (Sigma Chemical Co.) and 1 part of di-t-butyl iminoacetate under argon at room temperature in the dark in DMF is added 1 part of dicyclohexylcarbodiimide. After 48 hours, the volatile solvent is removed under a sweeping flow of argon and the product is purified by chromatography on silica using ethyl acetate and methanol.

Part (b)

N-[4,5-dihydro-2-(6-hydroxy-2-benzothiazolyl)-4-thiazolecarboxamido]-N,N-diacetic acid A solution of di-t-butyl N-[4,5-dihydro-2-(6-hydroxy-2-benzothiazolyl)-4-thiazolecarboxamido]-N,N-diacetate (Example 25) in chloroform under argon is treated with a 1% solution of trifluoroacetic acid in the dark at room temperature. Volatiles are removed with a sweeping flow of argon to leave a crude sample of N-[4,5-dihydro-2-(6-hydroxy-2-benzothiazolyl)-4-thiazolecarboxamido]-N,N-diacetic acid which is crystallized from ethyl acetate and methanol.

Part (c)

A copolymer of $PEG_{3,400}$-α,ω-diamine, 4,4'-azobis (4-cyanovaleric acid) acid, and N-[4,5-dihydro-2-(6-hydroxy-2-benzothiazolyl)-4-thiazolecarboxamido]-N,N-diacetic acid To a solution of 4 parts of $PEG_{3,400}$-α,ω-diamine (Shearwater Polymers, Inc.) as a 5% solution in dimethyl formamide (DMF) is added 1 part of 4,4'-azobis(4-cyanovaleric acid) acid (Aldrich Chemical Co.) one part of N-[4,5-dihydro-2-(6-hydroxy-2-benzothiazolyl)-4-thiazolecarboxamido]-N,N-diacetic acid (Example 26) and 4 parts of dicyclohexylcarbodiimide. The reaction mixture is stirred for 48 hours in the dark at less than 20° C. To the product mixture is slowly added a 10 volume excess of sterile water and the reaction mixture is allowed to stand for 1 hour. The aqueous portion is decanted and filtered through a 0.45 micron nylon filter. The filtrate is then diafiltered in air against sterile water in a diafiltration cell equipped with a 3,000 molecular weight cut-off membrane. The aqueous retentate is isolated by lyophilization.

EXAMPLE 22

A copolymer of $PEG_{3,400}$-α,ω-diamine,4,4'-azobis (4-cyanovaleric acid), N-[4,5-dihydro-2-(6-hydroxy-2-benzothiazolyl)-4-thiazolecarboxamido]-N,N-diacetic acid, and diethylenetriaminepentaacetic acid To a solution of 10 parts of $PEG_{3,400}$-α,ω-diamine (Shearwater Polymers, Inc.) as a 5% solution in dimethyl formamide (DMF) is added 1 part of 4,4'-azobis(4-cyanovaleric acid) acid (Aldrich Chemical Co.), one part of N-[4,5-dihydro-2-(6-hydroxy-2-benzothiazolyl)-4-thiazolecarboxamido]-N,N-diacetic acid (Example 21, Part (b)) and 4 parts of dicyclohexylcarbodiimide. The reaction mixture is stirred for 48 hours in the dark at less than 20° C. The reaction mixture is then treated first with 20 parts of triethylamine and then with 8 parts of diethylenetriaminepentaacetic acid dianhydride (Aldrich Chemical Co.) in DMF at a concentration of 1 g per 25 mL. The reaction mixture is then stirred at room temperature for another 24 hours in the dark. To the product mixture is slowly added a 10 volume excess of sterile water and the reaction mixture is allowed to stand for 6 hours. The aqueous portion is decanted and filtered through a 0.45 micron nylon filter. The filtrate is then diafiltered in air against sterile water in a diafiltration cell equipped with a 3,000 molecular weight cut-off membrane. The aqueous retentate is isolated by lyophilization.

EXAMPLE 23

Blood Pool Agent: A copolymer of $PEG_{3,400}$-α,ω-diamine,4,4'-azobis(4-cyanovaleric acid)acid, N-[4,5-dihydro-2-(6-hydroxy-2-benzothiazolyl)-4-thiazolecarboxamido]-N,N-diacetic acid, and diethylenetriaminepentaacetic acid Containing gadolinium ion An aqueous solution of the polymer retentate solution prepared in Example 22 is treated with excess gadolinium acetate prior to diafiltration. The reaction mixture is diafiltered in air against sterile water in a diafiltration cell equipped with a 3,000 molecular weight cut-off membrane. The aqueous retentate containing gadolinium chelated to the polymer is isolated by lyophilization.

EXAMPLE 24

Blood Pool Agent: A copolymer of $PEG_{3,400}$-α,ω-diamine,4,4'-azobis(4-cyanovaleric acid) acid, N-[4,5-dihydro-2-(6-hydroxy-2-benzothiazolyl)-4-thiazolecarboxamido]-N,N-diacetic acid, and diethylenetriaminepentaacetic acid Containing dysprosium Ion An aqueous solution of the polymer retentate solution prepared in Example 22 is treated with excess dysprosium acetate prior to diafiltration. The reaction mixture is diafiltered in air against sterile water in a diafiltration cell equipped with a 3,000 molecular weight cut-off membrane. The aqueous retentate containing dysprosium chelated to the polymer is isolated by lyophilization.

EXAMPLE 25

Blood Pool Agent: A copolymer of $PEG_{3,400}$-α,ω-diamine,4,4'-azobis(4-cyanovaleric acid)acid, and diethylenetriaminepentaacetic acid Containing yttrium-90 ion An aqueous solution of the polymer retentate prepared in Example 17(a) is further diafiltered against 50 mM sodium acetate buffer containing 150 mM sodium chloride at pH 5.6 for 12 volume passes. A volume of radioactive yttrium chloride ($^{90}Y^{+3}Cl_3$ in 0.04 M hydrochloric acid at a specific activity of >500 Ci/g: Amersham-Mediphysics) is neutralized using two volumes of 0.5 M sodium acetate at pH 6.0. The neutralized $^{90}Y^{+3}$ acetate (1.0 mCi) is added to a 1 mL volume of the above polymer retentate in sodium acetate/sodium chloride pH 5.6 solution. The labeling of the polymer is allowed to proceed for one hour, and then the reaction mixture is loaded onto a PD-10 chromatography column which is prewashed and equilibrated in a buffer containing 50 mM sodium phosphate with 150 mM sodium chloride pH 7.4 (PBS). The sample is eluted from the column with PBS. Fractions of radiolabeled polymer are collected, assayed for radioactivity and pooled. The labeling efficiency is determined by removing 1.0 microliters of the sample and spotting it on to a Gelman ITLC strip. The strip is developed in a glass beaker containing 0.1 M sodium citrate, pH 6.0, for a few minutes until the solvent front has reached three-quarters of the way to the top of the paper. The strip is inserted into a System 200 Imaging Scanner (Bioscan) which has been optimized for $^{90}Y$. In this system, free $^{90}Y$ migrates at the solvent front while the chelated $^{90}Y$ does not.

EXAMPLE 26

Blood Pool Agent: A copolymer of $PEG_{3,400}$-α,ω-diamine,4,4'-azobis(4-cyanovaleric acid)acid, N-[4,5-dihydro-2-(6-hydroxy-2-benzothiazolyl)-4-thiazolecarboxamido]-N,N-diacetic acid, and diethylenetriaminepentaacetic acid Containing yttrium-90 Ion An aqueous solution of the polymer retentate solution prepared in Example 22 is treated as in Example 25 to provide a polymer containing yttrium-90 ion.

EXAMPLE 27

Blood Pool Agent: A copolymer of $PEG_{3,400}$-α,ω-diamine,4,4'-azobis(4-cyanovaleric acid)acid, and diethylenetriaminepentaacetic acid Containing samarium-153 Ion This material is prepared in the same fashion as described in Example 25 above but using $^{153}Sm^{+3}Cl_3$ in 0.04 M hydrochloric acid at a specific activity of >500 Ci/g (Amersham-Mediphysics).

EXAMPLE 28

A copolymer of $PEG_{3,400}$-α,ω-diamine,4,4'-azobis(4-cyanovaleric acid)acid, and diethylenetriaminepentaacetic acid Prepared in the Absence of Oxygen In an argon filled glove bag, 10 parts of freshly prepared $PEG_{3,400}$-α,ω-diamine (Shearwater Polymers, Inc., prepared under oxygen-free conditions) are dissolved in dimethyl sulfoxide (DMSO) which has been deoxygenated by sparging with argon for 1 hour to form a 5% solution. To this solution is added 1 part of 4,4'-azobis(4-cyanovaleric acid) acid (Aldrich Chemical Co.) and 2 parts of dicyclohexylcarbodiimide under argon. The reaction mixture is stirred for 24 hours in the dark at less than 20° C. The reaction mixture is then treated first with 20 parts of triethylamine and then with 9 parts of diethylenetriaminepentaacetic acid dianhydride (Aldrich Chemical Co.) in argon-sparged DMSO at a concentration of 1 g per 25 mL. The reaction mixture is then stirred at room temperature for another 24 hours in the dark. To the product mixture is slowly added a 10 volume excess of sterile water and the reaction mixture is allowed to stand for 6 hours. The aqueous portion is decanted and filtered through a 0.45 micron nylon filter in argon. The filtrate is then diafiltered against argon-sparged sterile water in a diafiltration cell (Amicon series 8000 stirred cell) equipped with a 5,000 molecular weight cut-off YM-5 membrane under argon pressure. The aqueous retentate is frozen under argon is a Virtus Corporation lyophilizer, and the polymer is isolated free of water by lyophilization. A slow bleed of argon gas is used to break the vacuum at the completion of the process, and the polymer is stored under argon in the dark.

The compositions in the Examples 17 to 27 can be prepared in the absence of oxygen in a similar anaerobic fashion if argon is used as the protecting atmosphere in all steps of the process and if exposure to air and oxygen is excluded in all steps.

EXAMPLE 29

A solution of 100.0 g (0.0690 mol) of polyethylene glycol of average molecular weight (MW) 1450 in toluene (1500 ml) was refluxed for 2 hours with azeotropic removal of water. The solution was cooled to 25° C., then treated with triethylamine (46.1 ml, 0.331 mol), 4-dimethylaminopyridine (1.69 g, 0.0138 mol) and p-toluenesulfonyl chloride (57.9 g, 0.303 mol), and then heated for 4 days at 60° C. under an atmosphere of nitrogen. After cooling to room temperature, the reaction mixture was filtered and the filtrate was extracted twice with water. The combined aqueous extracts were washed with ether, then extracted twice with $CHCl_3$. The combined $CHCl_3$ extracts were dried over anhydrous magnesium sulfate and then concentrated to yield 121.3 g of product.

A solution of 42.2 g (0.0240 mol) of the ditosylate in 420 ml of dioxane was cooled in an ice bath and a stream of methylamine was introduced over a period of 35 minutes. The reaction mixture was then heated in a sealed stainless steel reactor at 160° C. for 16 hours, cooled to room temperature, and then filtered. The filtrate was concentrated to remove solvent, then treated with water (844 ml) and 1.0 N NaOH (95.2 ml) and extracted twice with $CHCl_3$. The combined $CHCl_3$ extracts were dried over anhydrous magnesium sulfate and concentrated to leave 31.0 g of product.

A solution of 9.00 g (6.10 mmol) of the PEG-bis-(N-methylamine) in 45 mls of dimethylsulfoxide (DMSO) was treated with triethylamine (1.70 ml, 12.2 mmol) and a solution of 2.18 g (6.10 mmol) of diethylenetriaminepentaacetic acid internal dianhydride in DMSO (45 mls). The reaction mixture was stirred at room temperature for 16 hours, then treated with 360 ml of water. The resultant solution was filtered through a 0.45 μm nylon filter and the filtrate was diafiltered against air equilibrated water in a diafiltration cell equipped with a 3000 MW cut-off membrane to leave 170 ml of a solution of polymer product.

A 160 ml portion of the aqueous solution was treated with a two-fold molar excess of gadolinium(III) chloride hexahydrate, and then was diafiltered against water in air as described above. Lyophilization of the retentate yielded 8.66 g of product of average MW 16300 (as determined by SEC-HPLC using PEO molecular weight standards).

The relaxivity $(T_1)^{-1}$ of this material at 20 MHz and 40° C. was found to be 6.2 $mM^{-1}s^{-1}$.

Intravenous administration of 100, 200 and 400 mg/Kg to mice resulted in no deaths, no effect on body weight and no abnormalities upon necropsy after 14 days.

The same product, but prepared using radioactive $^{153}$Gd was employed in biodistribution studies in rats to determine a blood-pool half-life (elimination phase) of 75 minutes.

EXAMPLE 30

In a manner similar to Example 29, a polymeric gadolinium chelate of average MW 8,010 was prepared from PEG-α,ω,bis-N-methylamine of MW 1000. The blood-pool half-life (elimination phase) was determined to be 48 minutes.

EXAMPLE 31

In a manner similar to Example 29, a polymeric gadolinium chelate of average MW 16,800 was prepared from PEG-α,ω,bis-N-methylamine of average MW 2000.

EXAMPLE 32

In a manner similar to Example 29, a polymeric gadolinium chelate of average MW 22,400 was prepared from PEG-α,ω,bis-N-methylamine of average MW 3350.

The blood-pool half-life (elimination phase) of this material in rats was determined to be 141 minutes.

EXAMPLE 33

A solution of 15.30 g (11.70 mmol) of PEG ditosylate prepared from PEG of average MW 1000 in 153 ml of absolute ethanol was cooled in an ice bath, and a stream of ammonia was introduced over a period of 30 minutes. The reaction mixture was heated in a stainless steel reactor at 100° C. for 16 hr, cooled to room temperature, and then filtered. The filtrate was concentrated to remove solvent, treated with water (153 ml) and 1.0 N NaOH (46.8 ml), and extracted twice with CHCl$_3$. The CHCl$_3$ extracts were dried over anhydrous magnesium sulfate, filtered and then concentrated to leave 12.20 g of product PEG-α,ω-diamine.

A solution of 11.22 g (11.24 mmol) of this diamine in 56 ml of DMSO was treated with triethylamine (3.13 ml, 22.5 mmol) and a solution of 4.017 g (11.24 mmol) of diethylenetriaminepentaacetic acid dianhydride in DMSO (56 ml). The reaction mixture was stirred at room temperature for 16 hr, and then treated with 448 ml of water. The resulting solution was filtered through a 0.45 μm filter and the filtrate was diafiltered against water in a diafiltration cell equipped with a 3000 MW cut-off membrane to leave 225 ml of solution.

A 208 ml portion of the aqueous solution was treated with a two-fold excess of gadolinium(III)chloride hexahydrate, and then diafiltered against water. Lyophilization of the retentate yielded 11.58 g of product of average MW 12,500.

EXAMPLE 34

Example 33 was repeated except that the starting PEG had an average MW of 1450. The lyophilized product was determined to have an average MW of 21,900.

EXAMPLE 35

Example 29 was repeated except that 2,2'-bipyridyl-6,6'-bis-methyleneimino diacetic anhydride (B4A-dianhydride) was used in place of DTPA-dianhydride. The product was determined to have an average MW of 17,600.

EXAMPLE 36

Example 29 was repeated except that pyridine-2,6-bis-methyleneimino diacetic anhydride (P4A-dianhydride) was used in place of DTPA-dianhydride. The product was determined to have an average MW of 20,000.

EXAMPLE 37

Example 29 was repeated except that DyCl$_3$ was used in place of GdCl$_3$. The lyophilized product was found to have an average MW of 14,800. The relaxivity $(T_2)^{-1}$ of this material at 20 MHZ and 40° C. was found to be 0.109 $mM^{-1}s^{-1}$.

EXAMPLE 38

Example 37 was repeated except that the starting PEG had an average MW of 2000. The lyophilized product was found to have an average molecular weight of 15,300.

EXAMPLE 39

Example 37 was repeated except that the starting PEG had an average MW of 3350. The lyophilized product was found to have an average molecular weight of 20,100.

EXAMPLE 40

Example 33 was repeated except that DyCl$_3$ was used in place of GdCl$_3$. The lyophilized product was found to have an average MW of 45,500. The relaxivity $(T_2)^{-1}$ of this material at 20 MHZ and 40° C. was found to be 0.122 $mM^{-1}s^{-1}$.

EXAMPLE 41

Preparation of Tetra-(erythrosin-5-aminothiocarbonylamino)-T908 a) T908-tetraamine

One hundred grams of Tetronic T908 (BASF) in 525 ml of toluene was dried by azeotropic distillation for one hour with a 25 ml Dean-Stark trap. After cooling to room temperature, the solution was treated with 2.92 ml of thionyl chloride and 0.12 ml of DMF. The reaction mixture was heated at vigorous reflux with stirring under argon for 3 h, cooled to room temperature, and volatiles were removed under reduced pressure on a rotary evaporator to leave a light tan powder herein referred to as the "chloro-T9081" intermediate.

One hundred grams of the "chloro-T908" intermediate was dissolved in 700 ml of DMF and treated with 2.08 g of sodium azide plus 5.98 g of potassium iodide. This reaction mixture was heated to 100° C. for 6 h and then cooled to room temperature. Volatiles were removed under reduced pressure at 69° C. on a rotary evaporator.

The crude product was dissolved in 900 ml of distilled water and extracted with 1×1000 ml and 2×500 ml of chloroform. The chloroform layers were combined, dried over magnesium sulfate, and the solvent was evaporated to give 65.69 g of a light tan frangible solid herein referred to as the "azo-T908" intermediate.

A 62.5 g portion of the "azo-T908" intermediate was dissolved in 300 ml of anhydrous pyridine and treated with 6.56 g of triphenylphosphine. After stirring it at room temperature for 18 h, the resulting clear solution was treated with 300 ml of 30% ammonia (aqueous) and then stirred under argon at 50° C. for 5 hrs. The volatiles were removed under reduced pressure on a rotary evaporator, and the residue was treated with 562.5 ml of DMSO and 2250 ml of distilled water. The resulting solution was diafiltered for 12 turnovers using a Millipore spiral wound permeator with a nominal 10K cutoff. The final retentate was freeze dried to yield 43.22 g of an off-white powder herein referred to as the "T908-tetraamine" intermediate. A high field $^{13}$C nmr of the product showed a peak at 41.78 ppm, consistent with that expected for a methylene carbon adjacent to a terminal amine of the desired product. No aromatic peaks were observed in either the 13C or $^1$H nmr spectra.

b) Reaction of Erythrosin-5-isothiocyanate with the "T908-tetraamine" Intermediate One part of the "T908-tetraamine" intermediate dissolved in ten parts of distilled water plus three parts of 0.5M aqueous sodium carbonate is treated with excess erythrosin-5-isothiocyanate (Molecular Probes) with stirring at room temperature. The progress of the reaction is followed by SE-HPLC until complete. The reaction mixture is then diluted with sixty parts of distilled water, is ultrafiltered in a stirred diafiltration cell to a retentate volume of about one tenth the start volume, and then is diafiltered for 24 volume passes against water. The retentate is then lyophilized, is taken up in a minimum volume of methylene chloride, is precipitated into 100 parts of dry ether, is collected by filtration, and is washed with ether and dried to provide the desired product.

EXAMPLE 42

Preparation of Di-(erythrosin-5-aminothiocarbonylamino)-F108

Pluronic F108 (BASF) as the diol is converted to the corresponding diamine using the procedure described in part (a) of Example 41. The diamine is then reacted with erythrosin isothiocyanate as described in part (b) of Example 41 to provide the desired product.

EXAMPLE 43

Preparation of [NH(PEG3400)NHSO$_2$PcAlCl (SO$_3$H)$_2$SO$_2$]$_n$ (NC 100479)

PEG 3400 diamine (Shearwater Polymers, Huntsville, Ala.; 0.391 g, 0.115 mMoles) was dissolved in pyridine (75 mL) with magnetic stirring. Approximately 50 mL pyridine were distilled off under nitrogen from an oil bath at 120–130° to dehydrate the PEG, and then the solution was cooled to ambient temperature and ClAlPc(SO$_2$Cl)$_4$ (prepared from the corresponding acid, Porphyrin Products, Logan, Utah) added (o.111 g, 0.115 mMoles). The solution was stirred for 18 hours at 20° and then refluxed for 30 minutes, after which the solvent was removed on a rotary evaporator at 400 and the residue dissolved in water. This solution was then passed successively through strong acid and strong base (Na form) ion exchange resins to convert the product to the Na salt. Low molecular weight components were removed by diafiltration through a 10,000 membrane (Amicon, Beverly, Mass.) and the dark blue residual liquid evaporated on a rotary evaporator at 40° to yield a dark blue solid (0.09 g).

Size exclusion HPLC analysis indicated that the product had an average molecular weight of 150,000, and it had $\lambda_{max}$ 676 nm (water).

When a solution of this compound in phosphate buffered saline was injected into female immunodeficient mice with HT-29 tumors, 4% of the injected dose was localized in the tumor after one hour.

EXAMPLE 44

Preparation of [NHCH$_2$CH$_2$NHSO$_2$PcAlCl (SO$_3$H)$_2$SO$_2$]$_n$(NC 100477)

This was prepared by the same method used in Example 43, but using ethylenediamine (Aldrich, 0.0058 g, 0.10 mMoles) in place of the PEG diamine. The aqueous solution of the product was diafiltered through a 500 membrane, and the dark blue residual solution ion exchanged to the sodium salt, and evaporated to yield a dark blue solid (0.10 g).

EXAMPLE 45

Preparation of ClAlPc(SO$_2$NHPEG5000)$_4$

The method used was similar to that described in Example 43, but using PEG 5000 α,ω-bis amine (Shearwater Polymers, Huntsville, Ala. ; 2.50 g, 0.50 mMoles), pyridine (50 mL, of which about 30 mL were distilled off), and ClAlPc(SO$_2$Cl)$_4$ (0.10 g , 0.10 mMoles). The solution was refluxed under nitrogen for 30 minutes, and then the solvent was removed. Diafiltration using a 10,000 membrane, collecting the product that did not pass through the membrane, yielded a dark blue solid (0.08 g). It had $\lambda_{max}$ 676 nm (water). When a solution of this compound in phosphate buffered saline was injected into female immunodeficient mice with HT-29 tumors, 2.5% of the injected dose was localized in the tumor after one hour.

EXAMPLE 46

Preparation of [Melamine][SO$_2$ClAlPc(SO$_3$H)$_3$]$_3$ (NC 100478)

ClAlPc(SO$_2$Cl)$_4$(0.10 g, 0.10 Moles) was added to dimethylformamide (1 mL) containing diisopropyl-ethylamine (0.1 mL, 0.57 mMoles) and stirred under nitrogen for 1 hour. Melamine (Aldrich, 0.0022 g, 0.017 mMoles) was then added; it was very sparingly soluble in the reaction mixture. The mixture was stirred at ambient temperatures for 4 days, by which time the melamine had dissolved. The solution was poured over ice, and the resultant blue solution was diafiltered through a 3000 membrane. The dark blue solution that did not pass through the membrane was evaporated to yield a dark blue solid, $\lambda_{max}$ 680 nm (water). When a solution of this compound in phosphate buffered saline was injected into female immunodeficient mice with HT-29 tumors, 0.1% of the injected dose was localized in the tumor after one hour.

EXAMPLE 47

Preparation of a Stable Emulsion of Sudan III

Sudan III (also known as, D&C Red No 17, Solvent Red 23, Cerasin Red) is very water insoluble but soluble in sesame oil, a well known oil for parenteral oil-in-water emulsions (e.g., Intralipid, Lyposin, etc.) and has a $\lambda_{max}$ of 507 nm. Thus, an emulsion of Sudan III was prepared as follows: A saturated solution of Sudan III in sesame oil was prepared by gently rotating the container over the weekend (approx 72 hr). The oil solution was then filtered through a 5 micron syringe filter followed by a 0.8 micron filter to remove undissolved solid Sudan III. The resulting saturated solution was then emulsified in water at a ratio of 10% "oil" to 90% aqueous surfactant solution using ultrasonic energy followed by microfluidization at approx 14,000 PSI until a constant droplet size was achieved. Droplet size was measured by light scattering using a Horiba 910 light scattering device and a volume weighted average. The resulting emulsions were also sterilized by traditional steam sterilization and the droplet size measured again. The results were:

| Formulation | Average Droplet Size (nm) | |
|---|---|---|
| | Before Autoclaving | After Autoclaving |
| 1. 1.2% lecithin, 0.3% F68 | 787 | 909 |
| 2. 1.2% Lecithin, 2% P79 | 141 | 199 |
| 3. 0.8% Lecithin, 3% P79 | 122 | 128 |

P79, described in Example 2k of PCT/GB95/02109, is a PEG-double ester of molecular weight about 10000 and formula $CH_3(CH_2)_{14}COO(CH_2)_{15}COO((CH_2)_2O)_nCH_3$.

P79 is a polymeric surfactant which appears to add greatly to the ability to make a small emulsion droplet of sesame oil saturated with the Sudan III. The resulting rose colored emulsion is stable on the shelf.

This emulsion (Sudan III) may be injected peri-tumorally to migrate to the regional draining lymph nodes for ease of resection. This is currently done in melanoma and breast cancer. These nodes are important for staging the progress of the disease and planning patient management and is known as sentinel lymph node mapping. This emulsion may also make the histopathology easier and more accurate by staining the healthy tissue thereby making the disease tissue more obvious as a filling defect to the emulsion. Further, the emulsion may be administered iv to effect a marking of the healthy tissue of the liver and spleen and other organs which are MPS rich. This will provide visible contrast between the healthy tissue and diseased tissue, lesions, malformations, etc., for ease in surgical resection. Even areas with low or blocked blood flow would be contrasted with normal vascular beds via the content of the blood of the Sudan III emulsion (P79 has been shown to afford prolonged circulation to liposomes and emulsions in corresponding X-ray contrast formulations).

Example 48

Preparation of Nanoparticles of Fluorescein

A nanoparticle suspension of Fluorescein was prepared by placing 7.5 ml of milling beads (0.7 mm zirconium silicate) and 0.9 gm of fluorescein into a 15 ml bottle. Using a stock solution of surfactant, the suspension was made up to 3.3 ml in aqueous phase.

This was done for each of 3 surfactants: Brij 58, Tyloxapol, and Pluronic F-108. The particle sizing results were:

| formulation | Day 3 | Day 5 | Day 6 |
|---|---|---|---|
| F108 | 247 μm | 4.4 μm | 194 nm |
| Tyloxapol | 91 nm | — | — |
| Brij 58 | 101 nm | — | — |

A sterile filtered suspension of fluorescein prepared in this manner was administered subcutaneously to an anesthetized dog with a cannulated thoracic duct to monitor lymph flow and contents. The fluorescein may be detected in the lymph fluid indicating that the dye nanoparticles are passing through the lymphatics thereby marking the lymph nodes as required to aid in the visual identification of lymph nodes for resection and use in cancer staging.

These particles will also function after iv administration in marking tissues rich in MPS cells such that healthy tissue will be marked while disease tissue will remain dark and easily identifiable during surgical resection.

EXAMPLE 49

Formulation of Indocyanine Green in a Liposome

Indocyanine Green (ICG) was added to a liposome suspension formed from 8.2% lecithin (phosphatidyl choline), 0.8% dimyristylphosphatidylglycerol, and 0.1% of a nonionic, polymeric surfactant, P-79 which is designed to impart prolonged blood pool residence to the liposome. The phospholipids and the surfactant were mixed in water using ultrasonic energy from a probe sonicator (Bransonic Sonifier 450, 90% duty cycle, output 10). Liposomes were prepared using a Microfluidics M110S microfluidizer at 14,000 PSI and 4 passes through the interaction chamber of the phospholipid mixture. The resulting liposomes were approximately 100 nm in average diameter as determined by light scattering and remained the same size after autoclave sterilization. In addition, these liposomes were able to pass through a sterile filter (i.e., 0.2 micron pore size). Addition of ICG in sufficient amount to make the suspension approximately 7 mg/ml in ICG did not alter the physical characteristics of the liposomal suspensions. After sterilization under a nitrogen atmosphere, these ICG liposomes were stable for at least 6 weeks at room temperature.

Assessment of the spectral properties of the liposomal ICG relative to ICG dissolved in water or saline demonstrated the impact of the liposomal environment. Both the excitation maximum wavelength and emission maximum wavelength were shifted to lower energies (i.e., higher wavelengths) relative to the homogeneous water solutions. In addition, careful measurements of quantum yield demonstrate at least a 4 fold increase in quantum yield of the liposomal ICG relative to the aqueous ICG solutions. Thus, the dose required for light imaging contrast utility of the liposomal formulation of ICG should be significantly less than that required from a homogeneous aqueous solution of ICG.

EXAMPLE 50

Preparation of 2-[2-[2-(4-isothiocyano)phenoxy-3-[[1,3-dihydro-1,1,-dimethyl-3-(3-sulfopropyl)-2H-benz[e]indol-2-ylidene]ethylidene]-1-cyclohexen-1-yl]ethenyl]-1,1-dimethyl-3-(3-sulfopropyl)-1H-benz[e]indolium, inner salt, sodium salt, Reaction Product with PEG 3,400 α,ω-diamine.

The following reaction scheme was used to produce the title compound:

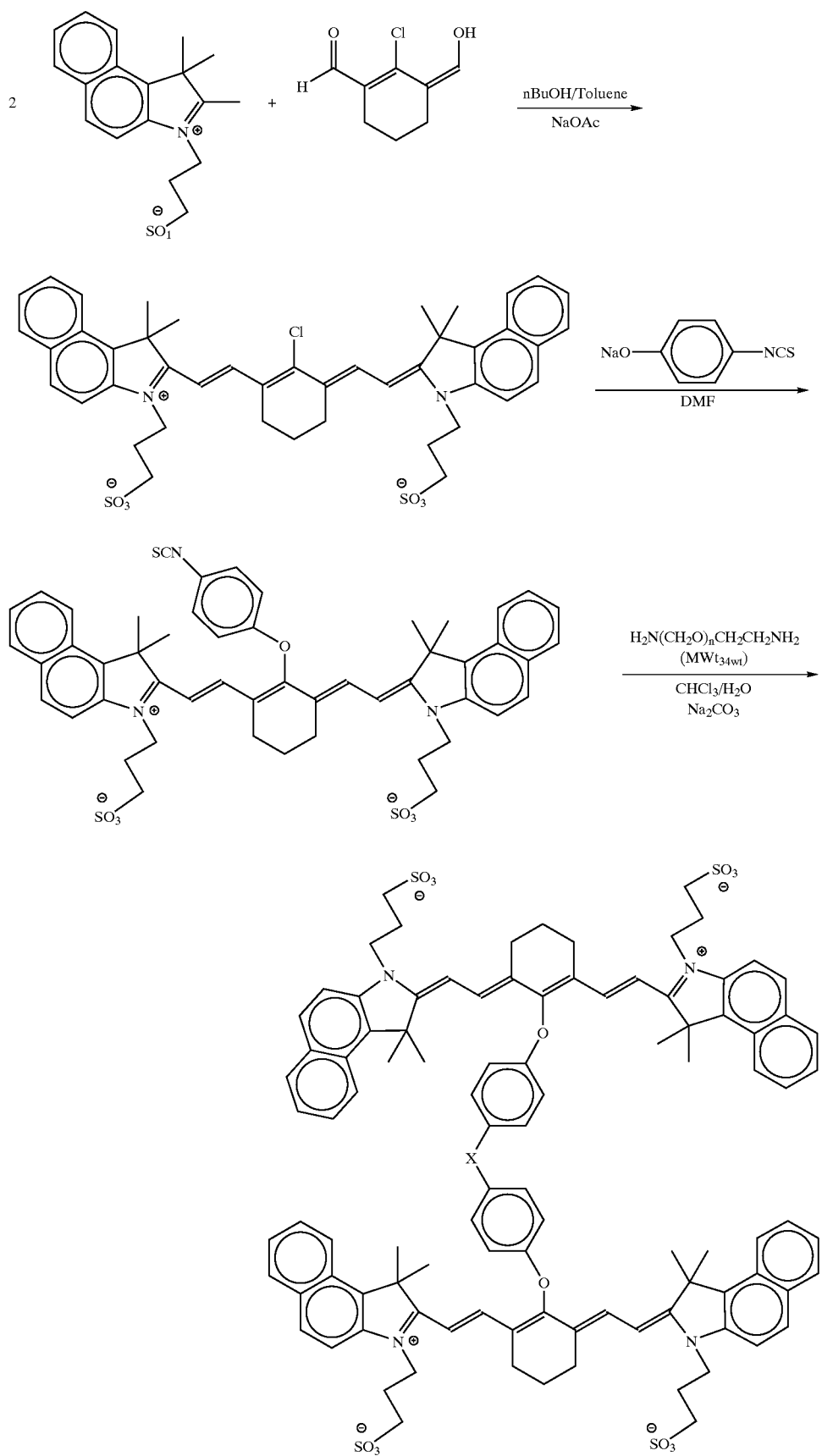

wherein X is NH—CS—NH(CH$_2$CH$_2$O)$_n$CH$_2$CH$_2$NH—CS—NH).

EXAMPLE 51

Preparation of 2-[2-[2-(4-isothiocyano)phenoxy-3-[[1,3-dihydro-1,1,-dimethyl-3-(3-sulfopropyl)-2H-benz[e]indol-2-ylidene]ethylidene]-1-cyclohexen-1-yl]ethenyl]-1,1-dimethyl-3-(3-sulfopropyl)-1H-benz[e]indolinium, inner salt, sodium salt, Reaction product with PEG 10,000 α,ω-diamine The title product was produced analogously to that of Example 50.

EXAMPLE 52

Preparation of Ethyl 3-(N-Acetyl-N-ethylamino)-5-[(5-dimethylamino-1-naphthylsulfonyl)amino]-2,4,6-triiodobenzoate To a stirred solution of of ethyl 3-(N-acetyl-N-ethylamino)-5-amino-2,4,6-triiodobenzoate (11.6 g, 18.5 mmol) in dry pyridine (75 ml) cooled in an ice bath was added 60% NaH oil dispersion (1.8 g, 46.3 mmol). After the reaction with the sodium hydride subsided, dansyl chloride (5 g, 18.8 mmol) was added. The reaction mixture was stirred at ice bath temperature for 4 hours and then at room temperature for 20 hours. After quenching the reaction with acetic acid (10 ml), the brown solution was concentrated on a rotary evaporator. The resulting brown residue was washed with hexanes and then slurried in water (200 ml). The yellow gummy solid was collected, washed with water, dried and then crystallized from ethanol to give 5.3 g (33%) of bright yellow crystals, mp 238–240° C.; ms (FAB) 862 [(M+H), 90%]. The $^1$H-NMR and $^{13}$C-NMR spectra were consistent with the desired product.

Analysis: Calculated for C$_{25}$H$_{26}$I$_3$N$_3$O$_5$S: C 34.86; H 3.05; I 44.20; N 4.88. Found: C 34.91; H 3.02; I 44.53; N 4.74.

EXAMPLE 53

Preparation of 1-[[2-Diethylamino)ethyl]amino]-4-[(methylamino)methyl]thioxanthen-9-one This compound was prepared as described in U.S. Pat. No. 5,346,917 (to Miller et al.); Example 5, mp 241–243° C.

EXAMPLE 54
(see attached synthetic scheme; A→F)

Preparation of α,ω-Bis-(rhodamine B sulfonamide) Analog of Poly(oxyethylene-co-oxypropylene-co-oxyethylene) Block Copolymer with a Block Ratio of 40:20:40 and a Weight Average MW of Approximately 14,600

Synthesis of the α,ω-bis-(amino) analog of poly(oxyethylene-co-oxypropylene-co-oxyethylene) block copolymer with a Block Ratio of 40:20:40 and a Weight Average M.W. of Approximately 14,600 (Compound E)

A total of 50.0 g. of poly(oxyethylene-co-oxypropylene-co-oxyethylene) block copolymer with a block ratio of 40:20:40 and an average molecular weight of approximately 14,600 (Pluronic Surfactant F-108, BASF Corp.) (starting material A, above) was treated with 275 ml of toluene and refluxed for two hours under a Dean Stark trap. The system was then cooled and the trap and its contents (about 25 ml) removed. At this point the reaction mixture was treated with 1.25 ml of thionyl chloride and 0.053 ml of anhydrous dimethylformamide and stirred at 105° for 2 hours. The system was then allowed to stir at room temp. overnight. Next day the reaction mixture was stripped on a rotary evaporator to give 49.35 g of an off-white solid which was readily powdered (intermediate B). In addition to the dominant polyalkylene oxide peaks between 70 and 80 ppm (also seen in the starting Surfactant F-108) the $^{13}$C NMR spectrum of the product contains a singlet at 42.69 ppm, consistent with terminal carbons bearing chlorines, and no remaining peak near 61 ppm where the terminal hydroxyl-bearing carbons of Surfactant F-108 show up.

A total of 49.08 g of intermediate B, 0.89 g of sodium azide, and 2.83 g of potassium iodide were treated with 350 ml of anhydrous dimethylformamide and stirred at 100° for 5 hours under dry argon. The reaction mixture was then stirred at room temperature overnight under argon. It was then stripped on a rotary evaporator at 50° to a melt which solidified to a tan solid. The solid was dissolved in 500 ml of distilled water and shaken with 500 ml of chloroform. Upon layer separation (very slow), the aqueous layer was extracted with two 500 ml portions of chloroform. The three chloroform layers were combined and dried over magnesium sulfate. Upon stripping volatiles, 45.58 g of a white solid was obtained (intermediate C). The $^{13}$C NMR spectrum of the product contains a singlet at 50.6 ppm, consistent with terminal carbons bearing azides, and no remaining peak near 42 ppm from the starting bis-chloride.

A total of 44.05 g of intermediate C was treated with 3.15 g of triphenyl phosphine and 200 ml of anhydrous pyridine. The reaction mixture was stirred under argon at room temperature. The bis-triphenyl phosphine analog prepared in this reaction (intermediate D) was used directly, without isolation, in the next step of the synthesis.

The reaction mixture from the previous step was treated with 200 ml of 30% ammonium hydroxide (aqueous) and stirred at room temperature for 7 hours. The foaming was vigorous, requiring a very large vessel to avoid foam-over. It was then stripped on a rotary evaporator overnight and the residual solid redissolved in 500 ml of chloroform. Following drying over magnesium sulfate the volatiles were stripped to an off white solid comprising 39.31 g. When a phosphorus NMR spectrum of the product indicated that a significant phosphorus signal still remained, a 2.0 g sample of the product was treated with 38 ml of 30% ammonium hydroxide (aqueous) and stirred at 60° for 4 hrs. The reaction mixture was then cooled to room temperature, washed with four-40 ml portions of ether, and restripped on a rotary evaporator. The product is an off white waxy solid comprising 1.46 g (intermediate E) This time no phosphorus signal was found in the phosphorus NMR. Also the $^{13}$C NMR spectrum contained a peak at 41.78 ppm, consistent with the terminal carbons bearing amines, and had no remaining peak near 50 ppm corresponding to the starting bis-azide.

Synthesis of the α,ω-bis-(rhodamine B sulfonamide) analog of poly(oxyethylene-co-oxypropylene-co-oxyethylene) block copolymer with a block ratio of 40:20:40 and a weight average molecular weight of approximately 14,600.

A total of 1.25 g of the α,ω-bis-(amino) analog of Pluronic Surfactant F-108 from above (intermediate E) was treated with 0.026 g of dimethylaminopyridine and 10 ml of anhydrous pyridine. The resulting solution was treated with 0.12 g of rhodamine B sulfonyl chloride (Molecular Probes) and stirred at room temperature under nitrogen overnight. The resulting intensely purple solution was stripped on a rotary evaporator to an intensely purple solid comprising 1.42 g. A total of 1.0 g of the crude product was dissolved in 40 ml of distilled water, filtered through a 0.45 micron nylon filter, and the filtrate diafiltered against distilled water using an 50 ml stirred diafiltration cell (Amicon) containing an Amicon YM-3 (nominal 3000 MW cut-off diafiltration membrane). The diafiltration was continued for 35 turnovers (1,750 ml of diafiltrate removed). Initially, the diafiltrate was intensely purple, but as the purification continued the color intensity diminished till it was virtually colorless at 35 turnovers. The intensely purple retentate was stripped on a rotary evaporator to an intensely purple solid which comprised 0.92 g (final product F). The $^{13}C$ NMR spectrum of the product contains the dominant polyalkylene oxide peaks between 70 and 80 ppm seen in F-108 and all the subsequent intermediates, as well as a new singlet at 45.69 ppm. No remaining peak near 41 ppm, corresponding to the previous bis-amine intermediate, was observed. Size exclusion HPLC studies indicate a single broad peak with a peak molecular weight of approximately 15,000 based on PEG standards. The compound shows a broad spectral absorbance peaking at 584 nm.

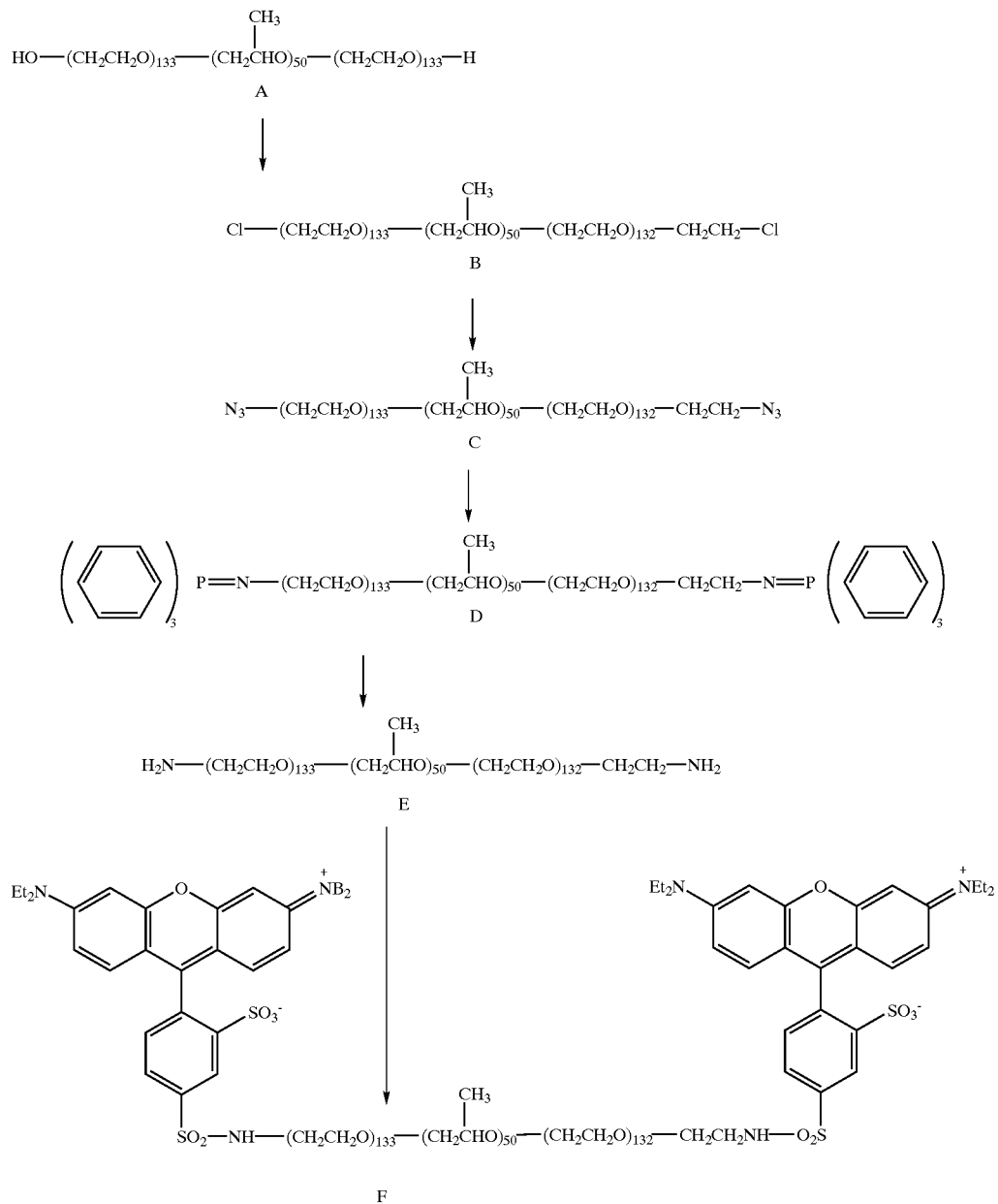

EXAMPLE 55

Synthesis of the Fluorescein Thiocarbamate Derivative of Surfactant T-908

A total of 5.0 9 of Tetronic-908 Surfactant (T-908, BASF, Corp., average molecular weight 25,000) (starting material A below) was treated with 0.10 g of dimethylaminopyridine and 50 ml of anhydrous pyridine. The resulting mixture was treated with 0.15 g of fluorescein isothiocyanate (Molecular Probes, Inc.) and stirred at room temperature under nitrogen overnight. The resulting solution was stripped on a rotary evaporator to a yellow-green solid comprising 5.4 9. A total of 5.1 g of the product was dissolved in 200 ml of distilled water, filtered through a 0.45 micron nylon filter, and the filtrate diafiltered against distilled water in a stirred diafiltration cell (Amicon) containing an Amicon YM-3 (nominal 3000 MW cut-off) diafiltration membrane. The diafiltration was continued for 25 turnovers until the diafiltrate was essentially colorless. The retentate was freeze dried to a yellow-green solid which comprised 3.4 g. The $^{13}$C-NMR spectrum of the product contains the dominant polyalkylene oxide peaks between 70 and 80 ppm as well as aromatic peaks consistent with the fluorescein moiety. Size exclusion HPLC studies indicate a single broad peak with a peak molecular weight of approximately 25,000 based on PEG standards.

EXAMPLE 56

Preparation of a Linear Copolymer of Diethylenetriamine-pentaacetic Acid and 1,6-Diaminohexane Terminated with Fluorescein Amine-terminated Polymeric Ligand A solution of 4.42 g of 1,6-diaminohexane in 68.8 ml of anhydrous dimethylsulfoxide was treated with 13.24 ml of triethylamine and 11.32 g of diethylenetriaminepenta-acetic dihydride. The resulting slurry was stirred under argon overnight. Next morning the moderately viscous polymer dope which had developed was treated with 600 ml of 0.5 M sodium carbonate in water and ultrafiltered to approximately 300 ml in a stirred cell diafiltration unit fitted with an Amicon YM-10 diafiltration membrane (nominal 10 K cutoff). At this point the mode was changed to diafiltration with a 0.5 M aqueous sodium carbonate feed and continued until approximately 1,800 ml of diafiltrate had been produced (approximately 6 turnovers). The feed solution was then changed to distilled water and diafiltration continued until another 1,800 ml of diafiltrate had been produced (6 turnovers). The retentate was then removed and freeze dried to give 7.35 g of a white fluffy polymeric solid. This polymeric ligand was found to have a number average molecular weight of 10000 a weight average molecular weight of 25000 and a dispersity of 2.50.

Fluorescein-terminated Polymeric Ligand

A solution of 3.50 g of the above amine-terminated polymeric ligand was dissolved in 29.6 ml of 0.5M aqueous sodium carbonate was treated with 0.72 g of fluorescein isothiocyanate, isomer 1, and stirred at room temperature under argon for 2 hours. The bright orange solution which resulted was diluted with 40 ml of distilled water and placed in a stirred cell diafiltration unit fitted with an Amicon YM-10 diafiltration membrane (nominal 10K cutoff). It was then diafiltered until approximately 1,450 ml of diafiltrate had been produced (approximately 18 turnovers). The retentate was then removed and freeze dried. An intensely golden yellow, fluffy polymeric solid comprising 3.00 g was obtained. It was found to have a lambda max of 492 nm.

EXAMPLE 57

Preparation of a the Gadolinium Complex of a Linear Copolymer of Diethylenetriaminepentaacetic Acid and 1,6-Diaminohexane Terminated with Fluorescein A 2.00 g portion of the linear copolymer of diethylenetriaminepentaacetic acid and 1,6-diaminohexane terminated with fluoresceins described in Example 56 above was treated with 50 ml of distilled water and stirred at room temperature. In a separate vessel 3.13 g of gadolinium chloride hexahydrate was dissolved in 31.3 ml of distilled water. The gadolinium chloride solution was then poured slowly into the stirring polymer solution which was then stirred at room temperature for an additional 2 hours. The resulting intensely yellow solution was then rinsed into a stirred cell diafiltration unit fitted with an Amicon YM-10 diafiltration membrane (nominal 10K cutoff). It was ultrafiltered down to a retentate volume of approximately 60 ml following which the mode was changed to diafiltration with a distilled water feed. After 1,400 ml of diafiltrate were produced (approximately 18 turnovers) the intensely yellow retentate was removed and freeze dried. An intensely yellow, fluffy polymeric solid was obtained which comprised 1.09 g. Spectral analysis showed the polymer has a lambda max. (absorption) of 499 nm.

EXAMPLE 58

Preparation of a Linear Copolymer of Diethylenetriaminepentaacetic Acid and 1,6-Diaminohexane Terminated with Sulfonated Phthalocyanine A 0.43 g portion of an amine-terminated polymeric ligand made in the same manner as that described in Example 56 above was dissolved in 4.25 ml of 0.5 M aqueous sodium carbonate and stirred in an ice-water bath for 15 min. At this point a total of 0.242 g of powdered aluminumchlorophthalocyanine tetrasulfonyl chloride was slowly added to the cold stirring polymer solution forming a green slurry. The reaction mixture was stirred overnight, allowing the ice to melt and the reaction mixture to come to ambient room temperature. Next morning the reaction mixture had become an intensely green solution. It was rinsed into a stirred cell diafiltration unit fitted with an Amicon YM-10 diafiltration membrane (nominal 10 K cutoff) with 20 ml of distilled water and diafiltered for approximately 13 turnovers. The retentate was then freeze dried, yielding an intensely green fluffy polymeric solid comprising 0.48 g. Spectral analysis showed the polymer has a lambda max. (absorption) of 650 nm.

EXAMPLE 59

Preparation of a Linear Copolymer of Diethylenetriamine-pentaacetic Acid and 1,6-Diaminohexane Terminated with sulfocyanine A 0.568 g sample of amine-terminated polymeric ligand prepared in the same manner as that described in Example 56 above is treated with 4.8 ml of 0.5 M sodium carbonate in water and stirred to form a clear solution. That solution is treated with 0.238 g of the monofunctional sulfocyanine dye sold as Cy-5 monofunctional dye by Nycomed Amersham. The reaction mixture is stirred at room temperature for 2 hours, whereupon the clear, red solution is diluted with 20 ml of distilled water and placed in a stirred cell diafiltration unit fitted with an Amicon YM-10 diafiltration membrane (nominal 10K cutoff). It is then diafiltered for 18 hours with a distilled water feed. Approximately 650 ml of diafiltrate is removed (approximately 26 turnovers of diafiltration) following which the retentate is freeze dried.

EXAMPLE 60

Preparation of the Fluorescein Thiourea Derivative of Surfactant T908 (BASF)

Terminal Amino Derivative of Surfactant T908

A total of 100.0 g of Surfactant T908 (BASF) was treated with 525 ml of toluene and refluxed for an hour under a Dean-Stark trap. The Dean-Stark trap was then removed along with the approximately 25 ml of toluene/water it contained. Upon cooling to room temperature, the reaction mixture was treated with 2.92 ml of thionyl chloride and 0.12 ml of DMF. It was reheated to 105° C. and stirred under argon for 3 hours, cooled to room temp, and stripped on a rotary evaporator to a light tan powder comprising 101.99 g.

A total of 100.0 g of this "chloro-T908" intermediate was treated with 2.08 g of sodium azide, 5.98 g of potassium iodide, and 700 ml of DMF. The reaction mixture was heated to 100° C. for 6 hours, cooled to room temperature, and then stripped on a rotary evaporator at 69° C. The crude product was dissolved in 900 ml of distilled water and shaken with 1 liter of chloroform. The chloroform layer was collected and combined with two additional 500 ml chloroform washes of the aqueous layer. After drying the combined chloroform layers over magnesium sulfate the chloroform was stripped on a rotary evaporator to give 65.69 g of a light tan frangible solid.

A total of 62.5 g of this "azido-T908" intermediate was dissolved in 300 ml of anhydrous pyridine and treated with 6.56 g of triphenylphosphine. After stirring it at room temperature for 18 hours, the resulting clear solution was treated with 300 ml of 30% ammonia (aqueous) and stirred under argon at 50° C. for 5 hours. It was then stripped on a rotary evaporator and subsequently treated with 562.5 ml of DMSO and 2,250 ml of distilled water. The resulting solution was diafiltered for 12 turnovers using a Millipore spiral wound permeator with a nominal 10K cutoff. The final retentate was freeze dried yielding 43.22 g of an off-white powder. A high field $^{13}$C NMR of the product showed a peak at 41.78 ppm, consistent with that expected for the methylene adjacent to the terminal amine of the desired product, and showing no aromatic peak in either the $^{13}$C or $^{1}$H or spectra as well as no peaks in the $^{31}$P spectrum indicating the triphenylphosphine adduct has been completely converted to the desired amino adduct.

Terminal Fluorescein Derivative of Surfactant T908

A total of 1.00 g of the above terminal amino derivative of Surfactant T908 was dissolved in 10 ml of distilled water and then treated with 3.2 ml of 0.5M aqueous sodium carbonate. The resulting clear solution was treated with 0.156 g of fluorescein isothiocyanate, isomer I (Aldrich) and stirred at room temperature for 18 hours. The resulting clear intensely orange solution was diluted with 60 ml of distilled water and placed in a stirred diafiltration cell fitted with an Amicon YM-10 (nominal 10K cut-off diafiltration membrane. It was initially ultrafiltered down to a retentate volume of 25 ml and was subsequently diafiltered until 600 ml of diafiltrate had been removed (24 turnovers). The retentate was then freeze dried to a bright orange fluffy polymeric solid comprising 0.43 g. Spectral analysis showed the polymer has a lambda max. (absorption) of 307 nm.

EXAMPLE 61

Preparation of a Derivative of the Polymeric BASF Surfactant T908 Terminated with Sulfocyanines A total of 0.30 g of the terminal amino derivative of Surfactant T908 described in Example 60 is dissolved in 3.0 ml of distilled water and treated with 2.9 ml of 0.5M aqueous sodium carbonate. The resulting clear solution is treated with 0.19 g of the sulfoindocyanine dye sold as Cy-7 dye by Amersham and stirred at room temperature for 18 hours. The resulting clear solution is diluted with 6 ml of distilled water and placed in a stirred diafiltration cell equipped with an Amicon YM-10 (nominal 10K cutoff) diafiltration membrane. It is diafiltered until about 250 ml of diafiltrate had been removed (about 20 turnovers). The retentate is freeze dried.

EXAMPLE 62

Preparation of carboxylic acid Substituted benzofluoresceins 2,7-Dihydroxynaphthalene and an X-substituted phthalic anhydride (e.g. X=NO$_2$, SO$_3$H, MeO, halogen, CN, COOH, COOR as an ester such as COOMe, ether, thioether, sulphonamide, amide and the like) are mixed and heated together in the melt using excess anhydride as a molten solvent in the presence of a Lewis acid such as zinc chloride to produce the desired compound. This chromophore can be halogenated or sulfonated or carboxylated by the usual methods to produce novel chromophores with added functional groups for solubility modification; for further synthetic elaboration by reduction and displacement reactions; for attachment to anchoring vectors such as antibodies, peptides such as Sta peptide; and for attachment to polymers such as PE.g. The material can be radiolabeled with an isotope of iodine by treatment with a source of such isotope such as an isotope as an iodinium ion (e.g. iodine chloride or diiodine and the like).

EXAMPLE 63

Preparation of sulfonic acid Substituted benzofluoresceins 2,7-Dihydroxynaphthalene and an X-substituted 2-sulfobenxoic acid cyclic anhydride (e.g. X=NO$_2$, SO$_3$H, MeO, halogen, CN, COOH, COOR as an ester such as COOMe, ether, thioether, sulphonamide, amide and the like) are mixed and heated together in the melt using excess anhydride as a molten solvent in the presence of a Lewis acid such as zinc chloride to produce the desired compound. This chromophore can be halogenated or sulfonated or carboxylated by the usual methods to produce novel chromophores with added functional groups for solubility modification; for further synthetic elaboration by reduction and displacement reactions; for attachment to anchoring vectors such as antibodies, peptides; and for attachment to polymers such as PE.g. The material can be radiolabeled with an isotope of iodine by treatment with a source of such isotope such as an isotope as an iodinium ion (e.g. iodine chloride or diiodine and the like).

EXAMPLE 64

Preparation of a PEG Derivative of a pH Sensitive napthindolecycanine Dye (amide Linkage via a 4-carboxylic acid of the Central Cyclohexene Ring)

134 mg of phenyl -N-phenylphosphoramidochloridate (Aldrich) is added to a solution of 430 mg of 4-carboxylic acid-1-hydroxycyclohexene rigidified bis(-3-sulfopropyl-1 H-1,1-dimethyl-benzindole) C7 cyanine dye and 0.2 ml triethylamine in methylene chloride. The mixture is stirred at room temperature under a nitrogen atmosphere for about 30 mins. To the above solution, dropwise for 30 mins, is added a solution of 2.5 g methoxy poly(ethyleneglycol)amine MW 5,000 and 0.07 ml triethylamine in methylene chloride. This is stirred at room temperature under a nitrogen atmosphere for approximately one day or until complete reaction was observed. The volatiles were removed from the reaction mixture by placing under reduced pressure. The resulting residue was purified by chromatography ($SiO_2$, 15–20% methanol in chloroform) giving the desired amide linked cyanine dye.

EXAMPLE 65

Preparation of N-[5-anilino-3-chloro-2,4-(2-ethoxycarbonylpropane-1,3-diyl)-2,4-pentadien-1-ylidene]anilinium chloride To 34 ml of anhydrous N,N-dimethylformamide, stirred under nitrogen and moderated at 0 to 5° C. by a Dry Ice/isopropanol bath, was added, dropwise over 20 minutes, 28 ml of phosphorous oxychloride. The reaction mixture was allowed to warm for 1 h to 15° C. To this was then added, dropwise over 5 minutes, a solution of 10 g of ethyl 4-oxocyclohexanecarboxylate (Aldrich Chemical Co.) in 20 ml of methylene chloride. After a brief exotherm had subsided, the reaction mixture was heated to reflux for 2 hours. The solvent was then removed by rotary evaporation, and the dark orange viscous residue was cooled in ice. To this was added, over 35 minutes, a solution of 22 ml of aniline dissolved in 22 ml of ethanol. The addition was accompanied by an evolution of fumes and a rise in temperature that was moderated using an ice-salt bath. After the addition was completed, the viscous reaction product was poured over 250 g of ice containing 25 ml of concentrated hydrochloric acid. This mixture was then allowed to stand in a freezer for 2 days. The crude product was isolated by filtration, washed with water and then with ether, and dried over $P_2O_5$ under vacuum to give 14 g of solid. This material was used without further manipulation.

EXAMPLE 66

Preparation of 3-(2,3,3-trimethyl-1H-benz[e]indolio) propanesulfonate

To a magnetically stirred solution of 8.72 g of 1,1,2-trimethyl-1H-benz[e]indole (Fisher Chemical Co.) in 100 ml of anhydrous acetonitrile under nitrogen at room temperature was added 5.09 g of 1,3-propane sultone (Aldrich Chemical Co.) in 3 ml of acetonitrile. The reaction mixture was heated to reflux for 24 hours, and then cooled to ambient temperature. The off-white precipitate was isolated by filtration from the accompanying dark green liquid, washed with 100 ml of acetonitrile and then with 100 ml of ether, and then dried in air to provide 10.24 g of desired compound.

EXAMPLE 67

Preparation of 2-[2-[2-chloro-3-[[1,3-dihydro-1,1,-dimethyl-3-(3-sulfopropyl)-2H-benz [e]indol-2-ylidene]ethylidene]-5-(ethoxycarbonyl)-1-cyclohexen-1-yl]ethenyl]-1,1-dimethyl-3-(3-sulfoprpoyl)-1H-benz[e]indolium, inner salt, sodium salt.

A mixture of 1.87 g of N-[5-anilino-3-chloro-2,4-(2-ethoxycarbonylpropane-1,3-diyl)-2,4-pentadien-1-ylidene] anilinium chloride and 4.3 g of 3-(2,3,3-trimethyl-1H-benz [e]indolio)propanesulfonate in 190 ml of n-butanol containing 75 ml of toluene was heated at reflux for one hour with the removal of water. To the mixture was then added 0.65 g of anhydrous sodium acetate, and reflux was continued for another two and one half hours. The solvent was then removed by distillation to a point were crystals began to form. After cooling, the crystals were isolated by filtration, triturated with ethyl ether, and then recrystallized from methanolic ethyl ether to give 1.7 g of the desired compound.

EXAMPLE 68

Preparation of the bisthioether 2:1 dye:polymer reaction product between 2-[2-[2-chloro-3-[[1,3-dihydro-1,1,-dimethyl-3-(3-sulfopropyl)-2H-benz[e] indol-2-ylidene]ethylidene]-5-(ethoxycarbonyl)-1-cyclohexen-1-yl]ethenyl]-1,1-dimethyl-3-(3-sulfopropyl)-1H-benz[e]indolium, inner salt, sodium salt and disodium $PEG_{3,400}$-α,ω-dithiolate, Polymer 3

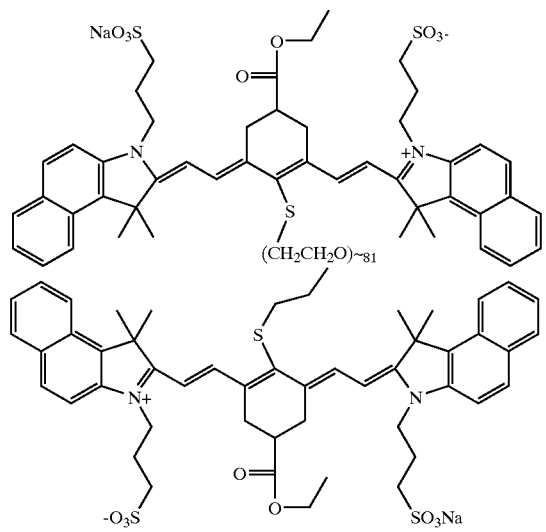

A solution of 1.9 g of 3,400 molecular weight poly (ethylene glycol)-α,ω-dithiol from Shearwater Polymers, Inc. in 8.5 ml of dry and nitrogen-sparged dimethylformamide was treated with 0.1 g of 50% sodium hydride, and then added dropwise under nitrogen at room temperature over 15 minutes to a stirred solution of 0.89 g of 2-[2-[2-chloro-3-[[1,3-dihydro-1,1,-dimethyl-3-(3-sulfopropyl)-2H-benz[e]indol-2-ylidene]ethylidene]-5-(ethoxycarbonyl)-1-cyclohexen-1-yl]ethenyl]-1,1-dimethyl-3-(3-sulfoprpoyl)-1H-benz[e]indolium in 9 ml of nitrogen-sparged, anhydrous dimethylformamide. After two and one half hours, the reaction mixture was treated with excess carbon dioxide, the solvent was evaporated, and the desired 2:1 dye:polymer adduct was isolated by column chromatography (SiO2: 15% methanol in chloroform).

Biodistribution results are presented in FIGS. 2A (one hour post-dosing) and 2B (three hours post-dosing).

EXAMPLE 69

Preparation of the bisthioether 2:1 dye:polymer reaction product between 2-[2-[2-chloro-3-[[1,3-dihydro-1,1,-dimethyl-3-(3-sulfopropyl)-2H-benz[e]indol-2-ylidene]ethylidene]-5-(ethoxycarbonyl)-1-cyclohexen-1-yl]ethenyl]-1,1-dimethyl-3-(3-sulfopropyl)-1H-benz [e]indolium, inner salt, sodium salt and disodium $PEG_{10,000}$-α,ω-dithiolate

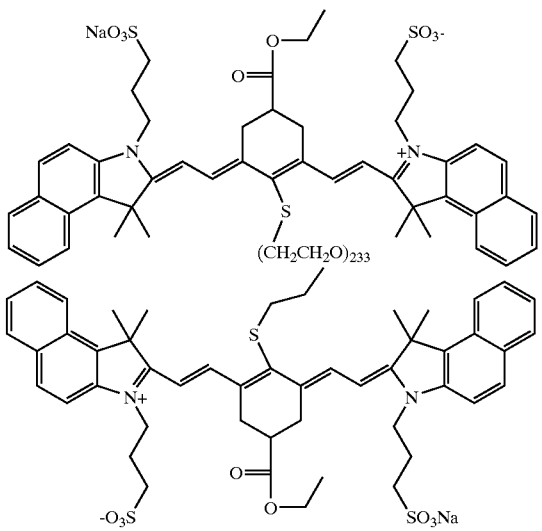

A solution of 2.45 g 10,000 molecular weight poly (ethylene glycol)-α,ω-dithiol from Shearwater Polymers, Inc. in 14 ml dry and nitrogen sparged dimethylformamide was treated with 43 mg 50% sodium hydride and 1.5 ml dry dimethylformamide. After about one half hour this solution was added dropwise in one third hour to a nitrogen sparged solution of 0.4 g of 2-[2-[2-chloro-3-[[1,3-dihydro-1,1-dimethyl-3-(3-sulfopropyl)-2H-benz[e]indol-2-ylidene]ethylidene]-5-(ethoxycarbonyl)-1-cyclohexen-1-yl]ethenyl]-1,1-dimethyl-3-(3-sulfoprpoyl)-1H-benz[e]indolium in 5 ml dry nitrogen sparged dimethylformamide, with stirring. After four hours of stirring under a nitrogen atmosphere, the reaction mixture was treated with excess carbon dioxide followed by evaporation of the solvent. The desired dark green 2:1 dye:polymer adduct was isolated by column chromatography ($SiO_2$: 20% methanol in chloroform). Absorption maxima in phosphate buffered saline: 814 nm, 744 nm. The mass spectrum had a distribution centered approximately at 12,000 mass units, as expected.

EXAMPLE 70

Preparation of a Derivative of the Polymeric BASF Surfactant T908 Terminated with Zinc Trisulfophthalocyanine Groups (NC 100526)

This dye was made from the Surfactant T908 amino derivative (2.50 g, 0.1 mM) by a method analogous to that of Example 61 but using a tenfold excess of zinc phthalocyanine tetrasulfonyl chloride (4.0 g, 4.1 mM) The diafiltrate retentate (10,000 MW membrane) was evaporated and freeze dried to yield a dark blue solid, 3.2 g, lambda max. 635 nm (shoulder at 671 nm) in water.

EXAMPLE 71

Preparation of $[PcAlCl(SO_3H)_3SO_2NH]_2[PEG\ 10,000](NC\ 100481)$

This was prepared by a method analogous to that used in Example 43 but using PEG 10,000 diamine (Shearwater Polymers, 1.0 g, 0.1 mM) and an excess of chloro-aluminumphthalocyanine tetrasulfonyl chloride (0.217 g, 0.22 mM). The diafiltrate retentate (3,000 MW membrane) was evaporated to yield a dark blue solid, 0.82 g, lambda max. 675 nm in water.

EXAMPLE 72

Preparation of $ClAlPc[SO_2NH(CH_2)_2N^+(CH_3)_3]_4\ 4Cl^-$

This dye was prepared by a method analogous to that of Example 56, but using chloro-aluminumphthalocyanine tetrasulfonyl chloride (1.25 g, 1.29 mM) and (2-aminoethyl)-trimethylammonium chloride hydrochloride (Aldrich, 1.0 g, 5.7 mM, 10% excess). The diafiltrate retentate (500 MW membrane) was evaporated to yield a dark blue solid, 0.44 g, lambda max. 677 nm in water.

EXAMPLE 73

Preparation of $ZnPc(SO_3H)_8$

1. Disulfonation of o-toluic acid

Fuming sulfuric acid (30% oleum, 150 mL.) was added to o-toluic acid (50.0 g, 0.37 mol.) with stirring, causing an exotherm to 85° C. The solution was heated at 170° C. for 6 hours. An additional 50 mL of fuming sulfuric acid were added, and the solution heated for an additional 6 hours. The cooled solution was then poured over ice, and the product neutralized to pH 7 with solid calcium carbonate. The precipitated calcium sulfate was filtered, and the solution used for the next step.

2. Oxidation of disulfo-o-toluic acid Solution

The solution from step 1 (100ml.) was stirred and heated almost to boiling, and solid potassium permanganate added in 1 g increments until the solution attained a permanent purple color. The excess permanganate was destroyed by the addition of ethanol, the precipitate was filtered, and the resultant pale yellow solution was freed of metal ions by passage through the acid form of a strong acid ion exchange resin (AG 50W-X8, Bio-Rad). The eluate was evaporated to dryness on a rotary evaporator, whereupon it crystallized. The product 3,5-disulfophthalic acid was identified by electrospray MS, (M–H)⁻ peak at 325 (theor.=325)

3. Preparation of zinc Dhthalocyanine octasulfonate

An aqueous solution of 3,5-disulfophthalic acid (6.4 g) is neutralized to pH 4 with ammonium hydroxide, and the solution evaporated to dryness. This solid is mixed with urea (10.0 g), zinc acetate (1.8 g), ammonium chloride (0.8 g), ammonium molybdate (0.12 g), boric acid (0.12 g), and sulfolane (12.5 mL), and the mixture heated with stirring under nitrogen at 220° C. for 3 hours. The mixture is cooled, the solvent decanted, and an aqueous solution of the residue is chromatographed on cellulose to yield the zinc phthalocyanine octasulfonate as a dark blue powder.

EXAMPLE 74

Preparation of $^{99m}Tc$ derivatives of the phthalocyanines of Example 73

These derivatives are prepared by the method described in Example 73 but using sodium pertechnetate ($Na^{99m}TcO_4$, from a generator) together with a reducing amount of hydroxylamine (8 M/M pertechnetate) in place of zinc acetate.

Chromatographic separation yields blue 1:1 Pc/Tc complexes, and green 2:1 Pc/Tc complexes.

EXAMPLE 75

Preparation of cyanine Dye Containing 5 sulfo Groups

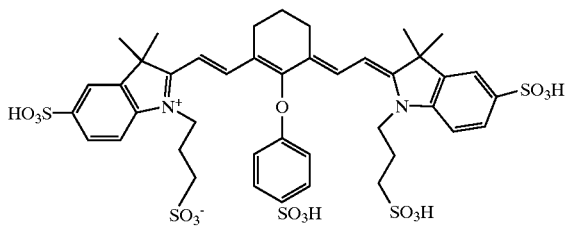

1. Preparation of 1-(γ-sulfonatoproyl)-2,3,3-trimethylindoleninium-5-sulfonate

The potassium salt of 2,3,3-trimethylindolinium-5-sulfonate was prepared by the method of Mujumdar et al. (Mujumdar, Ernst, Mujumdar, Lewis, and Waggoner, Bioconj. Chem. 1993 4(2) 105). This salt (42.0 g, 0.15M), 1,3-propanesultone (25.0 g, 0.20M), and acetonitrile (500 mL) were refluxed under nitrogen for 4 hours. The pale yellow supernatant liquid was decanted from the precipitated red-blue solid, and the solid washed twice with acetonitrile. It was then stirred with isopropanol (800 mL) for 2 days, and the resultant finely divided solid filtered, washed with isopropanol, and dried under vacuum to give the product (43.5 g, 72%).

2. Preparation of cyanine Dye

The above potassium salt (8.0 g, 0.02M) and 2-chloro-1-formyl-3-(hydroxymethylene) cyclohex-1-ene (1.7 g, 0.01 M) were dissolved in a mixture of acetic anhydride (60 mL) and acetic acid (40 mL) under nitrogen. Diisopropylethylamine (6 mL) was then added, and the solution stirred for 2 days. The mixture was then filtered, the solvents evaporated, and the residue treated with 95% ethanol (500 mL), stirred, and filtered. The precipitated solid was washed with 95% ethanol (500 mL), and dried under vacuum at 40° C. The product was a dark green solid, 5.3 g (55%), $\lambda_{max}$ 780 nm. FAB-MS was carried out on the acid form of the dye, obtained by ion exchange chromatography, found $MH^+$=859 (theor.=859). TLC ($SiO_2$, 40% methanol in methylene chloride) showed a high degree of purity, and no further purification was carried out.

3. Preparation of cyanine Dye sulfophenyl Derivative

Phenol-4-sulfonic acid dihydrate (Acros, 0.23 g, 1.0 mM) in DMF (20 mL) was stirred under nitrogen in an ice bath and sodium hydride (Aldrich, 60% dispersion in mineral oil, 0.12 g, 3.0 mM) in DMF (10 mL) added. After stirring for 10 minutes, this solution was added to the product from step 2 (0.83 g, 0.9 mM) in DMF (35 mL) and the mixture allowed to stir for 3 days. The solution was acidified with acetic acid, ether (500 mL) added, and the resultant precipitate filtered and washed with ether. The product was purified by chromatography on silica using 40% methanol in methylene chloride as eluant. The dark green eluate was collected and evaporated to yield a dark blue-green solid (0.39 g), 773 nm. This was purified by dissolution in the minimal amount of methanol and precipitation with excess isopropanol. FAB-MS was carried out on the acid form of the dye (obtained by ion exchange), found $MH^+$=997 (theor.=997).

EXAMPLE 76

Preparation of cyanine Dye Containing 7 sulfo Groups

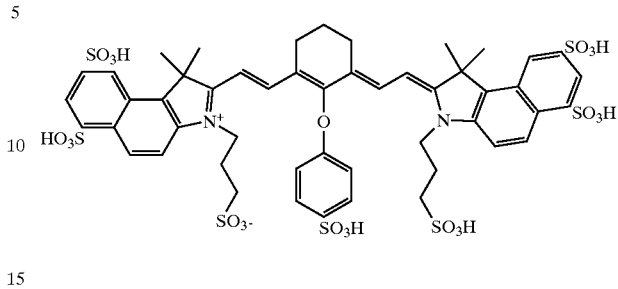

The potassium salt of 2,3,3-trimethylbenzindoleninium-5,7-disulfonate is prepared by the method of Mujumdar et al. (Mujumdar, Mujumdar, Grant, and Waggoner, Bioconj. Chem., 1996 7(3) 356). Subsequent steps are carried out by the method of Example 75.

EXAMPLE 77

Preparation of cofacial SiPc-PEG 3400 Alternating polymer

Silicon phthalocyanine dihydroxide (Aldrich, 1.0 mM), imidazole (Aldrich, 3.0 mM), and DMF (2 mL) are stirred under nitrogen for 5 minutes. 3-Isocyanatopropyl-dimethyl-chlorosilane (Gelest, 2.0 mM) are added and the mixture stirred for 48 hours. Methanol (5 mL) is added, the solution filtered, and the solvents removed under vacuum. The residue is chromatographed on silica, eluting with toluene containing increasing concentrations of methanol. The blue eluate containing the required product is collected and the solvent removed under vacuum. This product (1.0 mM) in isopropanol (10 mL) is mixed with a solution of PEG 3400 diamine (Shearwater Polymers, 1.0 mM) in isopropanol (10 mL) and heated with stirring under nitrogen at 40° C. for 5 hours. The solvent is removed under vacuum, and the required product isolated by chromatography on silica.

EXAMPLE 78

Preparation of Cofacial AlPc-PEG 10,000 Compound

Aluminum phthalocyanine hydroxide (Aldrich, 1.0 mM), imidazole (Aldrich, 3.0 mM), and DMF (2 mL) are stirred under nitrogen for 5 minutes. 3-Isocyanatopropyl-dimethyl-chlorosilane (Gelest, 2.0 mM are added and the mixture stirred for 48 hours. Methanol (5 mL) is added, the solution filtered, and the solvents removed under vacuum. The residue is chromatographed on silica, eluting with toluene containing increasing concentrations of methanol. The blue eluate containing the required product is collected and the solvent removed under vacuum. This product (2.0 mM) in isopropanol (10 mL) is mixed with a solution of PEG10,000 diamine (Shearwater Polymers, 1.0 mM) in isopropanol (10 ml) and heated with stirring under nitrogen at 40° C. for 5 hours. The solvent is removed under vacuum, and the required product isolated by chromatography on silica.

EXAMPLE 79

Thiourea Linked 5-fluorescein to STa (syn. 2): NC100506

A solution of 0.12 mg 5-fluorescein isothiocyanate (Molecular Probes) and 0.24 mg heat stable E-coli enterotoxin STa (syn 2, Bachem) (Scott Waldman, U.S. Pat. No. 5,518,888) in 0.32 ml 0.1M borate buffer (pH 8.3) was sonicated for one hour with a temperature (external) rise from room temperature to about 40 degrees centigrade. This solution was allowed to sit stoppered at room temperature an additional half hour at which time 0.03 ml of glacial acetic acid was added and mixed into the reaction mixture.

The product had a retention time (RP C18 HPLC) which was longer than the starting peptide and shorter than 5-fluorescein isothiocyanate. Isolation and purification were done using the same HPLC conditions yielding about 0.1 mg yellow product. Ultra violet maxima in 1/1 water/methanol 10 mM ammonium acetate were: 202 nm (a 0.822), 277 nm (a 0.096), 457 nm (a 0.096), 482 nm (a 0.107). Mass spectrum (electrospray, negative): M–H 2359; M+Na 2381; theoretical M 2360. The conjugate tested positive as a competitive inhibitor of the STa receptor.

strated the impact of the liposomal environment. Both the excitation maximum wavelength and emission maximum wavelength were shifted to lower energies (i.e., higher wavelengths) relative to the homogeneous water solutions. In addition, estimates of quantum yield suggest at least a 4 fold increase in quantum yield of the liposomal ICG relative to the aqueous ICG solutions. Thus, the dose required for light imaging contrast utility of the liposomal formulation of ICG should be signficantly less than that required from a homogeneous aqueous solution of ICG. Further, these liposomes have been demonstrated to provide adequate vascular and liver imaging by CT X-ray examination in rabbits after bolus injection of up to 3 ml/kg. Therefore, either modality could be used to confirm the distribution of the agent in the body after adminstration and to confirm the analysis by one with the other.

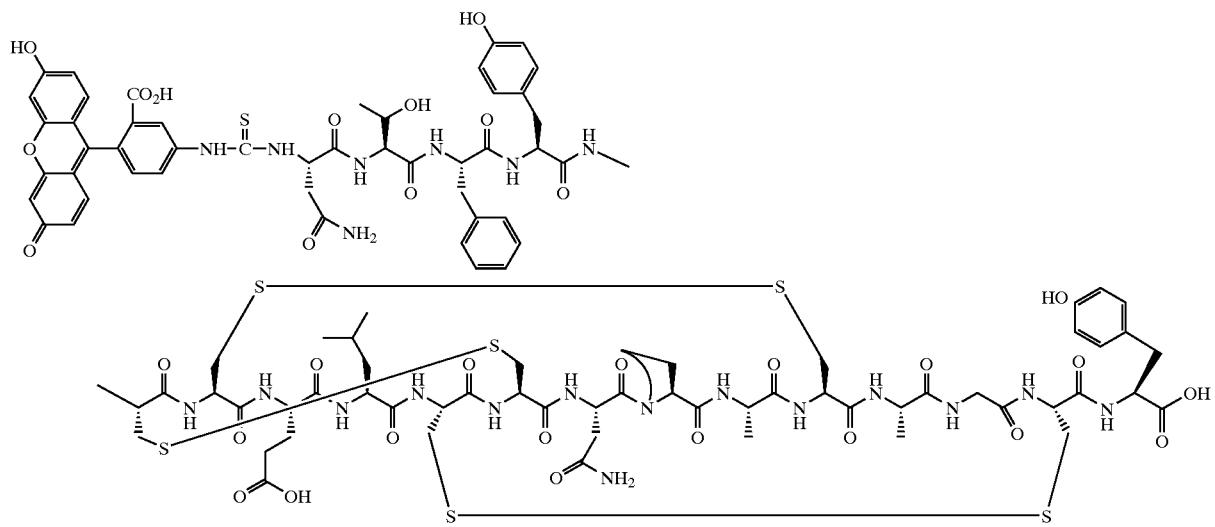

NC100506

EXAMPLE 80

Formulation of Indocyanine Green in a CT-X-ray Diagnostic Liposome

Indocyanine Green (ICG) was added to a CT-X-ray diagnostic liposome suspension (i.e., CTP-10) formed from 8.2% lecithin (phosphatidyl choline), 0.8% dimyristalphosphatidylglycerol, and 0.1% of a nonionic, polymeric surfactant, P-79 which is designed to impart prolonged blood pool residence to the liposome. The phospholipids and the surfactant were mixed in a solution of 40% iohexol (i.e., Omnipaque) at 80° C. using ultrasonic energy from a probe sonicator (Bransonic Sonifier 450, 90% duty cycle, output 10). Liposomes were prepared using an extruder (Avestin, Canada) with 6×1 micron pore size filters. The resulting liposomes were approximately 600 nm in average diameter as determined by light scattering and remained the same size after autoclave sterilization. Addition of ICG in sufficient amount to make the suspension approximately 7 mg/ml in ICG did not alter the physical characteristics of the liposomal suspensions. After sterilization under a nitrogen atmosphere, these ICG liposomes were stable for at least 6 weeks at room temperature.

Assessment of the spectral properties of the liposomal ICG relative to ICG dissolved in water or saline demon-

EXAMPLE 81

Production of a particulate suspension containing 1, 1',3,3,3',3'-hexamethylindotricarbocyanine iodide 7.6 mg Hexamethylindotricarbocyanine iodide and 0.2 g of a copolymer of lactic and glycolic acid having a molecular mass of about 15000 g/mol are dissolved in 2.5 ml methylene chloride. The solution is added with vigorous stirring to 20 ml of a 2% gelatine solution previously autoclaved at 121° C. for 15 minutes. Stirring is continued for 45 minutes. The resulting suspension is used in portions of 5 ml to fill 20 ml glass vessels and frozen directly with liquid nitrogen. The frozen suspension is then freeze dried. After resuspending one portion with 5 ml of 0.9% saline solution the suspension contains about $10^{10}$ hexamethylindotricarbocyaniniodide-containing particles per ml with a particle size of about 1–10 μm.

EXAMPLE 82

Part A: MR Imaging Studies

The compositions of Examples 23, 24, 26, 27 and 28 were imaged in a Rabbit V-2 (carcinoma) Tumor Model as follows. The dose of each composition was adjusted to 0.1 mmol Gd per Kg, i.e., the concentrations were adjusted respectively to 102 mM, 124 mM, 49 mM, 131 mM, and 53.5 mM solutions. For each example, 3 rabbits were employed. Rabbits were anaesthetized, injected and imaged on a standard magnetic resonance imaging device. Axial pre-contrast and post-contrast scans at time intervals of t=0 (immediately after injection), 15 min, 30 min, 60 min and 24 hr were made in 3 mm slices (5 mm apart) of areas from the liver to the legs. Plots of relative enhancement vs. time were derived from three regions of interest (ROI) from enhancing tumor in the right leg, three ROI from enhancing tumor in the left leg and one ROI from muscle.

The compositions exhibited outstanding image enhancement and dramatically improved uptake in the tumor model as compared to a Magnevist® control.

Part B: Sonodynamic Therapy

A sonodynamically effective amount pf ultrasound can be administered to the animals in Part A to cause cytopathogenic changes in the tumor(s) imaged in Part A.

EXAMPLE 83

Enhancement of Cell Killing In vitro in the Presence of chloroaluminum phthalocyanine tetrasulfonate Sonication Procedure In vitro HL-60 human peripheral blood promyelocytic leukemia cells (American Type Culture Collection, Rockville, Md.) were grown at 37° C. in a 5% $CO_2$/air atmosphere, in a 1:1 mixture of DMEM and IMEM fortified with 10% fetal bovine serum. Before use, the cells were centrifuged (5 min. at 1500 rpm), washed with phosphate buffered saline (PBS), and then resuspended in PBS, the volume being adjusted to provide cell suspensions containing $5 \times 10 \times 10^5$ cells/ml. These were stored in crushed ice until used.

Viability was assessed by staining with Trypan Blue dye. 50 μl of the suspension were mixed with 50 μl of Trypan Blue solution (0.4%, Sigma), and the cell concentration counted using a Neubauer-type hemocytometer. Four or five large squares were counted, the blue (dead) cells being counted separately from the unstained (live) cells, and the results averaged. The averaged number of live cells, multiplied by $2 \times 10^4$ gave the cell count per mL. The cell viability was derived from the ratio of the live cells to the total number of cells. Only cultures with a viability of >90% were used.

1.5 ml Aliquots of the cell suspension were transferred to 10×75 mm disposable glass culture tubes (previously blown with air to remove any dust particles), and diluted with 150 μl of PBS, unless a chemical compound was being tested for its sonodynamic potential, in which case 150 μl of a PBS solution of that material was added in place of the PBS. In general, the chemical-containing sonicated solutions contained 0–300 μg of the chemical per ml. The tubes were rotated (35±5 revolutions/min.) around their long axis by insertion into an overhead stirrer securely mounted centrally over a sonicating bath (Branson, Model 1210, frequency 47 kHz). The suspensions were also magnetically stirred by means of a small PTFE-coated stirring bar. The voltage supplied to the sonicating bath could be controlled by a variable transformer. The bath was filled to the mark with distilled water, and degassed by sonication before use. The glass tubes were immersed into the bath so that the liquid level in the tube was ¼ inch below the level in the bath. Sonications were carried out at ambient temperatures, and there was no significant rise in cell suspension temperature during the procedure.

For insonation, the voltage was set to the required value, the power was turned on, and the sample exposed for the required amount of time (secs.). Viability was again assessed with Trypan Blue, the samples were then centrifuged for 5 minutes at 2000 rpm, and a sample of cell free supernatant liquid taken for lactate dehydrogenase (LDH) measurement. Cells whose membranes had been disrupted by the sonication process (dead cells) released LDH into the PBS solution, live cells did not. The LDH was measured by a standard procedure using a Beckman Synchron CX5CE Instrument, the results were measured in IU/l, and afforded a quantitative measurement of cell death in the samples.

A HL-60 cell suspension containing 531000 cells/ml PBS, 92% viability, was used. Samples were insonated as described above for 120 seconds with the sonicator voltage set at 65 volts. Chloroaluminum phthalocyanine tetrasulfonate (148 nanomoles/ml) was added and samples were insonated for 60 and 120 seconds. The results are shown in FIG. 1, comparing the mean effects of ultrasound on the suspensions of the HL-60 cells in the absence (diamonds and dashed mean line) and presence (squares and solid mean line) of chloroaluminum phthalocyanine tetrasulfonate.

Cell death was measured using an LDH assay as described above. Pearson (0.80) and Spearman (0.68) correlation coefficients between total cell deaths and LDH levels were estimated and tested for their equality to zero using $p<0.05$ for significance. Group means were compared using a 1-Way Anova Model followed by a Tukey Honest Significant Difference (HSD) Test using 0.05 at the overall false positive error rate.

EXAMPLE 84

Tumor Cell Killing In vivo by the Synergistic Interaction of a Sonodynamic Agent and Focused Ultrasound with Second Harmonic Imposition A sonodynamically effective dose of a sonodynamic therapy agent is injected into the tail vein of a tumoured mouse. After sufficient time has elapsed to allow the agent to be localized in the tumor, the mouse is anaesthetized and supported in a bath of degassed water at 37° C. The tumor is then subjected to a sonodynamically effective amount of focused ultrasound with second harmonic superimposition for a sufficient time at an appropriate intensity to kill the tumor cells.

EXAMPLE 85

Tumor Cell Killing In vivo by the Synergistic Interaction of a Sonodynamic Therapy Agent and Focused ultrasound with Second Harmonic Imposition The procedure of Example 84 is used with the sonodynamic therapy compounds of Examples 1–7, 9, 11, 12, 14–65 and 67–81.

What is claimed is:

1. A method of treatment of a human or animal body by sonodynamic therapy in which a sensitizer agent is administered to said body and said body is exposed to ultrasound irradiation to achieve a cytopathogenic effect at a site therein, wherein said sensitizer agent is a physiologically tolerable radical precursor substance being a water-soluble polymer compound or a conjugate thereof, whereby the cytopathogenic efficacy of said sonodynamic therapy is enhanced by the conversion of said sensitizer agent to free radicals under the action of said ultrasound irradiation.

2. A method as claimed in claim 1 wherein the sensitizer agent is a water-soluble polymer conjugate comprising a polymeric moiety attached to one or more chromophore, targeting vector or reporter moiety.

3. A method as claimed in claim 2 wherein the water-soluble polymer conjugate comprises a polymeric moiety and one or more cyanine or cyaninoid compound.

4. A method as claimed in claim 2 wherein the water-soluble polymer conjugate comprises a polymeric moiety and one or more phthalocyanine or phthalocyaninoid compound.

5. A method as claimed in claim 2 wherein said targeting vector is selected from the group consisting of antibodies, antibody fragments, receptor-binding peptides and peptoids, tumor-targeting drug compounds, blood resistence prolonging compounds, folic acid and derivatives thereof.

6. A method as claimed in claim 1 wherein the water-soluble polymer compound or conjugate thereof is a surfactant compound containing at least one chemical functional group selected from the group consisting of an alcohol (OH), a nitrilo group, a primary amine ($NH_2$), a secondary amine (NH), a carboxylic acid (COOH), a sulfhydryl (SH), a phosphoric acid group, phosphonic acid group, a phenolic group, a sulfonic acid group, a carbon-carbon double bond, and a ketone.

7. A method as claimed in claim 6 wherein the surfactant compound comprises a polyalkyleneoxide moiety.

8. A method as claimed in claim 7 wherein the surfactant compound comprises a polyalkyleneoxide block copolymeric moiety.

9. A method as claimed in claim 1 wherein the sensitizer agent is a conjugate comprising a hydrophilic polymer moiety and a reporter moiety detectable in an in vivo diagnostic imaging modality, comprising the further step of using said modality to generate an image of at least part of said body to which said conjugate distributes.

10. A method as claimed in claim 9 wherein the imaging modality used is X-ray, MRI, ultrasound, light imaging or scintigraphy.

11. A method as claimed in claim 9 wherein the imaging modality used is light imaging and the reporter moiety is a chromophore.

12. A method as claimed in claim 9 wherein the reporter moiety is an iodinated organic compound.

13. A method as claimed in claim 1 wherein the sensitizer agent comprises a hydroperoxide.

14. A method of generating an image of a human or non-human animal body which comprises administering to said body a physiologically tolerable material and generating using an imaging technique sensitive to the presence of free radicals an image of at least part of said body to which said material distributes, comprising using as said material a free radical precursor and exposing said body to ultrasound of a power and frequency sufficient to generate free radicals from said precursor.

* * * * *